United States Patent
Grölz et al.

(10) Patent No.: US 11,203,777 B2
(45) Date of Patent: Dec. 21, 2021

(54) METHOD OF PREPARING STERILIZED COMPOSITIONS FOR STABILIZATION OF EXTRACELLULAR NUCLEIC ACIDS

(71) Applicant: Qiagen GmbH, Hilden (DE)

(72) Inventors: Daniel Grölz, Hilden (DE); Andrea Ullius, Hilden (DE)

(73) Assignee: QIAGEN GmbH, Hilden (DE)

( * ) Notice: Subject to any disclaimer, the term of this patent is extended or adjusted under 35 U.S.C. 154(b) by 345 days.

(21) Appl. No.: 15/771,820

(22) PCT Filed: Nov. 21, 2016

(86) PCT No.: PCT/EP2016/078330
§ 371 (c)(1),
(2) Date: Apr. 27, 2018

(87) PCT Pub. No.: WO2017/085321
PCT Pub. Date: May 26, 2017

(65) Prior Publication Data
US 2018/0312903 A1    Nov. 1, 2018

(30) Foreign Application Priority Data

Nov. 20, 2015 (EP) .................... 15195656
Apr. 5, 2016 (EP) .................... 16163863

(51) Int. Cl.
*C12Q 1/6806* (2018.01)
*C12N 15/10* (2006.01)

(52) U.S. Cl.
CPC ....... *C12Q 1/6806* (2013.01); *C12N 15/1003* (2013.01)

(58) Field of Classification Search
CPC .............. C12Q 1/6806; C12N 15/1003
See application file for complete search history.

(56) References Cited

U.S. PATENT DOCUMENTS

| | | |
|---|---|---|
| 3,389,133 A | 6/1968 | Gutcho |
| 3,903,179 A | 9/1975 | Bacha et al. |
| 4,555,487 A | 11/1985 | Yamada et al. |
| 4,938,961 A | 7/1990 | Collins et al. |
| 5,459,073 A | 10/1995 | Ryan |
| 5,460,797 A | 10/1995 | Ryan |
| 5,705,628 A | 1/1998 | Hawkins |
| 5,811,268 A | 9/1998 | Geri et al. |
| 5,860,397 A | 1/1999 | Schafer |
| 5,898,071 A | 4/1999 | Hawkins |
| 6,379,930 B1 | 4/2002 | Dattagupta et al. |
| 6,407,107 B1 | 6/2002 | Gilbert et al. |
| 6,534,262 B1 | 3/2003 | McKernan et al. |
| 6,602,718 B1 | 8/2003 | Augello et al. |
| 6,617,170 B2 | 9/2003 | Augello et al. |
| 6,673,364 B1 | 1/2004 | Holland et al. |
| 6,776,959 B1 | 8/2004 | Helftenbein |
| 7,270,953 B2 | 9/2007 | Holländer et al. |
| 7,332,277 B2 | 2/2008 | Dhallan |
| 7,442,506 B2 | 10/2008 | Dhallan |
| 2002/0081619 A1 | 6/2002 | Bastian et al. |
| 2003/0064000 A1 | 4/2003 | Burgess et al. |
| 2003/0118980 A1 | 6/2003 | Taylor |
| 2004/0043505 A1 | 3/2004 | Walenciak et al. |
| 2004/0167165 A1 | 8/2004 | Shankar et al. |
| 2004/0253661 A1 | 12/2004 | Goldrick et al. |
| 2005/0158699 A1 | 7/2005 | Kadkade et al. |
| 2006/0014177 A1 | 1/2006 | Hogan et al. |
| 2006/0147944 A1 | 7/2006 | Chomczynski |
| 2006/0212020 A1 | 9/2006 | Rainen et al. |
| 2007/0208166 A1 | 9/2007 | Baly et al. |
| 2008/0176209 A1 | 7/2008 | Muller et al. |
| 2008/0187924 A1 | 8/2008 | Korfhage et al. |
| 2008/0257207 A1 | 10/2008 | Rengaswamy et al. |
| 2009/0001743 A1 | 1/2009 | Roy et al. |
| 2009/0017439 A1 | 1/2009 | Shimko et al. |
| 2009/0221056 A1* | 9/2009 | Petrovick ............ A01N 1/0226 435/257.6 |
| 2009/0274765 A1 | 11/2009 | Beduneau et al. |
| 2010/0009349 A1 | 1/2010 | Holländer |

(Continued)

FOREIGN PATENT DOCUMENTS

| AU | 2011253662 A1 | 12/2011 |
|---|---|---|
| DE | 10 2007 025 277 A1 | 12/2008 |

(Continued)

OTHER PUBLICATIONS

Anonymous, "Caspase Inhibitor," BD™ ApoBlock—Technical Data Sheet (2 pages) (2008).
Baechler et al., "Expression levels for many genes in human peripheral blood cells are highly sensitive to ex vivo incubation," *Genes and Immunity* 5:347-353 (2004).
Caserta et al., "Q-VD-Oph, a broad spectrum caspase inhibitor with potent antiapoptotic properties," *Apoptosis* 8(4)345-352 (2003).
Chiu et al., "Effects of Blood-Processing Protocols on Fetal and Total DNA Quantification in Maternal Plasma," *Clinical Chemistry* 47(9): 1607-1613 (2001).
DeAngelis et al., "Solid-phase reversible immobilization for the isolation of PCR products," *Nucleic Acids Research* 23(22):4742-4743 (1995).

(Continued)

*Primary Examiner* — Ethan C Whisenant
(74) *Attorney, Agent, or Firm* — Seed IP Law Group LLP

(57) ABSTRACT

The present invention provides a method for preparing a sterilized composition suitable for stabilizing an extracellular nucleic acid population of a biological sample. Also provided are sterilizable compositions, wherein the compositions in sterilized form are suitable for stabilizing an extracellular nucleic acid population of a biological sample. Further useful methods, devices, kits and uses are also provided. Further sterilisable and sterilized compositions described herein are also suitable to stabilize intracellular nucleic acids (e.g. intracellular DNA such as genomic DNA and/or intracellular RNA) and cell characteristics, such as e.g. cell surface proteins and/or the cell morphology.

40 Claims, 11 Drawing Sheets
Specification includes a Sequence Listing.

(56) References Cited

U.S. PATENT DOCUMENTS

| | | | |
|---|---|---|---|
| 2010/0137575 | A1 | 6/2010 | Connolly et al. |
| 2010/0184069 | A1 | 7/2010 | Fernando et al. |
| 2010/0209930 | A1 | 8/2010 | Fernando |
| 2010/0255524 | A1 | 10/2010 | Holländer |
| 2010/0280233 | A1 | 11/2010 | Connolly et al. |
| 2010/0285468 | A1 | 11/2010 | Xin |
| 2010/0311166 | A1 | 12/2010 | Florio et al. |
| 2011/0027771 | A1 | 2/2011 | Deng |
| 2011/0111410 | A1 | 5/2011 | Ryan et al. |
| 2011/0306668 | A1 | 12/2011 | Yu et al. |
| 2012/0064021 | A1 | 3/2012 | Leplanquais et al. |
| 2012/0253071 | A1 | 10/2012 | Rau et al. |
| 2013/0078625 | A1 | 3/2013 | Holmes et al. |
| 2013/0323793 | A1 | 12/2013 | Tanner et al. |
| 2014/0227687 | A1 | 8/2014 | Horlitz et al. |
| 2014/0227688 | A1 | 8/2014 | Horlitz et al. |
| 2015/0056604 | A1* | 2/2015 | Sehgal .......... A01N 1/0226 435/2 |

FOREIGN PATENT DOCUMENTS

| | | |
|---|---|---|
| EP | 0 578 885 A2 | 1/1994 |
| EP | 0 880 537 B1 | 12/2004 |
| EP | 2 256 196 A1 | 12/2010 |
| GB | 2 496 969 A | 5/2013 |
| JP | 2009-521949 A | 6/2009 |
| JP | 2009-522542 A | 6/2009 |
| JP | 2011-109987 A | 6/2011 |
| WO | 95/21849 A1 | 8/1995 |
| WO | 97/34015 A1 | 9/1997 |
| WO | 97/35589 A1 | 10/1997 |
| WO | 98/29126 A1 | 7/1998 |
| WO | 98/41651 A1 | 9/1998 |
| WO | 99/57318 A2 | 11/1999 |
| WO | 01/60517 A2 | 8/2001 |
| WO | 01/70279 A1 | 9/2001 |
| WO | 03/018757 A2 | 3/2003 |
| WO | 03/086480 A1 | 10/2003 |
| WO | 2004/024958 A1 | 3/2004 |
| WO | 2004/032750 A1 | 4/2004 |
| WO | 2004/072228 A2 | 8/2004 |
| WO | 2005/067388 A2 | 7/2005 |
| WO | 2005/081867 A2 | 9/2005 |
| WO | 2006/017295 A2 | 2/2006 |
| WO | 2006/097806 A1 | 9/2006 |
| WO | 2007/077199 A2 | 7/2007 |
| WO | 2007/077560 A2 | 7/2007 |
| WO | 2008/081166 A1 | 7/2008 |
| WO | 2008/145710 A1 | 12/2008 |
| WO | 2009/016255 A1 | 2/2009 |
| WO | 2010/057184 A1 | 5/2010 |
| WO | 2010/096323 A1 | 8/2010 |
| WO | 2011/026027 A1 | 3/2011 |
| WO | 2011/026028 A1 | 3/2011 |
| WO | 2011/057061 A1 | 5/2011 |
| WO | 2011/057184 A1 | 5/2011 |
| WO | 2011/157678 A1 | 12/2011 |
| WO | 2012/151450 A1 | 11/2012 |
| WO | 2013/045432 A1 | 4/2013 |
| WO | 2013/045434 A1 | 4/2013 |
| WO | 2013/045457 A1 | 4/2013 |
| WO | 2013/045458 A1 | 4/2013 |
| WO | 2013/053855 A1 | 4/2013 |
| WO | 2014/049022 A1 | 4/2014 |
| WO | 2014/055936 A1 | 4/2014 |
| WO | 2014/131906 A1 | 9/2014 |
| WO | 2014/146780 A1 | 9/2014 |
| WO | 2014/146781 A1 | 9/2014 |
| WO | 2014/146782 A1 | 9/2014 |
| WO | 2015/140218 A1 | 9/2015 |
| WO | 2016/022433 A1 | 2/2016 |

OTHER PUBLICATIONS

Dupuis et al., "Molecular-crowding effects on single-molecule RNA folding/unfolding thermodynamics and kinetics," *PNAS* 111(23):8464-8469 (Jun. 10, 2014).

Eckert et al., "Caspase inhibitors," *Cell Death and Differentiation* 6:1081-1086, 1999.

MP Biomedicals, "Q-VD-OPH (OPH109), a new generation broad caspase inhibitor from innovators of Z-VAD(OMe)-FMK Casper Inhibitor / Apoptosis Inhibitor," downloaded from https://www.mpbio.com/detailed_info.php?family_key=03OPH109&country=223 on Sep. 5, 2017, 5 pages.

Fan et al., "Analysis of the Size Distributions of Fetal and Maternal Cell-Free DNA by Paired-End Sequencing," *Clinical Chemistry* 56(8):1-8 (2010).

Fernando et al., "Preservation and Amplification of Fetal Cell-Free DNA in Maternal Plasma for Noninvasive Prenatal Diagnosis," *Streck*, First Presented at AACC/ASCLS Clinical Lab Expo on Jul. 23, 2009.

Fernando et al., "Stabilization of Cell-Free RNA in Plasma for Noninvasive Diagnosis," *Streck*, Presented at AACC Annual Meeting Jul. 2010, Anaheim, CA.

Fleischhacker et al., "Circulating nucleic acids (CNAs) and cancer—A survey," *Biochimica et Biophysica Acta* 1775:181-232 (2007).

Fleischhacker, "Biology of Circulating mRNA—Still More Questions Than Answers?" *Ann. N.Y. Acad. Sci.* 1075:40-49 (2006).

Goldstein et al., "Caspase-independent cytochrome c release is a sensitive measure of low-level apoptosis in cell culture models," *Aging Cell* 4(4):217-222 (2005).

Hromadnikova et al., "Quantification of Fetal and Total Circulatory DNA in Maternal Plasma Samples Before and After Size Fractionation by Agarose Gel Electrophoresis," *DNA and Cell Biology* 25(11):635-640 (2006).

Jani et al., "Caspase Inhibition Prevents the Increase in Caspase-3, -2, -8 and -9 Activity and Apoptosis in the Cold Ischemic Mouse Kidney," *American Journal of Transplantation* 4:1246-1254, 2004.

Karimata et al., "Stabilization of a DNA duplex under molecular crowding conditions of PEG," *Nucleic Acids Symposium Series* No. 48:107-108 (2004).

Ke et al., "Characterizing DNA Condensation and Conformational Changes in Organic Solvents," *PLoS ONE* 5(10): 2010, 8 pages.

Kruhøffer et al., "Isolation of Microarray-Grade Total RNA, MicroRNA, and DNA from a Single PAXgene Blood RNA Tube," *Journal of Molecular Diagnostics* 9(4):452-458 (Sep. 2007).

Lis et al., "Size fractionation of double-stranded DNA by precipitation with polyethylene glycol," *Nucleic Acids Research* 2(3):383-389 (Mar. 1975).

Marino et al., "Lysosomal and mitochondrial permeabilization mediates zinc(II) cationic phthalocyanine phototoxicity," *The International Journal of Biochemistry & Cell Biology* 45:2553-2562 (2013).

Mosbah et al., "Effects of Polyethylene Glycol and Hydroxyethyl Starch in University of Wisconsin Preservation Solution on Human Red Blood Cell Aggregation and Viscosity," *Transplantation Proceedings* 38: 1229-1235 (2006).

Mukae et al., "Molecular cloning and characterization of human caspase-activated DNase," *Proc. Natl. Acad. Sci. USA* 95:9123-9128 (1998).

Müller et al., "Improvement of molecular monitoring of residual disease in leukemias by bedside RNA stabilization," *Leukemia* 16:2395-2399 (2002).

Notice of Reasons for Refusal with English Translation, dated Jun. 1, 2016, for Japanese Application No. 2014-532357, 11 pages.

Pahl, "Gene expression changes in blood after phlebotomy: implications for gene expression profiling," *Blood* 100(3):1-2 (Aug. 1, 2002).

Paithankar et al., "Precipitation of DNA by polyethylene glycol and ethanol," Nucleic Acids Research 19(6):1346 (Feb. 6, 1991).

QIAamp® Circulating Nucleic Acid Handbook, QIAGEN®—Sample & Assay Technologies (44 pages) (May 2009).

Rainen et al., "Stabilization of mRNA Expression in Whole Blood Samples," *Clinical Chemistry* 48(11): 1883-1890 (2002).

Samejima et al., "Trashing the Genome: the Role of Nucleases During Apoptosis," *Nature Reviews* 6:677-688, 2005.

(56) References Cited

OTHER PUBLICATIONS

Sethu et al., "Microfluidic Isolation of Leukocytes from Whole Blood for Phenotype and Gene Expression Analysis," *Anal. Chem.* 76:5453-5461 (2006).

Swarup et al., "Circulating (cell-free) nucleic acids—A promising, non-invasive tool for early detection of several human diseases," *FEBS Letters* 581:795-799 (2007).

BD Pharmingen, Technical Data Sheet, "Z-VAD-FMK, General Caspase Inhibitor," (2 pages) (2008).

Decision of Rejection corresponding to Chinese Patent Application No. 201280046949.4, English Translation, 3 pages, dated May 25, 2018.

Xu, "Guidance Book of Malignant Tumor Chemotherapy and Strategies Thereof for National Self-Taught Higher Education Examinations for Chinese Medicine Majors," (Bachelor) with Partial English Translation, 7 pages, (2002).

Zhao et al., "Collection of Essays at 60th Anniversary of Animal Society of China for Commemorating 100th Anniversary of Professor Chen Zhen's Birth," with Partial English Translation, 6 pages, (1994).

Japanese Office Action dated Dec. 17, 2020 corresponding to Japanese Patent Application No. 2018-525690, 15 pages, with translation.

\* cited by examiner

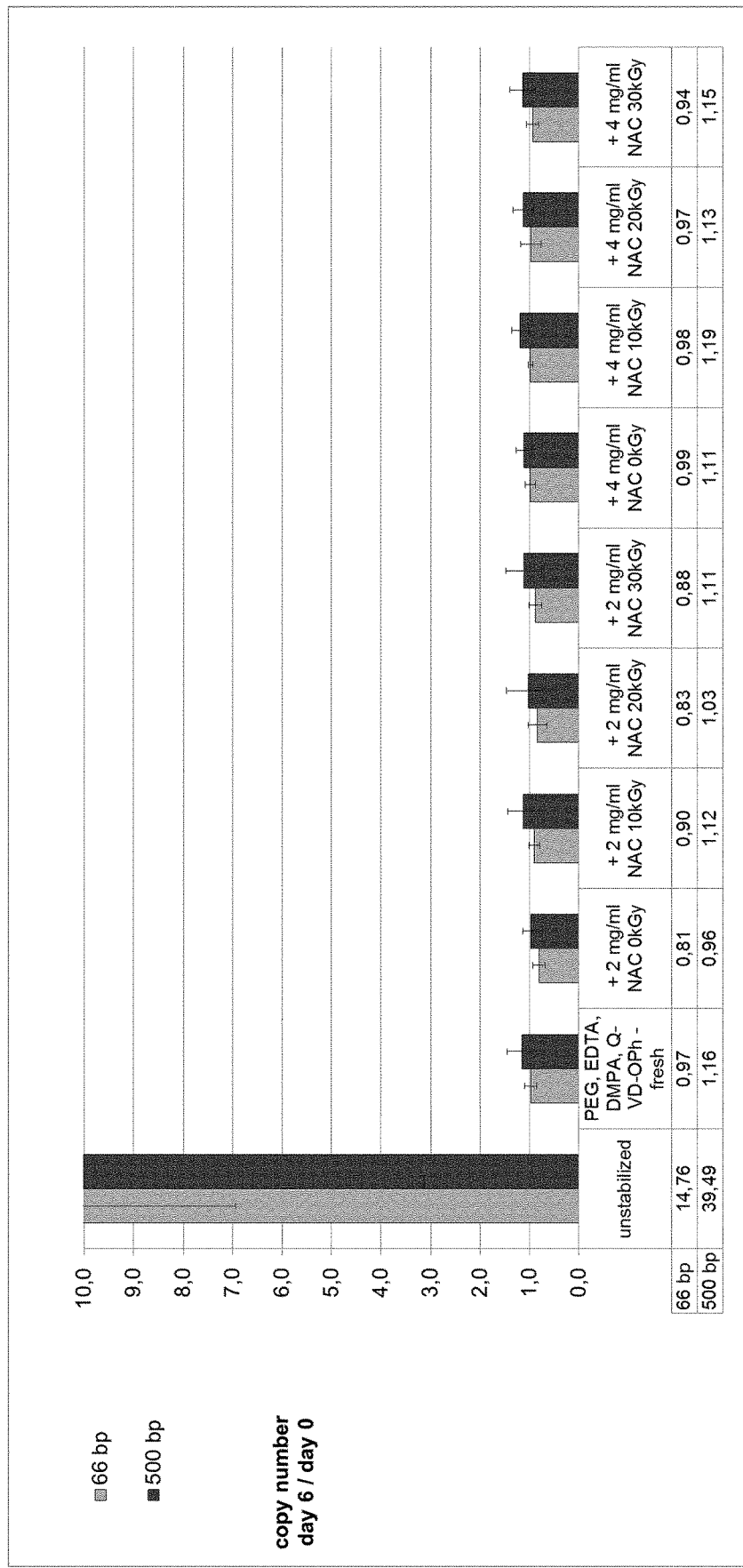

SEQUENCE LISTING

```
<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: human ribosomal DNA forward primer

<400> SEQUENCE: 1
gccgctagag gtgaaattct tg                                              22

<210> SEQ ID NO 2
<211> LENGTH: 21
<212> TYPE: DNA
<213> ORGANISM: Artificial Sequence
<220> FEATURE:
<223> OTHER INFORMATION: human ribosomal DNA reverse primer

<400> SEQUENCE: 2
cattcttggc aaatgctttc g                                               21

<210> SEQ ID NO 3
<211> LENGTH: 21
<212> TYPE: DNA
<213> ORGANISM: Artificial Sequence
<220> FEATURE:
<223> OTHER INFORMATION: human ribosomal DNA probe

<400> SEQUENCE: 3
accggcgcaa gacggaccag a                                               21

<210> SEQ ID NO 4
<211> LENGTH: 22
<212> TYPE: DNA
<213> ORGANISM: Artificial Sequence
<220> FEATURE:
<223> OTHER INFORMATION: human ribosomal DNA forward primer

<400> SEQUENCE: 4
gtcgctcgct cctctcctac tt                                              22
```

```
<210> SEQ ID NO 5
<211> LENGTH: 19
<212> TYPE: DNA
<213> ORGANISM: Artificial Sequence
<220> FEATURE:
<223> OTHER INFORMATION: human ribosomal DNA reverse primer

<400> SEQUENCE: 5
ggctgctggc accagactt                                              19

<210> SEQ ID NO 6
<211> LENGTH: 25
<212> TYPE: DNA
<213> ORGANISM: Artificial Sequence
<220> FEATURE:
<223> OTHER INFORMATION: human ribosomal DNA probe

<400> SEQUENCE: 6
ctaatacatg ccgacgggcg ctgac                                       25
```

METHOD OF PREPARING STERILIZED COMPOSITIONS FOR STABILIZATION OF EXTRACELLULAR NUCLEIC ACIDS

STATEMENT REGARDING SEQUENCE LISTING

The Sequence Listing associated with this application is provided in text format in lieu of a paper copy, and is hereby incorporated by reference into the specification. The name of the text file containing the Sequence Listing is 771025 408USPC SEQUENCE LISTING.txt. The text file is 2 KB, was created on Apr. 26, 2018, and is being submitted electronically via EFS-Web.

The present invention provides a method for preparing a sterilized composition that is suitable for stabilizing an extracellular nucleic acid population of a biological sample. Also provided are sterilizable compositions, wherein the compositions in sterilized form are suitable for stabilizing an extracellular nucleic acid population of a biological sample. Further useful methods, devices, kits and uses are also provided. In particular, sterilisable and sterilized compositions suitable for stabilizing a cell-containing sample such as e.g. a blood sample are provided. In embodiments these compositions are suitable for stabilizing intracellular nucleic acids (e.g. intracellular DNA and/or intracellular RNA), cell surface characteristics and/or the cell morphology.

Extracellular nucleic acids have been identified in blood, plasma, serum and other body fluids. Extracellular nucleic acids that are found in respective samples are to a certain extent degradation resistant due to the fact that they are protected from nucleases (e.g. because they are secreted in form of a proteolipid complex, are associated with proteins or are contained in vesicles). The presence of altered such as elevated levels of extracellular nucleic acids such as DNA and/or RNA in many medical conditions, malignancies, and infectious processes is of interest inter alia for screening, diagnosis, prognosis, surveillance for disease progression, for identifying potential therapeutic targets, and for monitoring treatment response. Additionally, elevated fetal DNA/RNA in maternal blood is being used to determine e.g. gender identity, assess chromosomal abnormalities, and monitor pregnancy-associated complications. Thus, extracellular nucleic acids are in particular useful in non-invasive diagnosis and prognosis and can be used e.g. as diagnostic markers in many fields of application, such as non-invasive prenatal genetic testing, oncology, transplantation medicine or many other diseases and, hence, are of diagnostic relevance (e.g. fetal- or tumor-derived nucleic acids). However, extracellular nucleic acids are also found in healthy human beings. Besides mammalian extracellular nucleic acids that derive e.g. from tumor cells or the fetus, cell-containing samples may also comprise other nucleic acids of interest that are not comprised in cells. An important, non-limiting example is pathogen nucleic acids such as viral nucleic acids. Preservation of the integrity of viral nucleic acids in cell-containing samples such as in particular in blood specimens during shipping and handling is also crucial for the subsequent analysis and viral load monitoring. Common applications and analysis methods of extracellular nucleic acids are e.g. described in WO 97/035589, WO 97/34015, Swarup et al, FEBS Letters 581 (2007) 795-799, Fleischhacker Ann. N.Y. Acad. Sci. 1075: 40-49 (2006), Fleischhacker and Schmidt, Biochmica et Biophysica Acta 1775 (2007) 191-232, Hromadnikova et al (2006) DNA and Cell biology, Volume 25, Number 11 pp 635-640; Fan et al (2010) Clinical Chemistry 56:8.

While analysis of extracellular nucleic acids is of high interest, their analysis was found to be difficult for several reasons. Extracellular nucleic acids are usually only comprised in a low concentration in the samples. Furthermore, extracellular nucleic acids often circulate as fragments of a size of 500 nt, 300 nt (when indicating the size and hence the chain length the term "nt" also includes "bp" in case of DNA) or even less (circulating nucleosomes). For circulating cell-free DNA (ccfDNA) in plasma, the average length is often only approx. 140-170 bp. Additionally, the actual target extracellular nucleic acid that is supposed to be identified for diagnostic purposes usually also represents only a small fraction among the total extracellular nucleic acids. With respect to ccfDNA, usually only a few thousand amplifiable copies are present per ml of blood depending e.g. on the pregnancy state or tumor grade. Specifically tumor specific DNA fragments are very rare and often are comprised in a concentration that is 1000-fold less than the "normal" extracellular nucleic acid background. This low concentration poses challenges with respect to the stabilization of the sample and the subsequent isolation of the extracellular nucleic acids from the stabilized samples. Also, a major problem regarding the analysis of circulating, cell-free nucleic acids (cfNA) such as from tumors or of foetal origin is—besides the degradation that occurs in serum and probably also plasma—the possible dilution of extracellular DNA (and RNA) by genetic material from damaged or decaying cells after sample collection. After the sample was collected, cellular nucleic acid are released from the cells contained in the sample due to cell breakage during ex vivo incubation, typically within a relatively short period of time after sample collection. Once cell lysis begins, the lysed cells release large amounts of additional nucleic acids which become mixed with the extracellular nucleic acids and it becomes increasingly difficult to recover the extracellular nucleic acids for testing.

The release from intracellular nucleic acids after sample collection particularly is an issue if the sample comprises a high amount of cells as is the case e.g. with whole blood samples. With respect to blood samples, in particular the lysis of white blood cells is a problem as they release large amounts of genomic DNA in addition to RNA. Red blood cells do not contain genomic DNA. Therefore, stabilization of circulating nucleic acids in whole blood must include mechanism to stabilize blood cells in order to prevent during stabilization a contamination of the extracellular nucleic acid population by cellular genomic DNA and also RNA. In particular the dilution of the extracellular nucleic acids, in particular rare target extracellular nucleic acids, is an issue and must be prevented. These problems are discussed in the prior art (see e.g. Chiu et al (2001), Clinical Chemistry 47:9 1607-1613; Fan et al (2010) and US 2010/0184069). Further, the amount and recoverability of available extracellular nucleic acids can decrease substantially over a period of time, due to degradation.

To address these problems and the need for efficient stabilization of extracellular nucleic acids, a number of methods, compositions and devices for stabilizing an extracellular nucleic acid population have been developed.

The use of formaldehyde or formaldehyde releasers for stabilization is described in U.S. Pat. Nos. 7,332,277, 7,442, 506 and US 2011/0111410. Methods to stabilize blood samples are also described e.g. in US 2010/0184069 and US 2010/0209930. However, the use of formaldehyde or formaldehyde-releasing substances has drawbacks. Formaldehyde is toxic. Moreover, these stabilizers can chemically modify biomolecules like proteins and nucleic acids. They can therefore compromise the efficacy of extracellular nucleic acid isolation by inducing crosslinks between nucleic acid molecules or between proteins and nucleic acids. This can reduce especially the number of nucleic acids molecules to be amplifiable or accessible for diagnosis. Since the number of ccfDNA in plasma is limited to only a few thousand copies per milliliter of blood this is a huge disadvantage.

Besides extracellular nucleic acids, also other nucleic acids are important biomarkers in the diagnostic field. E.g. profiles of transcripts of the genome (in particular mRNA and miRNA) are widely used as biomarkers in molecular in vitro diagnostics and provide inside into normal biological and pathological processes with the hope of predicting disease outcome and indicating individualized courses of therapy. Therefore, profiling of nucleic acids, in particular RNA, is important in disease diagnosis, prognosis and in clinical trials for biomarker discovery. However, without precaution in the stabilisation of the sample to be analysed, the sample will undergo changes during transport and storage that may severely alter the expression profile of the targeted molecules (see for example Rainen et al, 2002; Baechler et al, 2004). Thus, gene expression, in particular blood cell gene expression is sensitive to ex vivo handling of the sample. If the expression profile is altered due to the handling of the sample, the subsequent analysis does not reflect the original situation of the sample and hence of the patient but rather measure an artificial profile generated during sample handling, transport and storage. Therefore, optimized stabilisation processes are needed which stabilise the expression profile thereby allowing the reliable analysis. In particular, there is a need to stabilize blood samples in order to allow the analysis of blood cell gene expression profiles.

Many known technologies for stabilizing the expression profile are based on cell lysis (e.g. PAXgene Blood RNA Tubes, U.S. Pat. Nos. 6,617,170, 7,270,953, Kruhoffer et al, 2007). The disadvantage of the respective methods is that the stabilisation results in the complete lysis of the cells. The destruction of the cells results in that intracellular nucleic acids become mixed with extracellular nucleic acids which prevents the separate analysis of these two nucleic acid populations. Moreover, the destruction of the cells makes any cell sorting or cell enrichment respectively cell analysis impossible. Therefore, for certain applications sample collection and stabilisation systems are needed, which preserve the cell's morphology while at the same time stabilising the nucleic acids. To address the need of simultaneous cell stabilisation and nucleic acid stabilisation, stabilisation systems were developed that are based on the use of formaldehyde releasers (e.g. cell-free RNA BCT (blood collection tube), US 2011/0111410). However, nucleic acid isolation from respectively stabilised samples is very difficult, because the used formaldehyde releaser interferes with the subsequent nucleic acid isolation process. Thus, similar problems occur as described above for extracellular nucleic acids.

To overcome the above described disadvantages, stabilization technologies were developed that do not require the use of crosslinking agents such as formaldehyde or formaldehyde releasers. These stabilization technologies are disclosed e.g. in WO 2013/045457 A1, WO 2014/146780 A1, WO 2014/146782 A1, PCT/E P2015/055699 (WO 2015/140218), WO 2014/049022 A1, WO 2013/045458 A1, WO 2013/045432 A1, and WO 2014/146781 A1. The described technologies use inter alia a caspase inhibitor either alone or in combination with other stabilizing compounds such as primary, secondary or tertiary amides in order to stabilize the extracellular nucleic acid population. These stabilization technologies reduce contaminations of the extracellular nucleic acid population by intracellular nucleic acids, in particular by genomic DNA, after sample collection and stabilization. WO 2014/049022, WO 2014/146780, WO 2014/146782 and WO 2014/146781 also teach corresponding stabilizing compositions suitable to stabilize intracellular nucleic acids (in particular the gene expression profile). Furthermore, these applications disclose stabilizing compositions which allow the subsequent analysis of the stabilized cells, such as cell surface characteristics and/or the cell morphology. Furthermore, WO 2008/145710 describes a method for stabilizing cell-containing samples, such as blood or tissue samples, which stabilize e.g. the cells, the transcriptome, genome and proteome. While these applications provide efficient stabilization technologies that ensure e.g. the stabilization of the extracellular nucleic acids, they do not specifically address the aspect of sterilization and sterility of the disclosed stabilization compositions and devices.

However, the use of these stabilization compositions in sterilized form offers several advantages. For example, the shelf-life of the compositions can be increased. Also, storage times of the stabilized sample in certain applications can be further increased when the sample is contacted with sterilized compositions for stabilization. Sterilized compositions suitable for stabilizing an extracellular nucleic acid population are particularly useful if the biological sample is collected e.g. from a human or an animal and is directly contacted with the stabilization composition. This is for example the case where the stabilization composition is comprised in a sample collection device, such as a blood collection device or tube, which also may be subject to regulatory requirements. The same applies if a stabilizing composition is used that also stabilizes intracellular nucleic acids.

Therefore, providing sterile stabilization compositions offers significant advantages from a safety and/or regulatory perspective in a large number of applications. Yet, albeit sterilization of compositions for stabilizing extracellular and/or intracellular nucleic acids and devices comprising such compositions is desirable, the sterilization process poses several problems. On the one hand, sterilization should be performed under conditions stringent enough so as to ensure sterility of the resulting composition or device. On the other hand, applying such sterilization conditions may interfere with relevant properties of the stabilization composition. It was e.g. found that common sterilization processes can significantly reduce the stabilization performance of the composition in stabilizing an extracellular nucleic acid population in biological samples. In addition, measures implemented for sterilization ideally should not interfere with further downstream applications, such as isolation of stabilized extracellular nucleic acids and processing or analysis of the isolated nucleic acids. The same applies if a stabilizing composition is used that also stabilizes intracellular nucleic acids.

Amongst the available sterilization methods, sterilization by irradiation offers advantages. Irradiation works without excessive heat and does not expose the product to be sterilized to toxic chemicals. Forms of irradiation commonly applied for sterilization purposes in general include ionizing irradiation forms such as gamma irradiation, X-ray and electron beam irradiation. For example, sterilization by gamma irradiation according to ISO norms (in particular ISO11137-1:2006, ISO11137-2:2012, ISO11137-3:2006)

can be performed as part of the production process for single-use medical devices such as the production process for sample collection devices like blood collection tubes. Sterilization of single-use medical devices by electron beam radiation is likewise governed by ISO standards 1137 and 13409.

For sterilization by irradiation, e.g. gamma irradiation, irradiation doses should be chosen that are high enough to ensure the desired level of sterility. Also, in the production of compositions and devices for sample collection, such as in particular blood collection devices or tubes, the minimum requirements regarding sterility and irradiation doses set out in the relevant ISO norms should be fulfilled. Typically, sterilization for medical applications has to assure a probability of not higher than $10^{-6}$ that a single unit is non-sterile after it has been subjected to sterilization. A $10^{-6}$ probability of microbial survival leads to a "Sterility Assurance Level" (SAL) of 1 out of 1,000,000—the chance of one single viable microorganism to occur on an item after sterilization. Execution of gamma irradiation and determination of minimal dose which guarantees a SAL of $10^{-6}$ is standardized by several ISO norms (ISO11137-1:2006, ISO11137-2:2012, ISO11137-3:2006). The minimal dose required to reach SAL of $10^{-6}$ depends on the initial bioburden of the product.

It is also often desirable to sterilize with irradiation doses above the minimal sterilization dose. For example, irradiation at given higher doses often is more convenient from a practical point of view of the workflow in an irradiation facility. Also, choosing irradiation doses above the minimal sterilization dose may provide important advantages because depending on the dose applied, simplified microbiological testing can be performed to confirm product sterility. Depending on the irradiation dose applied, the product may be labelled as sterile with reduced or even without microbiological testing. For example, one relevant lower border for sterilizing sample collection devices such as blood collection tubes is an irradiation with a dose of about 7.8 kGy or 8 kGy. Dosages≥8 kGy are generally adequate to eliminate low bioburden levels. In cases where bioburden level is elevated higher doses may be required to achieve sterility. If the tubes are irradiated with a dose of 15 kGy, often simplified microbiological testing can be applied to determine and confirm sterility. Generally, 25 kGy can achieve sterility with a sterility assurance level (SAL) of $10^{-6}$. Even with elevated bioburden levels, bioburden reduction can be achieved with lower probabilities of sterility (e.g., SAL of $10^{-5}$ or $10^{-7}$). Therefore, no microbiological testing may be required to be able to label blood collection tubes irradiated with a (comparably high) dose of 25 kGy as sterile what is a significant advantage.

Yet, irradiation such as e.g. gamma irradiation, X-ray or electron beam irradiation, results in the formation of free radicals. Formation of radicals during irradiation can lead to degradation or loss of active ingredient potency of the sterilized product once the irradiation dose applied is higher than the maximum irradiation dose. The maximum irradiation dose can be defined as the sterilization dose that does not affect the integrity of the product, i.e. the maximum dose which does not lead to degradation effects. For example, because of the known degradation problems, gamma irradiation is not widely used for aqueous drug products and pharmaceuticals with a proteinaceous component (STERIS® Isomedix Services, TechTip 01/09/07, Rev 1).

Several measures have been proposed in case the initial bioburden of a product determines a minimal sterilization dose that is higher than the maximum tolerable dose. These measures comprise improvements of the production process such as the use of clean and sterilized components and equipment, filtration and the like. However, implementing these measures is costly and using sterilized components may not always be feasible. Albeit these measures may be helpful in achieving a lower minimal sterilization dose, sterilization of the final product is still required. Other strategies described for mitigating degradation effects include reduced- or controlled-temperature irradiation, adjustment of dose rate, minimizing water content or irradiation in dry or solid form and the use of additives that act as radioprotectants. However, these strategies frequently are not applicable in a generalized manner and implementation of an appropriate strategy also depends on the product or composition to be sterilized.

Thus, it is a well-known problem that the conditions required to achieve sterilization, in particular sterilization by irradiation, may result in degradation of active components of the stabilization composition and may thus reduce or even abolish the ability of the stabilization composition to stabilize extracellular nucleic acid populations once it is sterilized. The same applies when using stabilizing compositions which also stabilize intracellular nucleic acids and/or cell characteristics; the stabilizing properties must be maintained after sterilization.

The inventors found that a caspase inhibitor containing composition for stabilizing an extracellular nucleic acid population in a sample showed a significantly reduced performance after sterilization by irradiation. Of course, such a negative impact of the sterilization process on the stabilizing properties of the stabilization composition is undesirable. Albeit measures can be taken to reduce the minimal sterilization dose required for a given product, these measures typically are not sufficient to ensure sterility of the final product on their own, and reducing the minimal sterilization dose does not address the situation where application of irradiation doses above the maximal sterilization dose is desirable e.g. for reasons set out above. Many of the strategies for mitigating degradation effects discussed above have been developed for pharmaceutical products and are not readily transferable to nucleic acid-related applications because different considerations apply.

An appropriate strategy for sterilizing a composition suitable for stabilizing a nucleic acid population in a biological sample needs to ensure an appropriate stabilizing function after sterilization and ideally does not interfere with further downstream processes such as nucleic acid isolation and/or analysis. Appropriate stabilization performance after sterilization is especially relevant for extracellular nucleic acid populations, which are often comprised in a biological sample in low concentrations.

Therefore, it is an object of the present invention to overcome at least one of the drawbacks of the prior art discussed above. In particular, it is an object of the present invention to provide a method of preparing a sterilized composition that comprises a caspase inhibitor and that is also after sterilization suitable for stabilizing an extracellular nucleic acid population of a biological sample such as a cell-containing biological sample. It is a further object of the present invention to provide a corresponding sterilizable composition, wherein the composition in sterilized form is suitable for stabilizing an extracellular nucleic acid population of such biological samples. It is a further object of the present invention to prevent the degradation of one or more active ingredients contained in the stabilization composition, such as the caspase inhibitor, during sterilization by irradiation in order to maintain the stabilisation characteristics in the sterilized composition. It is therefore desirous and thus an object of the present invention to maintain one or more stabilisation characteristics of the sterilizable composition in the sterilized composition. It is a further object to provide corresponding sterilization technologies for a caspase inhibitor containing stabilization composition that stabilizes e.g. i) cells comprised within a biological sample, ii) comprised intracellular nucleic acids (e.g. DNA and/or RNA, in particular for stabilizing the gene expression profile of contained cells) and/or iii) cell associated proteins such as cell surface proteins.

SUMMARY OF THE INVENTION

The present invention is based on the surprising finding that a caspase inhibitor containing composition that is suitable for stabilizing an extracellular nucleic acid population of a biological sample (also referred to herein as "stabilization composition" or "stabilizing composition") can be efficiently protected from degradation effects during sterilization by irradiation if at least one compound selected from a thioalcohol (such as preferably N-acetyl-cysteine or glutathione), a water-soluble vitamin, and vitamin E or a derivative thereof is included in the stabilization composition. Surprisingly, one or more of these compounds can be included into the stabilizing composition for degradation protection without negatively affecting the extracellular nucleic acid stabilization properties. Also, including at least one of these compounds into the stabilization composition advantageously does not interfere with downstream applications, such as isolation and/or analysis of the stabilized extracellular nucleic acid population. These compounds thus protect the composition respectively at least one active component thereof, such as in particular the caspase inhibitor, from degradation during the irradiation sterilization and efficiently preserve the stabilizing characteristics of the stabilization composition upon sterilization.

The method of the present invention significantly facilitates the sterilization of compositions suitable for stabilizing an extracellular nucleic acid population of a biological sample by irradiation, such as gamma irradiation, electron beam irradiation or X-ray. It allows to prepare sterilized stabilization compositions that are based on a stabilization composition comprising one or more caspase inhibitors and optionally one or more other stabilizing agents disclosed in WO 2013/045457 A1, WO 2014/146780 A1, WO 2014/146782 A1, PCT/EP2015/055699, WO 2014/049022 A1, WO 2013/045458 A1 and WO 2014/146781 A1, herein incorporated by reference. As discussed, these applications also disclose stabilizing compositions suitable for stabilizing intracellular nucleic acids, such as intracellular DNA (e.g. genomic DNA) and/or intracellular RNA (in particular the gene expression profile) of the contained cells. The present method in particular allows to prepare a sterilized stabilization composition that is based on the highly efficient and advantageous stabilization compositions comprising one or more caspase inhibitors disclosed in PCT/EP2015/055699, herein incorporated by reference. The stabilization composition can conveniently be prepared and/or sterilized directly in a sample collection device.

By using a compound selected from a thioalcohol, a water-soluble vitamin, and vitamin E or a derivative thereof, it is furthermore possible to prepare a liquid composition that can be sterilized by irradiation. A sterilized composition in liquid, in particular aqueous, form is highly advantageous. In the stabilization of e.g. blood samples, the use of a sterilized liquid or aqueous stabilization composition allows for example to reduce hemolysis and thus improve the stabilization effect. With the present methods, it is possible to prepare and sterilize liquid stabilization compositions including those that have a mild pH, in particular a mildly acidic pH. Sterilization can be performed without having to revert to strongly basic or strongly acidic pH conditions. A mildly acidic pH contributes to avoid or reduce the occurrence of precipitates in the stabilization composition during sterilization.

The present invention also allows to prepare a sterilized stabilization composition having an extended-shelf life compared to non-sterilized stabilization compositions and to sterilization compositions sterilized without the aforementioned compounds.

According to a first aspect, the present invention thus provides a method for producing a sterilized composition suitable for stabilizing an extracellular nucleic acid population of a biological sample, the method comprising:
   a) providing a composition comprising:
      i. at least one caspase inhibitor, and
      ii. at least one compound selected from a thioalcohol (preferably N-acetyl-cysteine or glutathione), a water-soluble vitamin, and vitamin E or a derivative thereof; and
   b) irradiating the composition for sterilization.

According to a second aspect, the present invention provides a method for stabilizing an extracellular nucleic acid population comprised in a cell-containing biological sample comprising:
   a) obtaining i) a sterilized composition suitable for stabilizing an extracellular nucleic acid population of a biological sample according to the method of the first aspect of the invention, or ii) a composition according to the sixth aspect of the invention in sterilized form; and
   b) contacting the cell-containing biological sample with the sterilized composition for stabilization.

According to a third aspect, the present invention provides a method for isolating extracellular nucleic acids from a stabilized cell-containing biological sample comprising:
   a) stabilizing the cell-containing biological sample according to the method of the second aspect of the invention; and
   b) isolating extracellular nucleic acids.

According to a fourth aspect, the present invention provides a method for processing and/or analyzing extracellular nucleic acids comprising:
   a) isolating extracellular nucleic acids from a stabilized cell-containing biological sample according to the method of the third aspect of the invention; and
   b) processing and/or analyzing the isolated extracellular nucleic acids.

According to a fifth aspect, the present invention provides a method for producing a sterilizable composition, wherein the composition in sterilized form is suitable for stabilizing an extracellular nucleic acid population of a biological sample, the method comprising:
   a) preparing a composition comprising:
      i. at least one caspase inhibitor, and
      ii. at least one compound selected from a thioalcohol (preferably N-acetyl-cysteine or glutathione), a water-soluble vitamin, and vitamin E or a derivative thereof, and optionally
   b) sterilizing the composition.

This method can be used to prepare the composition according to the sixth aspect.

According to a sixth aspect, the present invention provides a sterilizable composition, wherein the composition in sterilized form is suitable for stabilizing an extracellular nucleic acid population of a biological sample, wherein the composition is a composition as provided in step a) of the method according to the first aspect of the invention. It comprises i. at least one caspase inhibitor, and ii. at least one compound selected from a thioalcohol (preferably N-acetyl-cysteine or glutathione), a water-soluble vitamin, and vitamin E or a derivative thereof. The sterilizable composition according to the sixth aspect, which can be a composition as provided in step a) of the method according to the first aspect of the invention, in embodiments can be sterilized to provide a sterilized composition.

According to a seventh aspect, the present invention provides a sample collection device such as a container, preferably a sample collection tube, comprising the sterilizable composition according to the sixth aspect of the invention.

According to an eights aspect, the present invention provides a kit comprising a composition according to the sixth aspect of the invention, or a sample collection device according to the seventh aspect of the invention.

According to a ninth aspect, the present invention pertains to the use of at least one compound selected from the group consisting of a thioalcohol (preferably N-acetyl-cysteine or glutathione), a water-soluble vitamin, and vitamin E or a derivative thereof, for protecting a composition suitable for stabilizing an extracellular nucleic acid population of a biological sample or components thereof during sterilization by irradiation.

Further aspects of the invention are provided in the detailed description below.

The present technologies allow to prepare sterilizable and sterilized compositions suitable for stabilizing an extracellular nucleic acid population in a biological sample in a convenient, reliable, safe and cost-efficient manner. Such stabilization compositions are especially advantageous for applications where a biological sample is to be collected from a human or animal, such as e.g. a blood sample. In these applications, from a safety point of view, sterility of the stabilization composition and device is highly preferable. Moreover, according to the present invention, non-toxic compounds can be used as irradiation protective agents, which likewise contributes to safety. In embodiments, the provided sterilizable and sterilized compositions are also suitable for stabilizing intracellular nucleic acids (e.g. intracellular DNA such as genomic DNA and/or intracellular RNA), in particular the gene expression profile of contained cells. In further embodiments, the provided sterilizable and sterilized compositions are suitable to stabilize a cell-containing sample so that cells contained in the stabilized sample can be analysed, e.g. based on cell surface characteristics and/or the cell morphology.

In particular, the present invention allows to prepare a liquid irradiation sterilized stabilization composition comprising a caspase inhibitor. Sterilization of liquids by irradiation frequently interferes with the activity of the product to be sterilized. The present inventors found that incorporating at least one compound selected from a thioalcohol (preferably N-acetyl-cysteine and/or glutathione), a water-soluble vitamin, and vitamin E or a derivative thereof into a stabilization compositions comprising a caspase inhibitor protects the stabilizing composition from irradiation induced degradation while not interfering with the stabilization properties of the stabilization composition. This provides a sterilized composition that maintains the stabilizing characteristics. These advantageous effects were not seen with other compounds that are used as radical scavenger. N-acetyl-cysteine, ascorbic acid and glutathione in reduced form have been found to be particularly effective.

Providing a liquid sterile composition is particularly useful. For example it allows for a rapid and homogenous admixing of the stabilization composition and a liquid biological sample, such as whole blood or a blood derived sample like plasma or serum. Moreover, using a liquid, preferably aqueous, composition reduces hemolysis.

Furthermore, sterilizing a stabilizing composition according to method of the present invention can furthermore improve the storage properties of the stabilization composition and allows for an extended shelf-life compared to non-sterilized compositions and compositions sterilized without at least one of a thioalcohol (preferably N-acetyl-cysteine, glutathione), a water-soluble vitamin, and vitamin E or a derivative thereof. This is a further advantage.

Other objects, features, advantages and aspects of the present application will become apparent to those skilled in the art from the following description and appended claims. It should be understood, however, that the following description, appended claims, and specific examples, while indicating preferred embodiments of the application, are given by way of illustration only. Various changes and modifications within the spirit and scope of the disclosed invention will become readily apparent to those skilled in the art from reading the following.

Figure 8A:
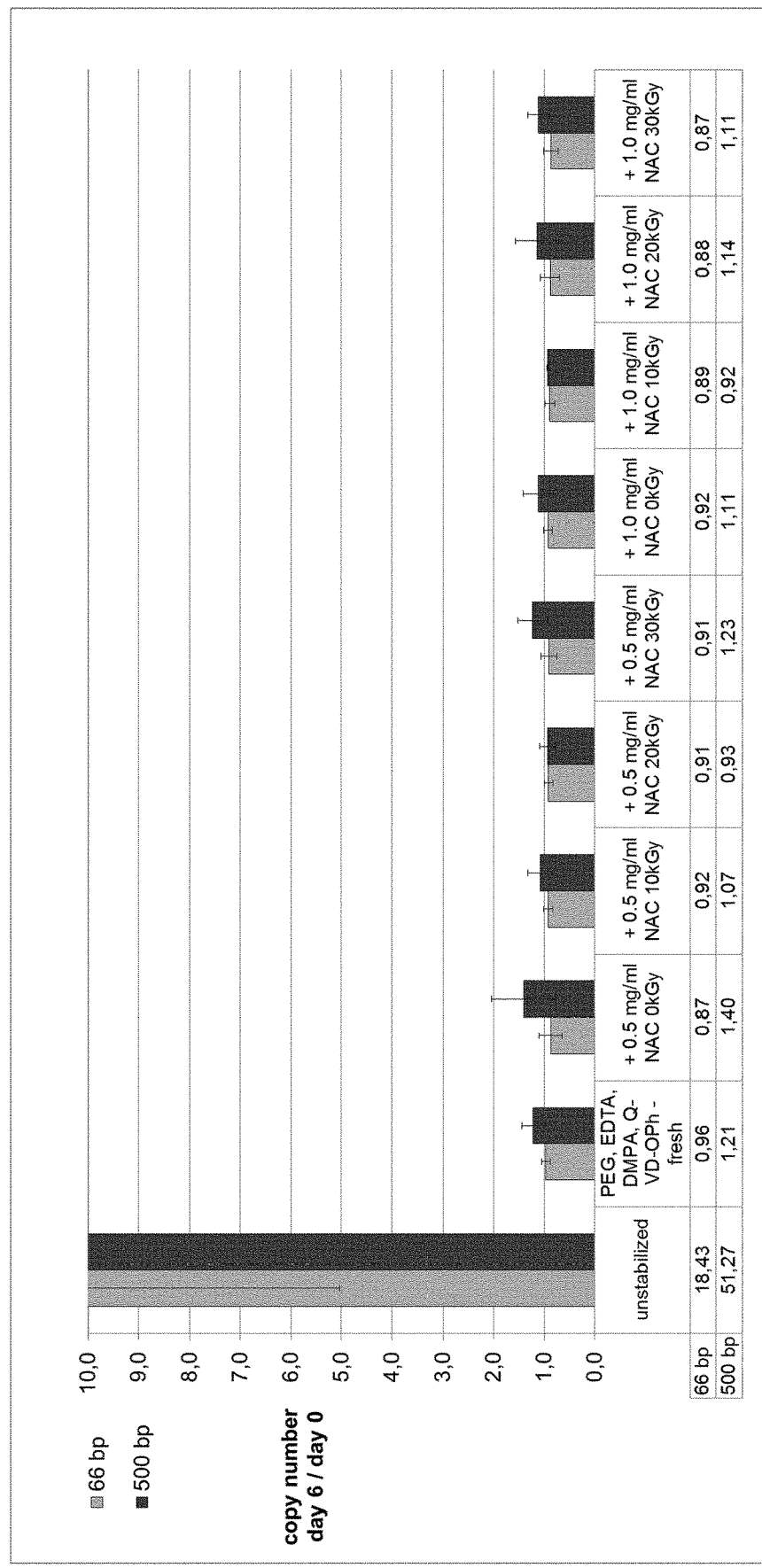

FIG. 8A, 8B: Addition of N-acetyl-cysteine to the stabilization reagent and the effect of increasing doses of gamma irradiation on ccfDNA level in plasma. Average change and standard deviation of copy numbers (x fold change) of 66 bp and 500 bp fragments of the 18S rDNA gene in non-stabilized EDTA blood (left) and in stabilized blood samples drawn into tubes with 0.5, 1.0, 2.0 and 4.0 mg/ml N-acetyl-cysteine; non-sterile or sterilized with different doses of gamma irradiation; ccfDNA levels were determined after storage of the stabilized samples.

Figure 9:
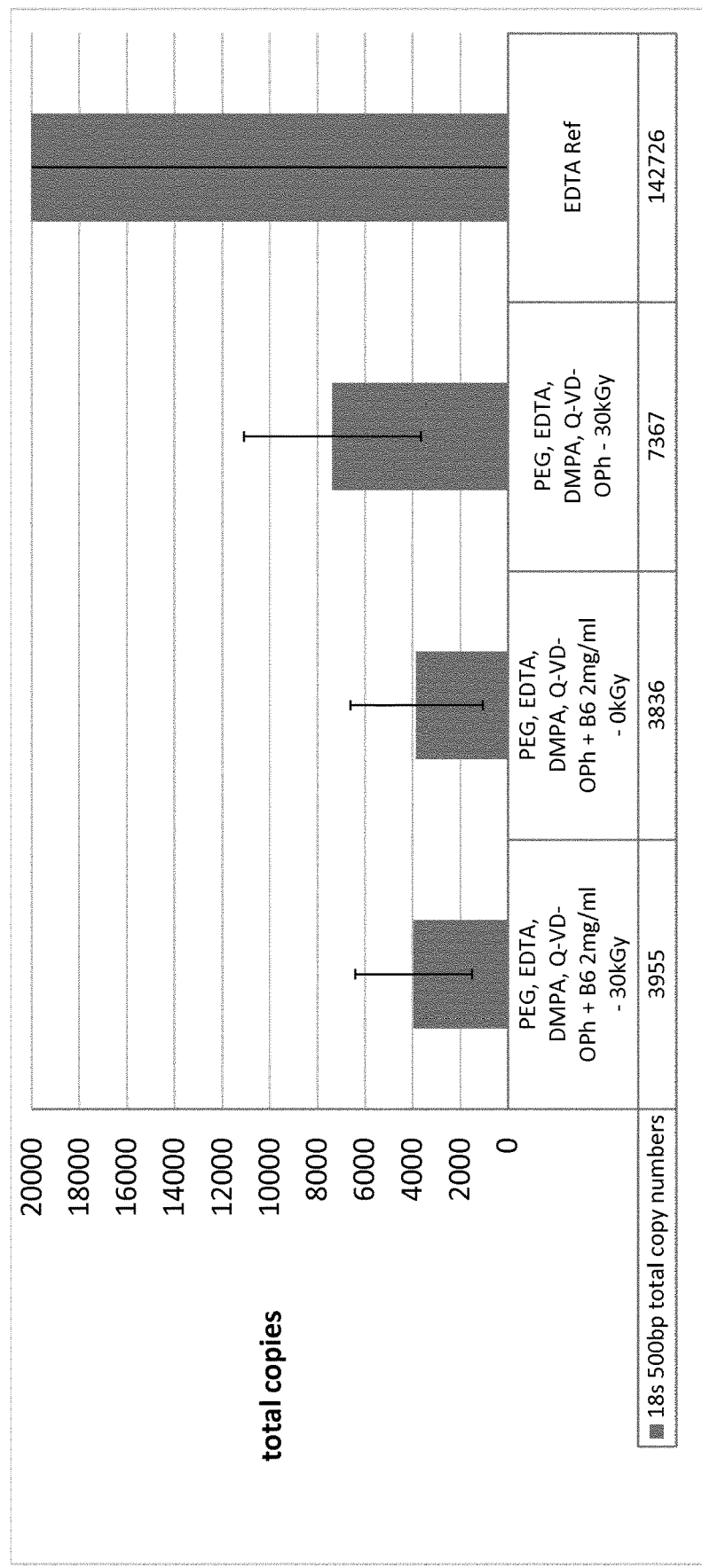

FIG. 9: Mean average total copy numbers of 500 bp fragment of the 18S rDNA gene in blood samples from 8 donors stored for 5 days at room temperature. Blood samples were stabilized with stabilization reagents with (left bar) or without (third bar from left) vitamin B6 as scavenger. These stabilization reagents had been sterilized. As controls, a stabilization reagent with vitamin B6 but that had not been sterilized (second bar from left) and unstabilized EDTA blood (fourth bar from left) were included.

Figure 10:
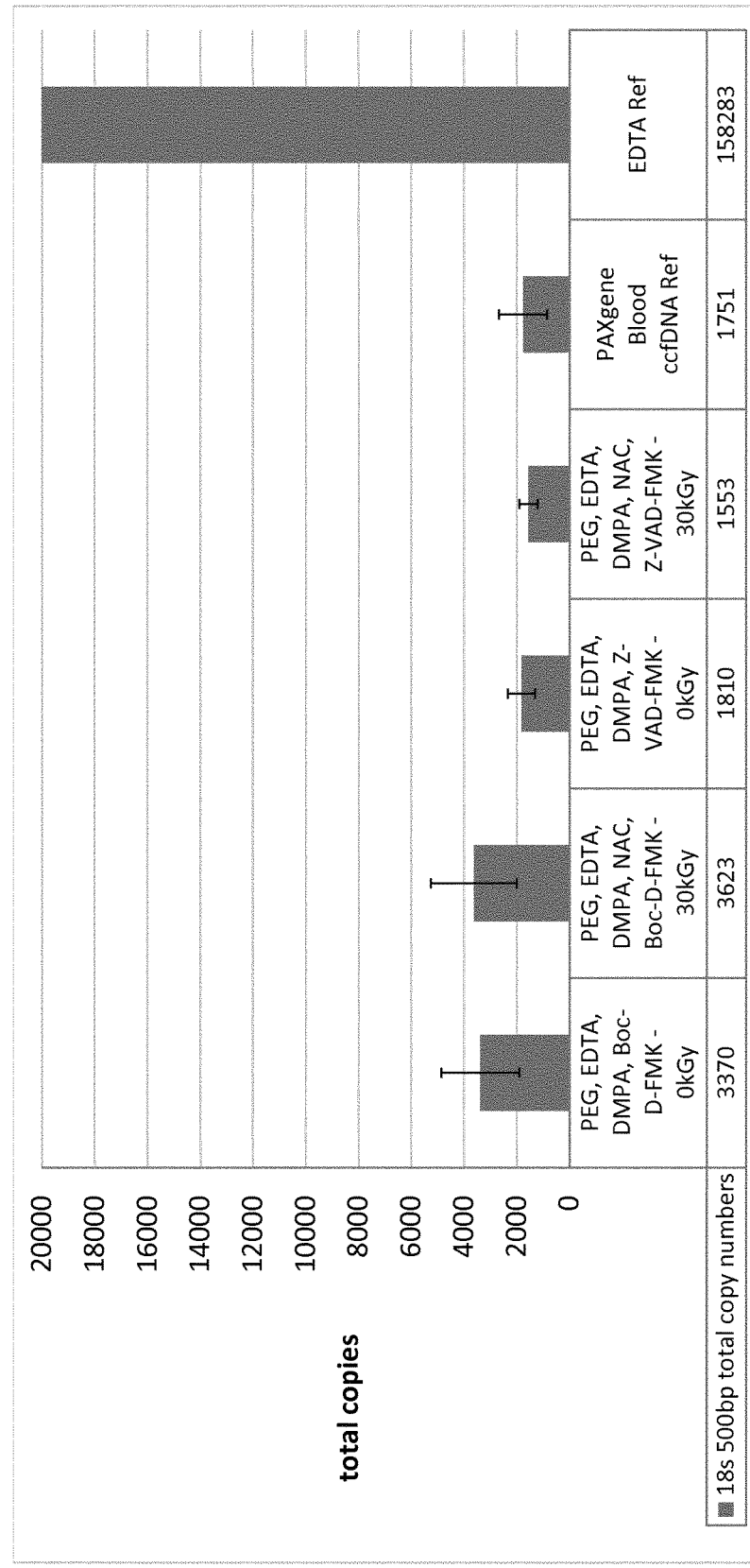

FIG. 10: Mean average total copy numbers of 500 bp fragment of the 18S rDNA gene in blood samples from 6 donors stored for 5 days at room temperature. Blood samples were stabilized with stabilization reagents comprising different caspase inhibitors. Left bar: stabilization reagent comprising the caspase inhibitor Boc-D-(OMe)-FMK (non-sterilized); second bar from left: stabilization reagent comprising the caspase inhibitor Boc-D-(OMe)-FMK and N-acetyl-cysteine as scavenger (sterilized); third bar from left: stabilization reagent comprising the caspase inhibitor Z-VAD (OMe)-FMK (non-sterilized); fourth bar from left: stabilization reagent comprising the caspase inhibitor Z-VAD (OMe)-FMK and N-acetyl-cysteine as scavenger (sterilized); fifth bar from left: PAXgene Blood ccfDNA Tube; sixth bar from left: unstabilized EDTA blood.

DETAILED DESCRIPTION OF THE INVENTION

Providing a sterilized composition suitable for stabilizing an extracellular nucleic acid population, in particular a ccfDNA population, of a biological sample is desirable for a number of reasons, as set out above. The same applies regarding stabilizing compositions that are additionally suitable for stabilizing intracellular nucleic acids such as intracellular DNA (e.g. genomic DNA) and/or intracellular RNA and which are in particular suitable for stabilizing the gene expression profile. Without wishing to be bound by theory, the present inventors have found that sterilization by irradiation, in particular gamma irradiation, can lead to degradation of a main component of the stabilization reagent, the caspase inhibitor. Depending on the irradiation energy and time, up to 95% of the caspase inhibitor may degrade during the sterilization process. Degradation of the caspase inhibitor during sterilization leads to a loss of performance of the stabilization composition. This effect can be seen in the examples by the increased release of genomic DNA from blood cells when using such a sterilized stabilization composition for stabilizing blood samples. Thus, a method was needed to prevent that one or more active ingredients within a stabilization composition comprising one or more caspase inhibitors, such as in particular the caspase inhibitor, become substantially degraded during the sterilization process involving irradiation, in particular during sterilization by gamma irradiation.

The present inventors have found that only certain compounds are able to protect the stabilization composition during sterilization involving irradiation, such as sterilization by gamma irradiation. These compounds include thioalcohols such as in particular N-acetyl-cysteine and glutathione (in particular in reduced form), water-soluble vitamins such as ascorbic acid, and vitamin E or a derivative thereof, such as trolox. Of the numerous compound candidates tested, only these compounds were found to protect the caspase inhibitor comprised in the stabilization composition (and optionally other degradation sensitive components) from substantial degradation during sterilization by irradiation without negatively affecting the stabilizing performance of the stabilization composition. This advantageous combination of effects is shown in the examples for the stabilization of the ccfDNA population in blood samples. For ease of reference, thioalcohols, such as in particular N-acetyl-cysteine and glutathione (in particular in reduced form), water-soluble vitamins such as ascorbic acid, and vitamin E or a derivative thereof, such as trolox sometimes are collectively referred to herein as "the compounds of the invention".

Other compounds, such as tannic acid and gallic acid, known to act as radical scavengers in e.g. pharmaceutical compositions, were found to interfere with the stabilizing performance of a caspase inhibitor containing composition suitable for stabilizing an extracellular nucleic acid population after sterilization. Thus, the obtained sterilized composition comprising these compounds was unsuitable to stabilize the extracellular nucleic acid population in a sample. Also, other compounds described in the art to act as radical scavengers, such as mannitol, isopropanol or Tween-80, were not found to mediate appropriate radioprotection for a caspase inhibitor containing compositions suitable for stabilizing an extracellular nucleic acid population comprised in a biological sample.

As it is demonstrated by the examples, the protective effect mediated by the compounds of the invention is attained for a broad range of sterilization conditions and a broad range of irradiation doses. Advantageously, the compounds are effective at a mildly acid pH, and it is advantageously not required to revert to strongly acidic or basic pH conditions during sterilization.

Thus, the present inventors have found that a caspase inhibitor containing composition that is suitable for stabilizing an extracellular nucleic acid population of a biological sample can be efficiently protected against degradation during sterilization by including prior to sterilization at least one of the compounds of the invention into the composition. It is surprisingly possible to add these protective compounds essentially without adversely affecting the performance of the compositions in stabilizing an extracellular nucleic acid population. The resulting sterilized compositions also allow for downstream applications such as isolation and/or analysis of the contained stabilized extracellular nucleic acid population. The same applies regarding caspase inhibitor containing stabilizing compositions that are additionally suitable for stabilizing intracellular nucleic acids such as intracellular DNA and/or intracellular RNA and which are in particular suitable for stabilizing the gene expression profile. The present invention thereby makes an important contribution to the art.

A most preferred compound for use in the present invention is N-acetyl-cysteine. It offers excellent protection during sterilization, such as sterilization by irradiation, in particular gamma irradiation. At the same time, it does not interfere with the stabilizing properties and in particular the performance of the stabilization compositions on ccfDNA stabilization as it is demonstrated in the examples.

A. Method for Producing a Sterilized Composition

The above findings can advantageously be applied in a method for producing a sterilized composition suitable for stabilizing an extracellular nucleic acid population of a biological sample comprising one or more caspase inhibitors.

Therefore, according to a first aspect, the present invention provides a method of producing a sterilized composition suitable for stabilizing an extracellular nucleic acid population of a biological sample, the method comprising:
  a) providing a composition comprising:
    i. at least one caspase inhibitor, and
    ii. at least one compound selected from a thioalcohol (that is preferably N-acetyl-cysteine or glutathione), a water-soluble vitamin, and vitamin E or a derivative thereof; and
  b) irradiating the composition for sterilization.

The term "extracellular nucleic acids" or "extracellular nucleic acid" as used herein, in particular refers to nucleic acids that are not contained in cells. Respective extracellular nucleic acids are also often referred to as cell-free nucleic acids. These terms are used as synonyms herein. Hence, extracellular nucleic acids usually are present exterior of a cell or exterior of a plurality of cells within a sample. The term "extracellular nucleic acids" refers e.g. to extracellular RNA as well as to extracellular DNA. Examples of typical extracellular nucleic acids that are found in the cell-free fraction (respectively portion) of biological samples such as e.g. body fluids include but are not limited to mammalian extracellular nucleic acids such as e.g. extracellular tumor-associated or tumor-derived DNA and/or RNA, other extracellular disease-related DNA and/or RNA, epigenetically modified DNA, fetal DNA and/or RNA, small interfering RNA such as e.g. miRNA and siRNA, and non-mammalian extracellular nucleic acids such as e.g. viral nucleic acids, pathogen nucleic acids released into the extracellular nucleic acid population e.g. from prokaryotes (e.g. bacteria), viruses, eukaryotic parasites or fungi. The extracellular nucleic acid population usually comprises certain amounts of intracellular nucleic acids that were released from damaged or dying cells. E.g. the extracellular nucleic acid population present in blood usually comprises intracellular globin mRNA that was released from damaged or dying cells. This is a natural process that occurs in vivo. Such intracellular nucleic acid present in the extracellular nucleic acid population can even serve the purpose of a control in a subsequent nucleic acid detection method. The stabilization methods described in the aforementioned applications in particular reduce the risk that the amount of intracellular nucleic acids, such as genomic DNA, that is comprised in the extracellular nucleic acid population is significantly increased after the cell-containing sample was collected due to the ex vivo handling of the sample. Thus, alterations of the extracellular nucleic acid population because of the ex vivo handling are reduced and can even be prevented. Herein, reference is made to extracellular nucleic acids that are obtained from a circulating body fluid such as blood or lymphatic fluid as circulating extracellular nucleic acids or circulating cell-free nucleic acids. As used herein, the term extracellular nucleic acids in particular can refer to mammalian extracellular nucleic acids. Examples include but are not limited to disease-associated or disease-derived extracellular nucleic acids such e.g. as tumor-associated or tumor-derived extracellular nucleic acids, extracellular nucleic acids released due to inflammations, necrosis or injuries, in particular traumata, extracellular nucleic acids related to and/or released due to other diseases, or extracellular nucleic acids derived from a fetus. The stabilization of ccfDNA and thus a ccfDNA population is particularly preferred. The term "extracellular nucleic acids" or "extracellular nucleic acid" as described herein also refers to extracellular nucleic acids obtained from other cell-containing biological samples, in particular biological samples other than body fluids. Usually, a sample comprises more than one kind or type of extracellular nucleic acids.

The term "extracellular nucleic acid population" as used herein in particular refers to the collective of different extracellular nucleic acids that are comprised in a cell-containing sample. A cell-containing sample usually comprises a characteristic and thus unique extracellular nucleic acid population. Thus, the type, kind, ratio and/or the amount of one or more extracellular nucleic acids comprised in the extracellular nucleic acid population of a specific sample may be important sample characteristics. According to one embodiment, the extracellular nucleic acid population refers to extracellular DNA, in particular cell free circulating DNA. As discussed above, it is important to stabilize and thus to substantially preserve said extracellular nucleic acid population at the state wherein the sample is collected, as its composition and/or the amount of one or more extracellular nucleic acids comprised in the extracellular nucleic acid population of a sample can provide valuable medical, prognostic or diagnostic information. Therefore, it is advantageous if the profile of the extracellular nucleic acid population is efficiently stabilized over the intended stabilization period. The stabilization technologies described herein reduce contaminations and hence a dilution of the extracellular nucleic acid population by intracellular nucleic acids, in particular by genomic DNA, after sample collection and stabilization. Thus, a substantial preservation of the extracellular nucleic acid population is achieved. As is shown by the examples, changes in the extracellular nucleic acid population—here shown for the extracellular DNA population—with respect to the quantity, the quality and/or the composition of the comprised extracellular nucleic acids, in particular changes attributable to an increase of released genomic DNA, are over the stabilization period considerably reduced compared when using a stabilization composition comprising a caspase inhibitor as described herein compared to an unstabilized sample or a corresponding sample that is e.g. stabilized by EDTA in case of a blood sample or a sample derived from blood. According to one embodiment the increase in genomic DNA from $T_0$ (stabilization point) to an end of the stabilization period (preferably 48 h, 72 h or 96 h after $T_0$) is reduced by at least 60%, at least 70%, at least 75%, at least 80%, at least 85%, at least 90% or at least 95% compared to an unstabilized sample or a corresponding sample that is e.g. stabilized by EDTA in case of a blood sample (e.g. 1.5 mg EDTA/ml stabilized blood sample) or a sample derived from blood.

In embodiments, the provided sterilized composition is furthermore suitable for stabilizing intracellular nucleic acids, such as intracellular DNA (e.g. genomic DNA) and/or intracellular RNA. In particular, it can be suitable for stabilizing the gene expression profile of contained cells, thereby allowing the reliable profiling of gene expression. By stabilizing and thus preserving the gene transcription profile of contained cells, changes in the gene expression profile are reduced or even prevented during the stabilization period. Therefore, sterilized stabilization compositions are provided that allow the separate analysis of the extracellular and intracellular nucleic acid population in the stabilized sample if desired.

In embodiments, the sterilized stabilizing composition also enables the analysis of cells contained in the stabilized sample, by stabilizing the cells comprised in the biological sample so that they remain substantially intact. The stabilization of cell properties such as e.g. cell surface characteristics and/or the cell morphology is advantageous. It allows analysing and also separating specific cells contained in the stabilized sample such as e.g. blood cells or circulating tumor cells contained in a blood sample.

The biological sample can be a cell-containing biological sample or a biological sample suspected to contain cells. The biological sample can be selected from the group consisting of body fluids and cell-containing samples derived from body fluids. Examples include but are not limited to whole blood, samples derived from blood such as plasma or serum, buffy coat, urine, sputum, lachrymal fluid, lymphatic fluid, amniotic fluid, sweat, liquor, cerebrospinal fluid, ascites, milk, stool, bronchial lavage, saliva, amniotic fluid, nasal secretions, vaginal secretions, semen/seminal fluid, wound secretions, cell culture and swab samples. According to one embodiment, the cell-containing biological sample is a body fluid, a body secretion or body excretion, preferably a body fluid, most preferably urine, lymphatic fluid, blood, buffy coat, plasma or serum. In particular, the cell-containing biological sample can be a circulating body fluid such as blood or lymphatic fluid. Preferably, the cell-containing biological sample is a blood sample, sometimes also referred to whole blood. The blood sample preferably has not been diluted or fractionated prior to stabilization. According to one embodiment, the blood sample is peripheral blood. Also preferably the biological sample can be plasma or serum. According to one embodiment, the cell-containing biological sample was obtained from a human. The cell-containing biological sample comprises or is suspected to comprise extracellular nucleic acids in the extracellular portion of the sample.

It should be understood that in the method according to the first aspect of the invention, the composition provided in step a) and irradiated in step b) has not yet been contacted with a biological sample to be stabilized. It is the stabilization composition as such, i.e. the reagent without the biological sample, that is irradiated for sterilization. Accordingly, the composition provided in step a) and irradiated in step b) has not yet been contacted with a biological sample and hence, does not comprise a biological sample in steps a) and b). Hence, the composition provided in step a) and irradiated in step b) does not comprise cells and/or cell fragments. Thus, the composition provided in step a) and irradiated in step b) does not comprise body fluids and/or cell-containing samples derived from body fluids.

This method will now be described in more detail. In doing so, steps a) and b) of the method will first be described. When discussing step a), emphasis will be put on further describing the advantageous compounds according to feature ii. of step a). Then, exemplary compositions provided, e.g. prepared in step a) will be further described.

Step a), Providing a Composition

Step a) encompasses providing a composition comprising at least one caspase inhibitor, and at least one compound selected from a thioalcohol (preferably N-acetyl-cysteine and/or glutathione), a water-soluble vitamin, and vitamin E or a derivative thereof. Such composition can be produced and thus prepared using the method according to the fifth aspect.

The provided caspase inhibitor containing composition is suitable for stabilizing an extracellular nucleic acid population, in particular ccfDNA, of a biological sample. Further additives that can be additionally included in the composition to enhance the stabilization effect are known to the skilled person and are also described herein.

The form of the composition provided in step a) is not particularly limited. For example, the composition can be provided in a solid form. If desired, the composition can be provided in lyophilized form. In case the composition is provided, e.g. prepared in a solid form, it can be modified so as to provide a liquid composition prior to performing method step b). For example, the solid composition can be dissolved in a liquid prior to irradiation to provide for irradiation step b) a liquid composition which preferably is an aqueous composition.

It is preferred that the composition provided in step a) is in a liquid form. Preferably, the composition is prepared in an aqueous form. For example the components of the composition can be contacted, preferably mixed with an appropriate solvent, to yield a liquid composition. The liquid composition preferably is an aqueous composition. Water can be used as solvent.

Provided or prepared in a "liquid form" as used herein can in particular mean that a liquid composition is provided or prepared. The liquid composition may be a homogenous mixture of only one phase but it is also within the scope of the present invention that a liquid composition comprises solid components such as e.g. precipitates. Provided or prepared in an "aqueous form" as used herein can in particular mean that an aqueous liquid composition is provided or prepared. An "aqueous" composition comprises water. According to one embodiment, an "aqueous" composition comprises water as the major ingredient (% v/v).

Without wishing to be bound by theory, the preparation of a liquid, in particular aqueous, composition offers several advantages when used for stabilizing an extracellular nucleic acid population in a biological sample. A liquid composition allows e.g. a rapid and convenient admixture with liquid samples comprising or being suspected of comprising extracellular nucleic acids to be stabilized. Examples for liquid samples are blood samples, plasma samples and serum samples. Also, preparing a stabilization composition that contains water is particularly preferred when stabilizing a blood sample, as this embodiment significantly reduces hemolysis. Hence preparing a stabilization composition that contains water provides advantages when said stabilization composition subsequently is used for stabilizing a blood sample.

The components of the composition prepared in step a) can be comprised, respectively can be dissolved, in a solvent, e.g. water, or a buffered liquid, e.g. comprising a biological buffer such as MOPS, TRIS, PBS and the like. Furthermore, the components of the stabilization composition may be dissolved in or the stabilization composition may comprise a polar aprotic solvent such as dimethyl sulfoxide (DMSO). DMSO was also found to support the protection of the stabilization composition during sterilization conferred by the compounds of the invention, in particular when used in combination with vitamin E or derivative thereof, such as trolox.

With the present method, it is possible to protect the caspase inhibitor contained in the stabilization composition during the sterilization process that involves irradiation. This advantageously also at mild pH conditions. It is not required to revert to strongly acidic or strongly basis pH conditions. The at least one compound selected from a thioalcohol (which preferably is N-acetyl-cysteine and/or glutathione), a water-soluble vitamin, and vitamin E or a derivative thereof are active under mild pH conditions. This includes the use of ascorbic acid for protection. Using mild pH conditions, such as mildly acidic conditions, is advantageous because it prevents precipitation of single components of the stabilization reagent at lower temperature particularly well. Thereby, also an even more rapid admixture with liquid samples is possible, which contributes to reduce hemolysis and thus improve the stabilization effect. Preferably, the composition has a mildly acidic pH.

According to one embodiment, the stabilization composition provided in step a) has a pH selected from a pH of 4.0 to 7.0, a pH of 4.1 to 6.9, a pH of 4.2 to 6.8, a pH of 4.3 to 6.6, a pH of 4.4 to 6.3, a pH of 4.5 to 6.0, or a pH of 4.5 to 5.5.

According to one embodiment, the composition is provided in a sample collection device, or the composition is filled into a sample collection device prior to performing irradiation step b). The sample collection device can be a device according to the seventh aspect of the invention. The sample collection device is suitable for sterilization involving irradiation.

Feature 4 at Least One Caspase Inhibitor

The stabilization composition provided in step a) comprises at least one caspase inhibitor.

The caspase inhibitor can be a caspase inhibitor as described in WO 2013/045457 A1 or WO 2013/045458 A1. The caspase inhibitors disclosed therein are incorporated herein by reference. As it is described in these prior art documents, a caspase inhibitor is alone and also in combination with other stabilizing agents highly effective in stabilizing the extracellular nucleic acid population (e.g. extracellular DNA) of a biological sample, such as e.g. a blood sample.

Preferably, the caspase inhibitor is cell-permeable. Members of the caspase gene family play a significant role in apoptosis. The substrate preferences or specificities of individual caspases have been exploited for the development of peptides that successfully compete caspase binding. It is possible to generate reversible or irreversible inhibitors of caspase activation by coupling caspase-specific peptides to e.g. aldehyde, nitrile or ketone compounds. E.g. fluoromethyl ketone (FMK) derivatized peptides such as Z-VAD-FMK act as effective irreversible inhibitors with no added cytotoxic effects. Inhibitors synthesized with a benzyloxycarbonyl group (BOC) at the N-terminus and O-methyl side chains exhibit enhanced cellular permeability. Further suitable caspase inhibitors are synthesized with a phenoxy group at the C-terminus. An example is Q-VD-OPh which is a cell permeable, irreversible broad-spectrum caspase inhibitor that is even more effective in preventing apoptosis and thus supporting the stabilization than the caspase inhibitor Z-VAD-FMK.

According to one embodiment, the caspase inhibitor is a pancaspase inhibitor and thus is a broad spectrum caspase inhibitor. According to one embodiment, the caspase inhibitor comprises or consists of peptides or proteins. According to one embodiment, the caspase inhibitor comprises a modified caspase-specific peptide. Preferably, said caspase-specific peptide is modified by an aldehyde, nitrile or ketone compound. According to one embodiment, the caspase specific peptide is modified, preferably at the carboxyl terminus, with an O-Phenoxy (OPh) or a fluoromethyl ketone (FMK) group. Suitable caspase inhibitors comprising or consisting of proteins or peptides, and caspase inhibitors comprising modified caspase-specific peptides are disclosed in Table 1 of WO 2013/045457, and are incorporated herein by reference. The table provides examples of suitable caspase inhibitors. Without wishing to be bound by theory, it is believed that the compounds of the invention are inter alia active to protect a caspase inhibitors that comprise a peptide and in particular caspase inhibitors that are peptides modified by functional groups. The compounds of the invention are in particular suitable to protect a peptidic caspase inhibitor that is modified, preferably at the carboxyl terminus, with an O-Phenoxy (OPh) group and/or is modified, preferably at the N-terminus, with a glutamine (Q) group. An example of such a caspase inhibitor is Q-VD-OPh.

According to one embodiment, the caspase inhibitor is selected from the group consisting of Q-VD-OPh, Z-VAD(OMe)-FMK and Boc-D-(OMe)-FMK. According to one embodiment, the caspase inhibitor is selected from the group consisting of Q-VD-OPh and Z-VAD(OMe)-FMK. In a preferred embodiment, Q-VD-OPh, which is a broad spectrum inhibitor for caspases, is used for stabilization. Q-VD-OPh is cell permeable and inhibits cell death by apoptosis. Q-VD-OPh is not toxic to cells even at extremely high concentrations and comprises a carboxy terminal phenoxy group conjugated to the amino acids valine and aspartate. It is equally effective in preventing apoptosis mediated by the three major apoptotic pathways, caspase-9 and caspase-3, caspase-8 and caspase-10, and caspase-12 (Caserta et al., 2003).

As shown in the examples, the compounds of the invention are effective over a wide concentration range and protect a caspase inhibitor contained in the stabilization composition during irradiation. Within the concentration ranges tested for the protective compounds of the invention, protection was achieved over a wide range of caspase inhibitor concentrations comprised in the stabilization composition, and the degree of protection conferred was largely independent from the caspase inhibitor concentration tested.

The stabilization composition comprises one or more caspase inhibitors, in particular a caspase inhibitor comprising a modified caspase-specific peptide such as Q-VD-OPh, in an amount sufficient to yield a stabilization effect on the extracellular nucleic acid population that is contained in the biological sample. According to one embodiment, the stabilization composition comprises the caspase inhibitor in a concentration to yield a final concentration of 0.1 µM to 25 µM, 0.5 µM to 20 µM, 1 µM to 17 µM, 2 µM to 16 µM, more preferred 3 µM to 15 µM of caspase inhibitor after the stabilization composition has been contacted with the intended volume of the sample to be stabilized. As can be seen from the examples, final concentrations of about 5 µM, about 10 µM and about 15 µM were found to be well suitable. As was also explained above, albeit it here is referred to concentrations that yield a final concentration of caspase inhibitor after the stabilization composition has been contacted with the intended volume of the sample to be stabilized, it should be understood that in the method according to the first aspect of the invention, the composition provided in step a) and irradiated in step b) has not yet been contacted with a biological sample to be stabilized.

According to one embodiment, the stabilization composition and hence the stabilization reagent comprises the caspase inhibitor in a concentration selected from 0.35 µg/ml to 70 µg/ml, 0.7 µg/ml to 63 µg/ml, 1.74 µg/ml to 59 µg/ml, 10.5 µg/ml to 56 µg/ml, or 15 µg/ml to 50 µg/ml, 20 µg/ml to 45 µg/ml, 25 µg/ml to 40 µg/ml and 30 µg/ml to 38 µg/ml. The concentration can be selected from 0.7 µg/ml to 45 µg/ml and 1.74 µg/ml to 40 µg/ml.

According to one embodiment, the stabilization composition and hence the stabilization reagent comprises the caspase inhibitor in a concentration selected from 0.68 µM to 136 µM, 1.36 µM to 122.5 µM, 3.38 µM to 114.72 µM, 20.4 µM to 109 µM, or 29.2 µM to 97.2 µM, 38.9 µM to 87.5 µM, 48.6 µM to 77.8 µM and 58.3 µM to 74 µM. The concentration can be selected from 20.4 µM to 97.2 µM and 29.2 µM to 87.5 µM.

The above mentioned concentrations of the caspase inhibitor in the mixture comprising the stabilization composition (reagent) and the biological sample to be stabilized and the stabilization composition (reagent) as such apply to the use of a single caspase inhibitor as well as to the use of a combination of caspase inhibitors. The aforementioned concentrations are in particular suitable when using a pan-caspase inhibitor, in particular a modified caspase specific peptide such as Q-VD-OPh and/or Z-VAD(OMe)-FMK. A further example of a modified caspase specific peptide is Boc-D-(OMe)-FMK. The above mentioned concentrations are e.g. suitable for stabilizing blood samples. Suitable concentration ranges for individual caspase inhibitors and/or for other cell-containing biological samples can be determined by the skilled person, e.g. by testing different concentrations of the respective caspase inhibitor in the test assays described in the examples.

Feature ii, at Least One Compound Selected from a Thioalcohol (Preferably N-Acetyl-Cysteine and/or Glutathione), a Water-Soluble Vitamin, and Vitamin E or a Derivative Thereof The composition provided in step a) additionally comprises at least one compound selected from a thioalcohol (which preferably is N-acetyl-cysteine or glutathione), a water-soluble vitamin, and vitamin E or a derivative thereof. The composition therefore can be sterilized by irradiation (such as by gamma irradiation), wherein the sterilized composition essentially maintains its stabilization properties and hence performance. Without wishing to be bound by theory, these compounds help to protect the stabilization compositions to be irradiated, especially the caspase inhibitor(s) comprised therein. At the same time these compounds do not interfere with the stabilization effects, thereby ensuring functionality of the compositions in stabilizing extracellular nucleic acid populations, such as in particular ccfDNA. It was surprising that the compounds of the present invention achieve these balanced effects. As is shown in the examples, a number of other radical scavengers did not confer protection against irradiation and/or interfered with the stabilizing performance of the compositions and thus were unsuitable.

The at least one compound comprised in the stabilization composition can be selected from N-acetyl-cysteine, glutathione, preferably glutathione in reduced form, ascorbic acid, a B vitamin, and/or a water soluble vitamin E derivative. The at least one compound comprised in the stabilization composition can be selected from N-acetyl-cysteine, glutathione, preferably glutathione in reduced form, ascorbic acid, and/or a water soluble vitamin E derivative. Preferably, the at least one compound is selected from N-acetyl-cysteine, glutathione, preferably glutathione in reduced form, ascorbic acid, and/or trolox. More preferably, the at least one compound is selected from N-acetyl-cysteine, glutathione, preferably glutathione in reduced form, vitamin B6 and/or ascorbic acid. More preferably, the at least one compound is selected from N-acetyl-cysteine, glutathione, preferably glutathione in reduced form, and/or ascorbic acid. N-acetyl-cysteine and ascorbic acid have been found to be particularly effective, as was glutathione, in particular in reduced form. Vitamin B6 was likewise found useful. N-acetyl-cysteine is most preferred according to the present invention.

As shown in the examples, the compounds of the invention can be comprised in the composition and are effective in a broad concentration range.

According to one embodiment, the stabilization composition comprises at least one compound selected from a thioalcohol (which preferably is N-acetyl-cysteine and/or glutathione (preferably in reduced form)), a water-soluble vitamin, and vitamin E or a derivative thereof in a concentration of less than 20 mg/ml, preferably 15 mg/ml or less, 10 mg/ml or less, 12 mg/ml or less, 7 mg/ml or less, 3 mg/ml or less, 1.5 mg/ml or less or 0.75 mg/ml or less. Preferably, the composition comprises at least 0.05 mg/ml, at least 0.1 mg/ml, at least 0.2 mg/ml or at least 0.3 mg/ml of the at least one compound. According to one embodiment, the composition comprises at least one compound selected from N-acetyl-cysteine, glutathione (preferably in reduced form), ascorbic acid, a B vitamin, such as vitamin B6, and trolox in these concentrations. According to one embodiment, the composition comprises at least one compound selected from N-acetyl-cysteine, glutathione (preferably in reduced form), ascorbic acid and trolox in these concentrations.

The at least one compound of the invention can be comprised in a concentration so that at least 15%, at least 20%, at least 35%, or at least 50% of the caspase inhibitor comprised in the stabilization composition prior to sterilization by irradiation is present in the stabilizing composition after the sterilization. Preferably, the at least one compound of the invention is comprised in a concentration so that at least 60%, at least 70%, at least 80%, or at least 90%, more preferably at least 80%, of the caspase inhibitor comprised in the stabilization composition prior to sterilization by irradiation is present in the stabilization composition after sterilization. This can be determined e.g. using HPLC analysis as it was done in the examples. As the examples show, the degree of degradation of the caspase inhibitor and the percentage of caspase inhibitor that is still present in non-degraded form after irradiation depends on the irradiation dose. Exemplary compound concentrations for achieving a desired percentage of caspase inhibitor remaining after irradiation with a given irradiation dose are also shown in the examples.

The at least one compounds of the invention can be comprised in a concentration in which it can exert a protective effect on the caspase inhibitor during sterilization as defined above, while at the same time not substantially interfering with the stabilization properties of the stabilization composition. According to one embodiment, the stabilizing effect of the stabilization composition comprising the protective compound of the invention is at least 80%, at least 85%, at least 90%, at least 95%, at least 97% or 100% of an otherwise identical composition not comprising the protective compound. The stabilizing effect may even be increased by the addition of the protective compound. For example, the stabilizing effect of the stabilization composition comprising the protective compound of the invention can be 120%, 115%, 110% or 105% of an otherwise identical composition not comprising the protective compound. Preferably, the stabilization composition comprising the protective compound of the invention and the otherwise identical composition not comprising the protective compound are compared with one another in non-sterilized or non-irradiated form. Tests for determining the stabilization properties of stabilizing compositions with and without a compound of interest are provided in the examples and are described in the experimental procedures section therein. Extracellular nucleic acids in a sample can be quantified using a real time PCR assay and the described increase in copy numbers over time can be used to determine the stabilizing effect of a given stabilization composition. Accordingly, the stabilizing effect of a given stabilization composition can in one embodiment be determined by determining the ratio of total ccfDNA at day 0 directly after blood draw and after storage for e.g. 6 days at room temperature, as described in the examples.

According to one embodiment, the at least one compound of the invention is comprised in a concentration in which it can exert a protective effect on the caspase inhibitor during sterilization as defined above, while at the same time not substantially reducing the amount of extracellular nucleic acids of interest detectable in a stabilized sample. In one embodiment, at least 50%, at least 60%, at least 70%, at least 80%, at least 90%, at least 95% or 100% of extracellular nucleic acids of interest that are detected in a sample stabilized with an otherwise identical composition, but not comprising the protective compound, are detected when stabilizing the sample with a composition comprising the protective compound. The amount of extracellular nucleic acids can be determined e.g. as shown in the examples, using real-time PCR and determining the absolute copy number.

Also provided and encompassed is the preparation of a composition that comprises more than one of the compounds of the invention. In this case, the composition can comprise each contained compound in a concentration as indicated above. Alternatively, the concentrations as indicated above refer to the overall concentration of all compounds of the invention that are comprised in the composition. Suitable concentrations for individual compounds and combinations of compounds can be determined by the skilled person following the technical information that is provided herein. As shown in the examples, combining compounds of the invention can further improve the protection of the stabilization composition during sterilization compared to the use of the individual compounds. This advantageous effect tended to be more pronounced at high irradiation doses, and was achieved already when using comparably low concentrations of each individual compound. The exemplary combinations and concentrations depicted in FIG. 6 and in Table 7 of the Examples are specifically contemplated herein for use.

In case the composition is initially provided in a solid form, the composition can be brought into a liquid form prior to irradiation. The liquid composition can comprise the at least one compound in the aforementioned concentrations. According to this embodiment, the solid composition comprises the one or more compounds of the invention in an amount sufficient to yield upon solvation a liquid composition that comprises said one or more compounds in a concentration as described above and below.

The individual components of the invention that may be contained in the composition for protection will now be explained in further detail.

According to one embodiment, the composition that is provided, e.g. prepared in step a) comprises at least one thioalcohol. A "thioalcohol" or "thiol" as used herein in particular can be a thiol or thioalcohol as defined in Römpp Lexikon Chemie, 10$^{th}$ edition 1999, Georg Thieme Verlag Stuttgart, New York.

Particularly preferred thioalcohols are N-acetyl-cysteine and glutathione. A highly suitable and very preferred component for the purposes of the present invention is N-acetyl-cysteine.

"N-acetyl-cysteine" as used herein preferably is "N-acetyl-L-cysteine". Thus, "N-acetyl-cysteine" as used herein preferably designates the compound "N-acetyl-L-cysteine". Therefore, when reference is made herein to "N-acetyl-cysteine", the respective disclosure also applies for "N-acetyl-L-cysteine", unless context dictates otherwise. Whenever "N-acetyl-cysteine" is mentioned, N-acetyl-L-cysteine is preferred. N-acetyl-D-cysteine can also be used. N-acetyl-cysteine, like glutathione, is a thioalcohol. As used herein, "N-acetyl-cysteine" can in particular be N-acetyl-cysteine as defined in Pschyrembel Klinisches Wörterbuch (258. Auflage, Walter de Gruyter, Berlin, N.Y., 1998).

N-acetyl-cysteine has been found to efficiently protect a stabilization composition comprising one or more caspase inhibitors, in particular comprising a caspase inhibitor comprising a modified caspase-specific peptide such as Q-VD-OPh, during sterilization by irradiation, such as gamma irradiation. At the same time, N-acetyl-cysteine advantageously does not substantially interfere with the stabilization of an extracellular nucleic acid population, such as ccfDNA. Accordingly, in a preferred embodiment, the stabilization composition comprises N-acetyl-cysteine. N-acetyl-cysteine furthermore allows for a mild pH of the stabilization composition, such as a mildly acidic pH. Suitable pH values were described above. Advantageously, the stabilization compositions comprising N-acetyl-cysteine can be irradiated and sterilized in a liquid form, including an aqueous form. It was advantageously not required to irradiate the compositions in solid or frozen form to maintain the stabilization performance of the caspase inhibitor containing composition.

The stabilization composition can comprise N-acetyl-cysteine in a concentration of 0.05 mg/ml to 15 mg/ml, 0.1 mg/ml to 10 mg/ml, 0.1 mg/ml to 7.5 mg/ml, 0.1 mg/ml to 5 mg/ml, or 0.1 mg/ml to 2 mg/ml. Preferably, the composition comprises at least 0.2 mg/ml, or at least 0.3 mg/ml N-acetyl-cysteine. A compositions comprising 0.2 mg/ml to 1 mg/ml, or 0.3 mg/ml to 0.8 mg/ml is particularly preferred.

The stabilization composition can comprise N-acetyl-cysteine in a concentration of 0.05 mg/ml to 15 mg/ml, 0.1 mg/ml to 10 mg/ml, 0.1 mg/ml to 7.5 mg/ml, 0.1 mg/ml to 5 mg/ml, 0.1 mg/ml to 2 mg/ml, 0.2 mg/ml to 1 mg/ml, or 0.3 mg/ml to 0.8 mg/ml and be irradiated for sterilization in a liquid, preferably aqueous, form.

N-acetyl-cysteine has been found to provide a particularly good protection of the one or more caspase inhibitors comprised in the stabilization composition while at the same time ensuring a good performance of the stabilization composition in downstream applications. The aforementioned N-acetyl-cysteine concentrations work well, and yield particularly good results. As shown in the examples, N-acetyl-cysteine at all concentrations tested (0.5 mg/ml, 1 mg/ml, 2 mg/ml, 4 mg/ml and 10 mg/ml) conferred excellent protection of the stabilization composition during irradiation. At the same time, N-acetyl-cysteine even in higher concentrations did not interfere with the performance of the stabilization composition in subsequent applications.

An N-acetyl-cysteine concentration of 0.2 mg/ml to 1 mg/ml or 0.3 mg/ml to 0.8 mg/ml in the caspase inhibitor containing composition is particularly preferred. It was found that such a composition provides upon sterilization an irradiated/sterilized stabilization composition with particularly good storage properties. In particular, an excellent stability at the end of shelf life was observed. Using these concentrations, the shelf-life of the sterilized stabilization composition can be prolonged advantageously.

According to one embodiment, the stabilization composition comprises N-acetyl-cysteine and optionally one or more compounds selected from glutathione, a water-soluble vitamin, and vitamin E or a derivative thereof. According to one embodiment, the stabilization composition comprises N-acetyl-cysteine and can further comprise one or more of glutathione, preferably glutathione in reduced form, ascorbic acid, a B vitamin, preferably vitamin B6, and water soluble vitamin E derivative, preferably trolox. In particular, the composition can comprise N-acetyl-cysteine and can further comprise one or more of glutathione, preferably glutathione in reduced form, ascorbic acid, and water soluble vitamin E derivative, preferably trolox. Thus, it is also contemplated that the stabilization composition of step a) comprises N-acetyl-cysteine and further comprises glutathione, preferably glutathione in reduced form, and/or ascorbic acid. According to one embodiment, the composition comprises N-acetyl-cysteine and ascorbic acid. According to one embodiment, the composition comprises N-acetyl-cysteine and glutathione, preferably glutathione in reduced form. Albeit all of the aforementioned combinations have been found very useful for protecting the stabilization composition comprising one or more caspase inhibitors to be sterilized by irradiation, also N-acetyl-cysteine alone was found to yield excellent results. Combinations of N-acetyl-cysteine and a B vitamin such as in particular vitamin B6 are also contemplated.

According to one embodiment, the stabilization composition provided in step a) comprises glutathione. The thio-alcohol glutathione, in particular glutathione in reduced form, is as shown in the examples also suitable to protect the composition during sterilization by irradiation, essentially without negatively effecting the stabilization properties of the caspase inhibitor containing composition. Glutathione exists in both reduced and oxidized forms. In the reduced form, the thiol group of cysteine comprised in the compound is able to donate a reducing equivalent. "Glutathione" as used herein can in particular be glutathione as defined in Pschyrembel Klinisches Wörterbuch (258. Auflage, Walter de Gruyter, Berlin, N.Y., 1998).

The composition can comprise glutathione, preferably glutathione in reduced form, in a concentration of 0.03 mg/ml to 10 mg/ml, 0.04 mg/ml to 7.5 mg/ml, 0.075 mg/ml to 5 mg/ml, 0.15 mg/ml to 4 mg/ml, 0.3 mg/ml to 3 mg, 0.4 mg/ml to 2 mg/ml, or 0.4 mg/ml to 1.3 mg/ml. The composition can comprise glutathione, preferably glutathione in reduced form, in a concentration of 0.03 mg/ml to 10 mg/ml, 0.04 mg/ml to 7.5 mg/ml, 0.075 mg/ml to 5 mg/ml, 0.15 mg/ml to 4 mg/ml, 0.3 mg/ml to 3 mg, 0.4 mg/ml to 2 mg/ml, or 0.4 mg/ml to 1.3 mg/ml and can be irradiated in a liquid, preferably aqueous, form.

The skilled person will understand that the amount of reduced glutathione in the stabilization composition may be reduced after irradiation and/or sterilization, as parts or all of the glutathione may be oxidized during this process. Thus, the concentrations for glutathione in reduced form indicated above in particular refer to the concentration in the composition prior to irradiation for sterilization.

As shown in the examples, glutathione, in particular glutathione in reduced form, is very effective in protecting stabilization compositions comprising one or more caspase inhibitors. The reduced form of glutathione conveys a particularly good protective effect on the stabilization composition. Comparably low concentrations and mild pH conditions, in particular mildly acidic conditions, can be used in this embodiment. Advantageously, it was possible to irradiate and sterilize the compositions in liquid form. It was not required to irradiate the compositions in solid or frozen form to maintain the stabilization performance of the compositions. As shown in the examples, a protective effect on the caspase inhibitor was observed for a glutathione concentration as low as 0.05 mg/ml. A more pronounced effect was observed for slightly higher concentrations, such as at least 0.1 mg/ml or at least 0.2 mg/ml. Concentrations of 0.5 mg/ml and 1 mg/ml yielded particularly good results.

As shown in the examples, also water-soluble vitamins such as ascorbic acid are active in protecting stabilization compositions comprising one or more caspase inhibitors. The examples furthermore show that the water-soluble vitamin B6 is active in protecting stabilization compositions comprising one or more caspase inhibitors. Accordingly, a stabilization composition can be provided in step a) that comprises at least one water-soluble vitamin for protection. Derivatives of water-soluble vitamins are likewise contemplated herein and can be used. "Derivatives of water-soluble vitamins" as used herein can in particular be derivatives that like the respective vitamin have activity as radical scavengers. The water-soluble vitamin is in one embodiment selected from vitamin C and a B vitamin. The water-soluble vitamin is in one embodiment selected from ascorbic acid and a B vitamin. In embodiments, the B vitamin is vitamin B6. Vitamin B6 as used herein in particular refers to pyridoxine. Thus, any disclosure presented herein for "vitamin B6" in general specifically applies and refers to the embodiment pyridoxine. Thus, all disclosures described in this application for vitamin B6 in general specifically apply and particularly refer to the preferred embodiment pyridoxine even if not explicitly stated. In embodiments, vitamin B6 can be selected from pyridoxine, pyridoxal, pyridoxamine and/or pyridoxalphosphate.

The water-soluble vitamin can be selected from ascorbic acid, thiamin (vitamin B1), riboflavin (vitamin B2), niacin (vitamin B3), pyridoxine (vitamin B6), folate or folic acid, vitamin B12 (cobalamin), biotin and pantothenic acid.

Preferred is the use of ascorbic acid as water-soluble vitamin. Ascorbic acid can be represented by the following formula:

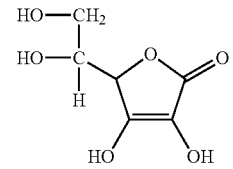

"Ascorbic acid" as used herein can encompass stereoisomers, such as L-ascorbic acid, D-ascorbic acid, L-isoascorbic acid, D-isoascorbic acid. "Ascorbic acid" as used herein can in particular be ascorbic acid as defined in as defined in Pschyrembel Klinisches Wörterbuch (258. Auflage, Walter de Gruyter, Berlin, N.Y., 1998). It will be understood that derivatives of ascorbic acid are likewise contemplated and can be used herein. "Derivatives of ascorbic acid" as used herein can in particular be derivatives that like the ascorbic acid have activity as radical scavengers.

For ease of reading, in the following, reference is made to "water-soluble vitamins" without explicitly referring also to derivatives thereof. Also, reference is made to "ascorbic acid" without explicit reference to derivatives of ascorbic acid. However, the disclosure in relation with water-soluble vitamins (for example regarding concentration ranges) throughout also applies for the derivatives of water-soluble vitamins unless context dictates otherwise, and the disclosure for ascorbic acid (for example regarding concentration ranges) throughout also applies for the derivatives of ascorbic acid unless context dictates otherwise.

The stabilization composition can comprise at least one water-soluble vitamin, preferably selected from ascorbic acid, vitamin B1, vitamin B2, vitamin B3, vitamin B6, folate or folic acid, vitamin B12, biotin and pantothenic acid, more preferably ascorbic acid, in a concentration of less than 20 mg/ml, such as 0.1 mg/ml to 15 mg/ml, 0.2 mg/ml to 14 mg/ml, 0.5 mg/ml to 13.5 mg/ml, 1 mg/ml to 13 mg/ml, 1.5 mg/ml to 12 mg/ml, or 2 mg/ml to 11 mg/ml. In embodiments, the stabilization composition comprises a B vitamin such as vitamin B6 in one of the aforementioned concentrations. In particular, the B vitamin which preferably is vitamin B6 can be comprised e.g. in a concentration of 0.1 mg/ml to 15 mg/ml or 0.1 mg/ml to 14 mg/ml. Vitamin B6 was found to protect the stabilization composition comprising at least one caspase inhibitor during sterilization already at comparably low concentrations such as a concentration of about 2 mg/ml. Hence, B vitamins and in particular vitamin B6 can be used also at comparably low concentrations of e.g. 0.1 mg/ml to 11 mg/ml, 0.2 mg/ml to 7.5 mg/ml or even 0.2 mg/ml to 2 mg/ml. Using a B vitamin such as vitamin B6 at an according low concentration also is more economical.

The composition can comprise at least one water-soluble vitamin, preferably selected from ascorbic acid, vitamin B1, vitamin B2, vitamin B3, vitamin B6, folate or folic acid, vitamin B12, biotin and pantothenic acid, more preferably ascorbic acid, in a concentration of less than 20 mg/ml, such as 0.1 mg/ml to 15 mg/ml, 0.2 mg/ml to 14 mg/ml, 0.5 mg/ml to 13.5 mg/ml, 1 mg/ml to 13 mg/ml, 1.5 mg/ml to 12 mg/ml, or 2 mg/ml to 11 mg/ml and can be irradiated in a liquid, preferably aqueous, form for sterilization. In embodiments, the stabilization composition comprises a B vitamin such as vitamin B6 in one of the aforementioned concentrations. In particular, the B vitamin which preferably is vitamin B6 can be comprised e.g. in a concentration of 0.1 mg/ml to 15 mg/ml, 0.1 mg/ml to 14 mg/ml, 0.1 mg/ml to 11 mg/ml, 0.2 mg/ml to 7.5 mg/ml or 0.2 mg/ml to 2 mg/ml.

The stabilization composition can comprise ascorbic acid a concentration of less than 20 mg/ml, such as 0.1 mg/ml to 15 mg/ml, 0.2 mg/ml to 14 mg/ml, 0.5 mg/ml to 13.5 mg/ml, 1 mg/ml to 13 mg/ml, 1.5 mg/ml to 12 mg/ml, or 2 mg/ml to 11 mg/ml.

The composition can comprise ascorbic acid a concentration of less than 20 mg/ml, such as 0.1 mg/ml to 15 mg/ml, 0.2 mg/ml to 14 mg/ml, 0.5 mg/ml to 13.5 mg/ml, 1 mg/ml to 13 mg/ml, 1.5 mg/ml to 12 mg/ml, or 2 mg/ml to 11 mg/ml and be irradiated for sterilization in a liquid, preferably aqueous, form.

As shown in the examples, numerous concentrations of e.g. 1 mg/ml, 2 mg/ml, 5 mg/ml and 10 mg/ml ascorbic acid were found to protect the stabilization composition comprising at least one caspase inhibitor during sterilization over a wide range of irradiation doses applied. Within the concentrations tested, the protective effect tended to increase with increasing ascorbic acid concentrations. It was most pronounced at concentrations of about 5 mg/ml to about 10 mg/ml. Albeit ascorbic acid has been found to protect the stabilization composition during sterilization when used over a wide concentration range, it is preferred that concentrations of less than 20 mg/ml ascorbic acid are used. Particularly suitable concentrations of ascorbic acid are those ranging from 0.5 mg/ml to 15 mg/ml, such as 2 mg/ml to 11 mg/ml (e.g. 2, 4 or 5 mg/ml) indicated above. It was found that surprisingly, ascorbic acid is protective at these comparably low concentrations, which advantageously also allow to employ ascorbic acid at a mild pH, such as a mildly acidic pH. Advantageously, it was possible to irradiate and sterilize the compositions in liquid form. It was surprisingly not required to irradiate the compositions in a solid or frozen form to maintain the stabilization performance of the compositions. Moreover, using ascorbic acid in a concentration of less than 20 mg/ml, preferably 15 mg/ml or less advantageously prevents inhibitory effects of ascorbic acid on the stabilization of ccfDNA in plasma.

Figure 6:
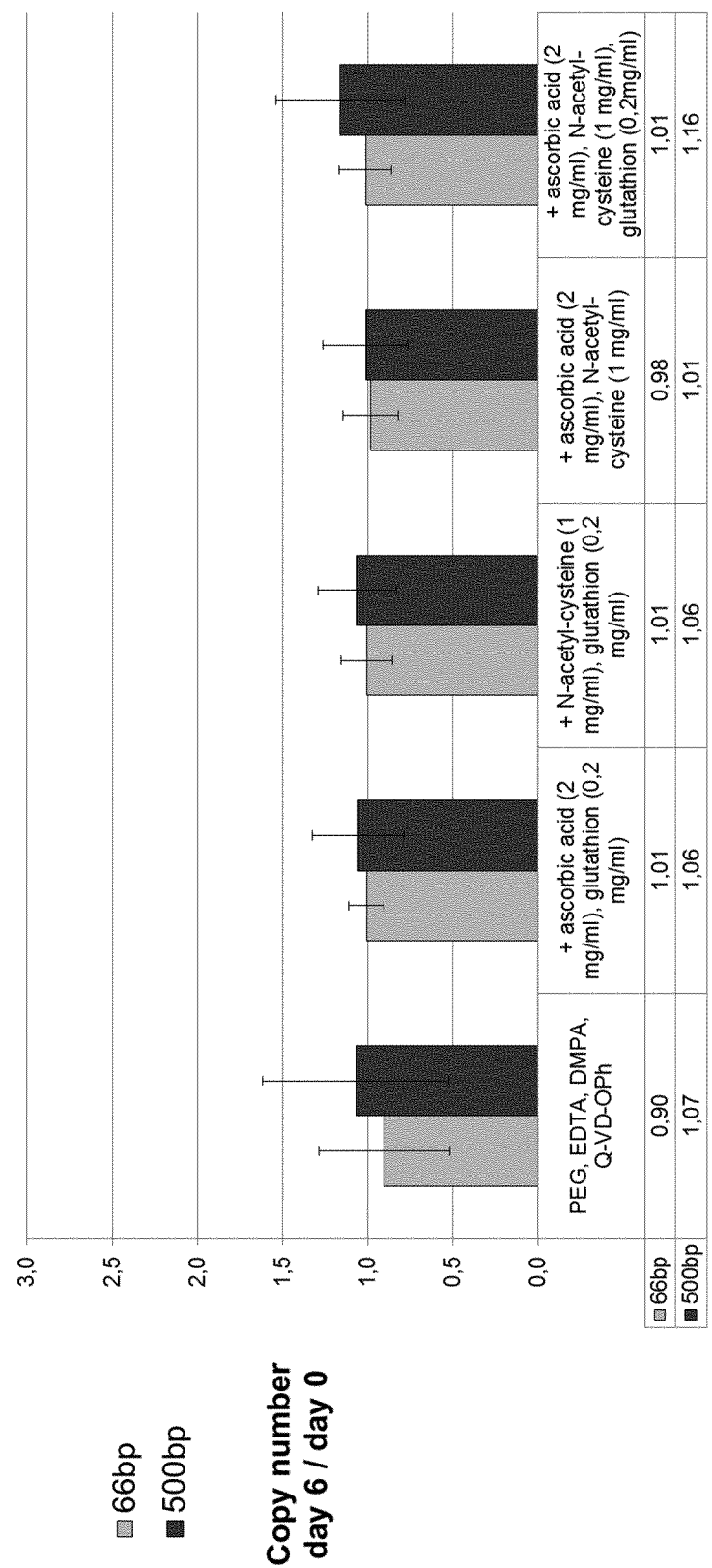
FIG. 6: Addition of different combinations of ascorbic acid, N-acetyl-cysteine and glutathione to the caspase inhibitor containing stabilization composition. Average change of copy numbers (x fold change) of 66 bp and 500 bp fragments of the 18S rDNA gene in stabilized blood after storage.

The composition can comprise ascorbic acid in combination with one or more further compounds of the invention. As explained when discussing N-acetyl-cysteine, the caspase inhibitor comprising composition can for example comprise ascorbic acid and N-acetyl-cysteine for protection. Likewise the composition can comprise ascorbic acid and glutathione, preferably glutathione in reduced form. Exemplary combinations are shown in FIG. 6 and in the examples in Table 7 and are specifically contemplated herein.

As shown in the examples, also vitamin E and derivatives thereof provide a protective effect on stabilization compositions comprising one or more caspase inhibitors during sterilization by irradiation. Vitamin E and derivatives thereof, in particular water soluble derivatives such as trolox, likewise show protective activity, albeit the extent of protection mediated by e.g. trolox was lower than that observed for N-acetyl-cysteine, ascorbic acid or glutathione. Water-soluble derivatives of other fat-soluble vitamins, such as water-soluble derivatives of vitamin D, K and A, are also contemplated herein; the derivatives in particular can have activity as a radical scavenger, like the respective fat-soluble vitamin.

"Vitamine E" as used herein can in particular be vitamine E as defined in Pschyrembel Klinisches Wörterbuch (258. Auflage, Walter de Gruyter, Berlin, N.Y., 1998). "Derivatives of vitamin E" as used herein can in particular be derivatives that like vitamin E have activity as radical scavengers. "Derivatives of vitamin E" as used herein can in particular be water-soluble derivatives of vitamin E that have activity as radical scavengers. One particularly preferred example of a water-soluble vitamin E derivative is trolox. Trolox can be designated as 6-hydroxy-2,5,7,8-tetramethylchromane-2-carboxylic acid.

Accordingly, a composition can be prepared that comprises vitamin E or a derivative thereof. The composition can comprise a water-soluble vitamin E derivative. Preferably, the water-soluble vitamin E derivative is trolox. In the application throughout, the disclosure in relation with "Vitamin E or a derivative thereof" in particular applies for water-soluble vitamin E derivatives including trolox, unless context dictates otherwise. Whenever "vitamin E or a derivative thereof" is referred to, a water-soluble vitamin E derivative, such as in particular trolox, is preferred.

Vitamin E or a derivative thereof, such as preferably a water-soluble vitamin E derivative, more preferably trolox, can in particular be employed in the stabilizing composition in a concentration of 0.5 mg/ml to 5 mg/ml, 0.6 mg/ml to 4 mg/ml, 0.75 mg/ml to 3 mg/ml, 0.9 mg/ml to 2 mg/ml, or 1 mg/ml to 1.4 mg/ml. Thus, the composition can for example comprise trolox in a concentration of 0.5 mg/ml to 5 mg/ml, 0.6 mg/ml to 4 mg/ml, 0.75 mg/ml to 3 mg/ml, 0.9 mg/ml to 2 mg/ml, or 1 mg/ml to 1.4 mg/ml.

The composition comprising at least one caspase inhibitor can comprise vitamin E or a derivative thereof, preferably a water-soluble vitamin E derivative, more preferably trolox, in a concentration of 0.5 mg/ml to 5 mg/ml, 0.6 mg/ml to 4 mg/ml, 0.75 mg/ml to 3 mg/ml, 0.9 mg/ml to 2 mg/ml, or 1 mg/ml to 1.4 mg/ml and be irradiated for sterilization in a liquid, preferably aqueous, form.

The composition can comprise a water-soluble vitamin E derivative, preferably trolox, in a concentration of 0.5 mg/ml to 5 mg/ml, 0.6 mg/ml to 4 mg/ml, 0.75 mg/ml to 3 mg/ml, 0.9 mg/ml to 2 mg/ml, or 1 mg/ml to 1.4 mg/ml and be irradiated for sterilization in a liquid, preferably aqueous, form. Concentrations of about 1.25 mg/ml of a vitamin E derivative were found to confer protection of the stabilization composition during irradiation, as shown in the examples. There, the vitamin E derivative trolox has been tested.

The concentrations and concentration ranges disclosed herein for the respective compounds can also be used when combining more than one compound. For example, ranges according to Table A below can be used when combining more than one compound. Exemplary combinations and concentration ranges for N-acetyl-cysteine, glutathione and ascorbic acid are shown in FIG. 6 and in Table 7 of the examples and are specifically contemplated herein. As can be seen from the examples, already comparably low concentrations of the individual compounds are protective during sterilization by irradiation when being used in combination. Therefore, e.g. concentrations of about 0.3 mg/ml to 4 mg/ml can be used for each of N-acetyl-cysteine and ascorbic acid, and a concentration range of e.g. about 0.1 mg/ml to 1.3 mg/ml can be used for glutathione when combining one or more of these compounds.

Exemplary preferred compounds of the invention comprised in the stabilization composition provided in step a) and advantageous concentration ranges are disclosed in the below table.

TABLE A

| Compound | range 1 (mg/ml) | range 2 (mg/ml) |
|---|---|---|
| N-acetyl-cysteine | 0.05-15 | 0.3-0.8 |
| Ascorbic acid | 0.1-15 | 2-11 |
| Glutathione (preferably reduced) | 0.03-10 | 0.4-1.3 |
| Trolox | 0.5-5 | 1-1.4 |

Exemplary preferred compounds of the invention comprised in the stabilization composition provided in step a) and advantageous concentration ranges are also disclosed in the below table.

TABLE B

| Compound | range 1 (mg/ml) | range 2 (mg/ml) |
|---|---|---|
| N-acetyl-cysteine | 0.05-15 | 0.3-0.8 |
| Ascorbic acid | 0.1-15 | 2-11 |
| Glutathione (preferably reduced) | 0.03-10 | 0.4-1.3 |
| Trolox | 0.5-5 | 1-1.4 |
| Vitamin B6 | 0.1-11 | 0.2-2 |

Further Characteristics of the Composition Prepared or Provided in Step a)

The stabilization composition provided in step a) may comprise additional components besides the at least one caspase inhibitor and the at least one compound selected from a thioalcohol (which preferably is N-acetyl-cysteine or glutathione), a water-soluble vitamin, and vitamin E or a derivative thereof as discussed above. These additional components may in particular be included to support the stabilization effect on the extracellular nucleic acid population.

Further components that may be comprised and advantageous compositions that can be provided, e.g. prepared in step a) are described below. Of course, preferred embodiments discussed above in particular in relation with features i. and ii. apply and the headlines and subsections provided herein only serve to facilitate reading.

Advantageous compositions suitable for stabilizing an extracellular nucleic acid population comprising one or more caspase inhibitors are disclosed in WO 2013/045457 A1, WO 2014/146780 A1, WO 2014/146782 A1, PCT/EP2015/055699, WO 2014/049022 A1, WO 2013/045458 A1 and WO 2014/146781 A1. These references to which it is referred describe several stabilization compositions for stabilizing an extracellular nucleic acid population. The extracellular nucleic acid stabilization effect of the described stabilization compositions is based on the use of either the caspase inhibitor or one or more further compounds that can be used in conjunction with a caspase inhibitor for stabilization. WO2014/049022 and WO2014/146781 also teach caspase inhibitor containing stabilizing compositions suitable for stabilizing intracellular nucleic acids (such as intracellular DNA and/or intracellular RNA, in particular suitable for stabilizing the gene expression profile). Furthermore, these applications disclose stabilizing compositions which allow the subsequent analysis of the stabilized cells, such as the cell morphology and/or cell surface characteristics. The stabilization compositions described in these references that comprise one or more caspase inhibitors disclosed therein are incorporated herein by reference, and stabilization compositions described in PCT/EP2015/055699 are particularly preferred. These caspase inhibitor containing compositions can be sterilized with the method of the invention. Accordingly, it preferred that in step a), a composition as disclosed in one of the aforementioned references that comprises one or more caspase inhibitors is provided, wherein the composition further comprises at least one compound selected from a thioalcohol (preferably N-acetyl-cysteine or glutathione, preferably wherein the glutathione is in reduced form), a water-soluble vitamin, and vitamin E or a derivative thereof, N-acetyl-cysteine being highly preferred. The same applies if combining a stabilizing composition as disclosed in WO 2008/145710 (which allows to stabilize e.g. the genome, transcriptome and proteome) with a caspase inhibitor to provide a caspase-inhibitor containing composition, wherein the composition further comprises as described at least one compound selected from a thioalcohol (preferably N-acetyl-cysteine or glutathione, preferably wherein the glutathione is in reduced form), a water-soluble vitamin, and vitamin E or a derivative thereof, N-acetyl-cysteine being highly preferred.

The stabilization composition provided, e.g. prepared in step a) accordingly can further comprise one or more of:
  a) an anticoagulant and/or a chelating agent;
  b) a poly(oxyethylene) polymer; and/or
  c) at least one primary, secondary or tertiary amide.

Suitable concentrations for anticoagulants, chelating agents, poly(oxyethylene) polymers and primary, secondary and tertiary amides are disclosed in PCT/EP2015/055699.

Subsequently, exemplary suitable concentrations of the individual agents, if present in the stabilization composition, are indicated.

The stabilization composition can be a liquid. The indicated concentrations are particularly preferred for the stabilisation of blood samples. E.g. a liquid stabilisation composition of 0.5 ml to 2.5 ml, 0.5 ml to 2 ml, preferably 1 ml to 2 ml or 1 ml to 1.5 ml can be used. Such stabilization composition comprising the stabilizing agents in the concentrations indicated below, can be used for stabilizing e.g. 10 ml blood.

For example, the composition can further comprise an anticoagulant, preferably a chelating agent, more preferably EDTA such as $K_2$EDTA. This embodiment is particularly useful in case the sample to be stabilized is blood. According to one embodiment, said composition comprises an anticoagulant or chelating agent, preferably EDTA, in a concentration selected from 9.5 mM to 1100 mM, 20 mM to 750 mM, 50 mM to 600 mM, 75 mM to 550 mM, 100 mM to 500 mM, 125 mM to 450 mM, 130 mM to 300 mM and 140 mM to 250 mM. According to one embodiment, the concentration is from 100 mM to 250 mM.

In one embodiment, the composition provided in step a) comprises at least one poly(oxyethylene) polymer. As it is described in detail in PCT/EP2015/055699 to which it is referred, poly(oxyethylene) polymers exhibit advantageous stabilization properties when intending to stabilize extracellular nucleic acids. They are in particular effective when being used in combination with a caspase inhibitor and can improve the stabilization effect. Therefore, it is advantageous that the stabilization composition to be sterilized additionally includes a poly(oxyethylene) polymer. This composition may have one or more of the following characteristics:
  a) the poly(oxyethylene) polymer is a polyethylene glycol, preferably an unsubstituted polyethylene glycol;
  b) the composition comprises a poly(oxyethylene) polymer which is a high molecular weight poly(oxyethylene) polymer having a molecular weight of at least 1500;
  c) the composition comprises at least one poly(oxyethylene) polymer having a molecular weight below 1500, preferably a low molecular weight poly(oxyethylene) polymer having a molecular weight of 1000 or less, more preferably the molecular weight lies in a range selected from 100 to 800, 150 to 700, 200 to 600 and 200 to 500;
  d) the composition comprises a poly(oxyethylene) polymer which is a high molecular weight poly(oxyethylene) polymer having a molecular weight of at least 1500 and at least one further poly(oxyethylene) polymer that is at least 100, preferably at least 200, at least 300 or at least 400 below the molecular weight of the a high molecular weight poly(oxyethylene) polymer, wherein said further poly(oxyethylene) polymer preferably is a low molecular weight poly(oxyethylene) polymer having a molecular weight of 1000 or less; and/or
  e) the composition comprises a poly(oxyethylene) polymer which is a high molecular weight poly(oxyethylene) polymer and a poly(oxyethylene) polymer which is a low molecular weight poly(oxyethylene) polymer, wherein said high molecular weight poly(oxyethylene) polymer has a molecular weight that lies in a range selected from 1500 to 50000, 1500 to 40000, 2000 to 30000, 2500 to 25000, 3000 to 20000, 3500 to 15000 and 4000 to 12500 and/or wherein said low molecular weight poly(oxyethylene) polymer has a molecular weight of 1000 or less and wherein preferably, the molecular weight lies in a range selected from 100 to 1000, 150 to 800, 150 to 700, 200 to 600, 200 to 500 and 200 to 400.

According to one embodiment, the stabilization composition comprises a high molecular weight poly(oxyethylene) polymer which preferably is a polyethylene glycol in a concentration selected from 0.4% to 35% (w/v), 0.8% to 25% (w/v), 1.5% to 20% (w/v), 2.5% to 17.5% (w/v), 3% to 15% (w/v), 4% to 10% (w/v) and 3% to 5% (w/v). Suitable concentrations can be determined by the skilled person and may inter alia depend on whether the high molecular weight poly(oxyethylene)glycol is used as alone or in combination with a further poly(oxyethylene) polymer such as a low poly(oxyethylene) polymer and the amount, e.g. the volume, of the stabilization composition used to stabilize a certain amount of cell-containing sample. Examples of concentration ranges suitable when using a high molecular weight poly(oxyethylene) polymer alone include but are not limited to concentrations selected from 2.2% to 33.0% (w/v), 4.4% to 22.0 (w/v) %, 6.6% to 16.5% (w/v) and 8.8% to 13.2% (w/v). Examples of concentration ranges suitable when using a high molecular weight poly(oxyethylene) polymer in combination with a low molecular weight poly(oxyethylene) polymer include but are not limited to concentrations selected from 0.4% to 30.7%, 0.8% to 15.3%, 1% to 10%, 1.5% to 7.7%, 2.5% to 6%, 3.1% to 5.4% and 3% to 4%.

According to one embodiment, said stabilization composition comprises a low molecular weight poly(oxyethylene) polymer, which preferably is a polyethylene glycol in a concentration selected from 0.8% to 92.0%, 3.8% to 76.7%, 11.5% to 53.7%, 19.2% to 38.3%, 20% to 30% and 20% to 27.5%. According to one embodiment, the concentration is from 11.5% to 30%. The aforementioned concentrations refer to (w/v) or (v/v) depending on whether the low molecular weight poly(oxyethylene) polymer is a liquid or not. As is demonstrated in the examples of PCT/EP2015/055699, low molecular weight poly(oxyethylene) polymers can efficiently support the stabilization of cell-containing samples, in particular when being used in combination with one or more further stabilizing agents as described therein.

According to one embodiment, the stabilization composition prepared or provided in step a) comprises at least one primary, secondary or tertiary amide. Using one or more of these amides support the stabilization of the extracellular nucleic acid population as it is demonstrated in the applications WO 2013/045457 A1, WO 2014/146780 A1, WO 2014/146782 A1, PCT/EP2015/055699, WO 2014/049022 A1, WO 2013/045458 A1 or WO 2014/146781 A1 to which it is referred. WO 2014/049022 and WO 2014/146781 also teach that such amides are suitable for stabilizing intracellular nucleic acids (in particular the gene expression profile). One or more of these amides can be used in addition to the caspase inhibitor for stabilization, preferably in addition to at least one poly(oxyethylene) polymer.

According to one embodiment, the composition accordingly comprises one or more compounds according to formula 1

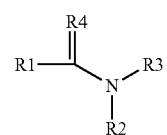

formula 1 wherein R1 is a hydrogen residue or an alkyl residue, preferably a C1-C5 alkyl residue, a C1-C4 alkyl residue or a C1-C3 alkyl residue, more preferred a C1-C2 alkyl residue, R2 and R3 are identical or different and are selected from a hydrogen residue and a hydrocarbon residue, preferably an alkyl residue, with a length of the carbon chain of 1-20 atoms arranged in a linear or branched manner, and R4 is an oxygen, sulphur or selenium residue, preferably R4 is oxygen.

Also a combination of one or more compounds according to formula 1 can be used. In embodiments, wherein R1 is an alkyl residue, a chain length of 1 or 2 is preferred for R1. R2 and/or R3 of the compound according to formula 1 are identical or different and are selected from a hydrogen residue and a hydrocarbon residue, which preferably is an alkyl residue. According to one embodiment, R2 and R3 are both hydrogen. According to one embodiment, one of R2 and R3 is a hydrogen and the other is a hydrocarbon residue. According to one embodiment, R2 and R3 are identical or different hydrocarbon residues. The hydrocarbon residues R2 and/or R3 can be selected independently of one another from the group comprising alkyl, including short chain alkyl and long-chain alkyl, alkenyl, alkoxy, long-chain alkoxy, cycloalkyl, aryl, haloalkyl, alkylsilyl, alkylsilyloxy, alkylene, alkenediyl, arylene, carboxylates and carbonyl (regarding these residues see e.g. WO 2013/045457, p. 20 to 21, herein incorporated by reference). The chain length n of R2 and/or R3 can in particular have the values 1, 2, 3, 4, 5, 6, 7, 8, 9, 10, 11, 12, 13, 14, 15, 16, 17, 18, 19 and 20. According to one embodiment, R2 and R3 have a length of the carbon chain of 1-10, preferably 1 to 5, more preferred 1 to 2. According to one embodiment, R2 and/or R3 are alkyl residues, preferably C1-C5 alkyl residues. Preferably, the compound according to formula 1 is a carboxylic acid amide so that R4 is oxygen. It can be a primary, secondary or tertiary carboxylic acid amide.

According to one embodiment, the compound according to formula 1 is a N,N-dialkyl-carboxylic acid amide. Preferred R1, R2, R3 and R4 groups are described above. Using a respective compound according to formula 1 has the advantage that additionally, intracellular nucleic acids such as in particular RNA, e.g. mRNA and/or miRNA transcripts can be stabilized in the cell-containing sample. The additional stabilization of intracellular nucleic acids, in particular gene transcript levels, is advantageous as it e.g. allows the subsequent analysis of target transcripts or transcript profiles in the contained cells. According to one embodiment, the compound according to formula 1 is selected from the group consisting of N,N-dimethylacetamide, N,N-diethylacetamide, N,N-dimethylformamide and N,N-diethylformamide. Also suitable are the respective thio analogues, which comprise sulphur instead of oxygen as R4. Preferably, at least one compound according to formula 1 is used which is not a toxic agent according to the GHS classification. According to one embodiment, the compound according to formula 1 is a N,N-dialkylpropanamide, such as N,N-dimethylpropanamide.

Also, for example the composition can comprise one or more compounds according to formula 1'

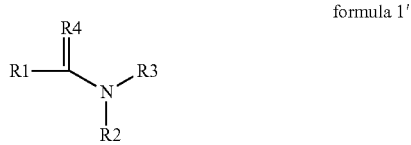

wherein R1 is a hydrogen residue or an alkyl residue, preferably a C1-C5 alkyl residue, more preferred a methyl residue, R2 and R3 are identical or different hydrocarbon residues with a length of the carbon chain of 1-20 atoms arranged in a linear or branched manner, and R4 is an oxygen, sulphur or selenium residue.

Formula 1' is encompassed by Formula 1 discussed above and is compared thereto limited in that R2 and R3 are identical or different hydrocarbon residues (not hydrogen). Otherwise, the residues R1 to R4 correspond to the ones discussed above for Formula 1 and it is referred to the above disclosure which also applies here.

Preferably, the composition comprises butanamide and/or a N,N-dialkylpropanamide, more preferably N,N-dimethlypropanamide.

According to one embodiment, the stabilization composition comprises one or more primary, secondary or tertiary amides in a concentration selected from 0.4% to 38.3%, 0.8% to 23.0%, 2.3% to 11.5%, 3.8% to 9.2%, 5% to 15% and 7.5% to 12.5%. The aforementioned concentrations refer to (w/v) or (v/v) depending on whether the primary, secondary or tertiary amide is a liquid or not. As discussed, primary, secondary or tertiary carboxylic acid amides are preferred.

The composition can further comprise DMSO. For example, the composition can comprise 0.05% to 2.5% (v/v) DMSO, 0.1% to 1.8%, or 0.2% to 1.4% DMSO. DMSO is a suitable solvent and was found to support the protection of the stabilization composition during irradiation, more particular gamma irradiation. This effect was observed in particular when DMSO was used in combination with trolox, but was not limited thereto.

As explained above, the composition can initially be provided in a solid form. It can then be brought into a liquid form prior to irradiation. The solid composition can comprise the caspase inhibitor, one or more compounds of the invention and the optional further components discussed herein in an amount sufficient to yield upon solvation a liquid composition that comprises said caspase inhibitor, said one or more compounds and optional further components in a concentration as described above and below.

According to a non-limiting exemplary embodiment, a solid composition can be prepared that comprises 0.001% to 0.01% (w/w) caspase inhibitor, such as 0.005% to 0.009% (w/w) caspase inhibitor. The composition according to this exemplary embodiment can comprise about 0.05 to about 0.5% (w/w), such as 0.1% to 0.4% (w/w) of a compound of the invention, for example of a thioalcohol, in particular of N-acetyl-cysteine. Further components can be included in the exemplary solid composition, as discussed above and below. Exemplary concentrations for a high molecular weight poly(oxyethylene) polymer, if present, are for example 3.25% to 10% (w/w), such as 5% to 8.5% (w/w). Exemplary concentrations for a low molecular weight poly(oxyethylene) polymer, if present, are for example 20% to 70% (w/w), such as 40% to 65% (w/w). Exemplary concentrations for a primary, secondary or tertiary amide, if present, are for example 15% to 30% (w/w), such as 18% to 25% (w/w). Exemplary concentrations for an anticoagulant and/or a chelating agent, if present, are for example 6% to 24% (w/w), such as 8% to 15% (w/w).

A preferred composition to be sterilized comprises:
a) one or more caspase inhibitors,
b) one or more compound selected from a thioalcohol (which preferably is N-acetyl-cysteine or glutathione), a water-soluble vitamin, and vitamin E or a derivative thereof as discussed above, wherein, preferably, the composition comprises N-acetyl-cysteine, c) at least one poly(oxyethylene) polymer, which preferably is a high molecular weight poly(oxyethylene) polymer having a molecular weight of at least 1500, as stabilizing agent, and optionally one or more, preferably two or more further additives selected from the group consisting of:

d) at least one further poly(oxyethylene) polymer having a molecular weight that is at least 100, preferably at least 200, at least 300 or at least 400 below the molecular weight of the first poly(oxyethylene) polymer, which preferably is a high molecular weight poly(oxyethylene) polymer, wherein said further poly(oxyethylene) polymer preferably is a low molecular weight poly(oxyethylene) polymer having a molecular weight of 1000 or less;

e) at least one primary, secondary or tertiary amide;

f) an anticoagulant and/or a chelating agent.

Preferably, the stabilization composition comprises one or more of the compounds according to the invention in concentrations as disclosed above when discussing feature ii, more preferably as disclosed above in Table A. The stabilization composition can comprise one or more of the compounds as disclosed above in Table B. The use of N-acetyl-cysteine is particularly preferred.

A respective stabilization composition is particularly effective in stabilizing a cell-containing biological sample, such as blood, plasma and/or serum, by stabilizing cells and the extracellular nucleic acid population comprised in said sample. The extracellular nucleic acid population contained in the cell-containing biological sample is substantially preserved over the stabilization period in the state it had shown at the time the biological sample was contacted with said stabilization composition. The release of genomic DNA and other intracellular nucleic acids is significantly reduced as shown e.g. by the present examples and the examples of PCT/EP2015/055699. Extracellular nucleic acids isolated from respectively stabilized samples comprise significantly less contamination with intracellular nucleic acids, in particular fragmented genomic DNA, compared to extracellular nucleic acids that are isolated from unstabilized samples. A respective stabilization composition allows the storage and/or handling, e.g. shipping, of the stabilized sample, e.g. blood, at room temperature for days without substantially compromising the quality of the sample, respectively the extracellular nucleic acid population contained therein.

A further preferred composition to be sterilized comprises:

a) one or more caspase inhibitors, preferably a pancaspase inhibitor, more preferred a caspase inhibitor comprising a modified caspase-specific peptide, even more preferred a caspase inhibitor selected from the group consisting of Q-VD-OPh, Z-VAD(OMe)-FMK and Boc-D-(OMe)-FMK, most preferably Q-VD-OPh;

b) one or more compound selected from a thioalcohol (which preferably is N-acetyl-cysteine or glutathione), a water-soluble vitamin (which preferably is Vitamin B6 or ascorbic acid), and vitamin E or a derivative thereof as discussed above, wherein, preferably, the composition comprises N-acetyl-cysteine, c) at least one poly(oxyethylene) polymer as stabilizing agent, wherein preferably the poly(oxyethylene) polymer is a polyethylene glycol, more preferably an unsubstituted polyethylene glycol;

and optionally one or more, preferably two further additives selected from the group consisting of:

d) at least one primary, secondary or tertiary amide;

e) an anticoagulant and/or a chelating agent.

Preferably, the stabilization composition comprises one or more of the compounds according to the invention in concentrations as disclosed above when discussing feature ii, more preferably as disclosed above in Table A or Table B. The use of N-acetyl-cysteine is particularly preferred.

In embodiments, the at least one poly(oxyethylene) polymer, which preferably is a polyethylene glycol, is selected from a low molecular weight poly(oxyethylene) polymer, preferably a low molecular weight poly(oxyethylene) polymer having a molecular weight of 1000 or less, and/or a high molecular weight poly(oxyethylene) polymer having a molecular weight of at least 1500.

A further example of a preferred stabilization composition with excellent stabilizing and sterilization properties comprises:

a) at least one caspase inhibitor, preferably a pancaspase inhibitor, more preferred a caspase inhibitor comprising a modified caspase-specific peptide, most preferred Q-VD-OPh;

b) N-acetyl-cysteine, glutathione (preferably in reduced form) and/or ascorbic acid, preferably N-acetyl-cysteine, more preferably N-acetyl-cysteine in a concentration of 0.05 mg/ml to 15 mg/ml, 0.1 mg/ml to 10 mg/ml, 0.1 mg/ml to 7.5 mg/ml, 0.1 mg/ml to 5 mg/ml, 0.1 mg/ml to 2 mg/ml, 0.2 mg/ml to 1 mg/ml, or 0.3 mg/ml to 0.8 mg/ml;

c) at least one high molecular weight poly(oxyethylene) polymer having a molecular weight of at least 1500, preferably in a range of 2000 to 40000, more preferred 2500 to 30000, 2500 to 25000 or 3000 to 20000;

d) one or more compounds according to formula 1, preferably wherein the composition comprises butanamide and/or a N,N-dialkylpropanamide, more preferably N,N-dimethlypropanamide;

e) at least one further poly(oxyethylene) polymer having a molecular weight that is at least 100, preferably at least 200, at least 300 or at least 400 below the molecular weight of the high molecular weight poly(oxyethylene) polymer used and wherein said further poly(oxyethylene) polymer preferably is a low molecular weight poly(oxyethylene) having a molecular weight of 1000 or less, preferably having a molecular weight in a range of 200 to 800 or 200 to 600;

f) optionally an anticoagulant and/or a chelating agent, preferably EDTA.

A further example of a preferred stabilization composition with excellent stabilizing and sterilization properties comprises:

a) at least one caspase inhibitor, preferably a pancaspase inhibitor, more preferred a caspase inhibitor comprising a modified caspase-specific peptide, even more preferably a most preferred Q-VD-OPh;

b) N-acetyl-cysteine, glutathione (preferably in reduced form) and/or ascorbic acid, preferably N-acetyl-cysteine, more preferably N-acetyl-cysteine in a concentration of 0.05 mg/ml to 15 mg/ml, 0.1 mg/ml to 10 mg/ml, 0.1 mg/ml to 7.5 mg/ml, 0.1 mg/ml to 5 mg/ml, 0.1 mg/ml to 2 mg/ml, 0.2 mg/ml to 1 mg/ml, or 0.3 mg/ml to 0.8 mg/ml;

c) at least one poly(oxyethylene) polymer as stabilizing agent, wherein preferably the poly(oxyethylene) polymer is a polyethylene glycol, more preferably an unsubstituted polyethylene glycol;

d) one or more compounds according to formula 1, preferably wherein the composition comprises butanamide and/or a N,N-dialkylpropanamide, more preferably N,N-dimethlypropanamide;

e) optionally an anticoagulant and/or a chelating agent, preferably EDTA.

In embodiments, the at least one poly(oxyethylene) polymer, which preferably is a polyethylene glycol, is selected from a low molecular weight poly(oxyethylene) polymer, preferably a low molecular weight poly(oxyethylene) polymer having a molecular weight of 1000 or less, and/or a high molecular weight poly(oxyethylene) polymer having a molecular weight of at least 1500.

The stabilizing composition provided in step a) can have one or more of the following characteristics:
a) it is capable of stabilization cells and reducing the release of genomic DNA from cells contained in the cell-containing biological sample into the cell-free portion of the sample;
b) it is capable of reducing the degradation of nucleic acids, in particular genomic DNA, present in the stabilized sample;
c) it is capable of reducing or preventing the contamination of the extracellular DNA population comprised in the biological sample with genomic DNA originating from cells contained in the stabilized sample;
d) it is capable of reducing or preventing the contamination of the extracellular nucleic acid population comprised in the biological sample with intracellular nucleic acids originating from cells contained in the stabilized sample;
e) the stabilization composition does not comprise additives in a concentration wherein said additives would induce or promote cell lysis;
f) the stabilization composition does not comprise a cross-linking agent that induces protein-DNA and/or protein-protein crosslinks such as formaldehyde, formalin, paraformaldehyde or a formaldehyde releaser;
g) the stabilization composition does not comprise a toxic agent;
h) it is capable of stabilizing extracellular nucleic acid population comprised in the cell-containing biological sample without refrigeration, preferably at room temperature, for a time period selected from at least three days, at least four, at least five or at least six days; and/or
i) the composition does not comprise the cell-containing sample to be stabilized which preferably is blood.

In particular, it is preferred that the composition does not comprise a cross-linking agent that induces protein-DNA and/or protein-protein crosslinks. A cross-linking agent that induces protein-DNA and/or protein-protein crosslinks is e.g. formaldehyde, formalin, paraformaldehyde or a formaldehyde releaser. This provides an important advantage over known state-of-the-art stabilization reagents and methods which involve the use of cross-linking reagents, such as formaldehyde, formaldehyde releasers and the like. Cross-linking reagents cause inter- or intra-molecular covalent bonds between nucleic acid molecules or between nucleic acids and proteins. This effect can lead to a reduced recovery of such stabilized and partially crosslinked nucleic acids after a purification or extraction from a complex biological sample. As, for example, the concentration of circulating nucleic acids in a whole blood samples is already relatively low, any measure which further reduces the yield of such nucleic acids should be avoided. This may be of particular importance when detecting and analyzing very rare nucleic acid molecules derived from malignant tumors or from a developing fetus in the first trimester of pregnancy. Therefore, it is preferred that no formaldehyde releaser is comprised in the sterilized stabilizing composition, respectively is not additionally used for stabilization. Thus, according to one embodiment, no cross-linking agents such as formaldehyde or formaldehyde releasers are comprised in the stabilizing composition, respectively are not additionally used for stabilization. Furthermore, as described, the stabilizing composition does preferably not comprise any additives that would induce the lysis of nucleated cells or cells in general, such as e.g. chaotropic salts.

Compositions comprising the caspase inhibitor Q-VD-OPh, dimethylpropionamide, PEG, EDTA such as $K_2$EDTA and one or more compounds according to Table A above are very suitable and have excellent sterilization as well as stabilization properties. The same applies for compositions comprising the caspase inhibitor Q-VD-OPh, dimethylpropionamide, PEG, EDTA such as $K_2$EDTA and one or more compounds according to Table B above. Most preferably, the composition comprises N-acetyl-cysteine. Compositions comprising ascorbic acid and compositions comprising glutathione (preferably in reduced form) are also preferred. Trolox has also been found to confer protection during sterilization. However the other compounds are more preferred.

As discussed, in embodiments, the caspase inhibitor containing stabilizing composition is also suitable for stabilizing intracellular nucleic acids, in particular intracellular DNA (e.g. genomic DNA) and/or intracellular RNA. In particular, it may be suitable for stabilizing intracellular RNA and preferably is suitable for stabilizing the gene transcription profile of contained cells. Therefore, intracellular nucleic acids isolated from respectively stabilized samples are well suitable e.g. for gene expression profiling and other analytical methods that require an accurate representation of in vivo transcript levels in the stabilized sample. Furthermore, advantageously, such stabilization allows if desired to isolate stabilized extracellular nucleic acids separately from stabilized intracellular nucleic acids from the same stabilized sample. A respective composition may comprise e.g. at least one primary or secondary carboxylic acid amide and/or at least one tertiary amide, preferably a N,N-dialkylpropanamide, more preferably N,N-dimethylpropanamide (see e.g. WO 2014/049022 and WO 2014/146781). After sample stabilization, intracellular RNA is protected from degradation and furthermore, changes in the gene transcription profile of contained cells are inhibited. Thus, the stabilization in particular reduces in vitro degradation and minimizes gene induction. Stabilizing the gene transcript levels of contained cells is advantageous, because the generation of new transcripts and the degradation of existing transcripts in the stabilized sample are inhibited compared to an unstabilized sample, thereby substantially "freezing" the gene transcription profile of contained cells upon stabilization. Therefore, the stabilization is also suitable for stabilizing the transcriptome by maintaining transcript levels at the state they had shown at sample collection and stabilization. The term transcriptome in particular refers to the set of all RNA molecules, including mRNA, rRNA, tRNA and other non-coding RNA such as miRNA, produced in one or a population of cells. In embodiments, a cell-containing biological sample such as a blood sample can be stabilized for at least three days without substantial changes of transcript levels. The gene transcription profile is in particular stabilized by reducing RNA degradation and minimizing alterations of the gene expression such as in particular gene induction or down-regulation. Thereby, the in vivo gene expression profile existing at collection, respectively stabilization is preserved. Furthermore, the quality and integrity of the RNA can be maintained, thereby providing an accurate representation of the in vivo transcript levels at the time of sample collection, respectively sample stabilization. The preservation of the in vivo gene transcription profile upon stabilization allows performing e.g. gene expression profiling or other analytical methods that require an accurate representation of the transcript levels using respectively stabilized samples. However, even though desired, it is often not necessary that all transcript levels are stabilized or are stabilized equally well. The stabilization and thus performance characteristics for a specific or new target transcript should be validated as is also usual with the prior art technologies which stabilize gene transcription profiles. That stabilization of the gene transcription profile or of specific transcript levels was achieved can be determined e.g. based on marker genes that are established for analyzing the stabilization of the gene transcription profile. According to one embodiment, the stabilization of the gene transcription profile or the transcript level of contained cells results in that one or more, preferably two or more marker genes selected from c-fos, IL-1beta, IL-8 and p53 is/are stabilized for at least 12 h, for at least 24 h or for at least 48 h upon stabilization. These marker genes were identified as providing very unstable transcripts during storage and thus are in the absence of appropriate stabilization up- or downregulated after sample collection. Therefore, the transcript levels of these genes are suitable as marker to analyse whether a stabilization of the gene transcription level was achieved. The stabilization effect can be analysed using the real time RT-PCR assays described in the examples. According to one embodiment, the transcript levels of one or more of these marker genes is not altered by more than 1.5 CT values, preferably not more than 1.25 CT values, more preferred not more than 1 CT value between $T_0$ (stabilization point) and the end of the stabilization period. Preferably, a respective stabilization effect is achieved for at least 12 h, for at least 24 h, for at least 48 h, at least 72 h or at least 96 h. Preferably, respective stabilization characteristics are achieved at least with the marker genes c-fos, IL8 and IL-1beta and preferably with all of the aforementioned marker genes. As is demonstrated in W2014/049022 and W2014/146781, various amides, such as primary and/or secondary carboxylic acid amides achieve a respective stabilization performance.

In embodiments, the sterilized stabilization composition is capable of preserving characteristics of cells contained in a sample to be stabilized such as e.g. cell surface characteristics and/or the cell morphology of contained cells are preserved. The cells remain intact due to the stabilization. This allows e.g. to separate the cells from the stabilized sample after the stabilization period and cells isolated from the stabilized sample are suitable for analysis. E.g., intracellular nucleic acids such as DNA and/or RNA can be isolated from the comprised cells and can be analyzed. Furthermore, the preservation of cells in the stabilized samples opens the possibility to sort or capture cells and even to enrich specific cells such as e.g. tumor cells that can then be analyzed specifically. E.g. circulating tumor cells can be isolated and their gene expression profile can be analyzed. Furthermore, the cell morphology and/or cell markers in particular cell surface markers can be analyzed in order to characterize the obtained cells. Furthermore, intracellular nucleic acids can be isolated from said enriched specific cells. E.g. RNA can be isolated from said cells. The transcript level stabilizing properties of stabilization compositions described herein advantageously allows using the isolated RNA for gene expression profiling and other important analyses. Such stabilisation is thus advantageous for example in the molecular diagnostic of cancer or other diseases, because it allows an enrichment of cells prior to the extraction of the nucleic acids from the enriched cells and thereby increases e.g. the chance to detect rare events of circulating tumor cells in the cell-containing samples, for example in a blood sample. This also increases the chance that a specific biomarker, in particular a rare biomarker, is identified in the sample. According to one embodiment, the morphology of cells is preserved during the stabilization period which preferably is at least 12 h, at least 24 h and more preferred at least 48 h. This allows analyzing and optionally characterizing contained cells based on their morphology. According to one embodiment, the morphology of nucleated cells is preserved. According to one embodiment, the morphology of lymphocytes contained in a blood sample is preserved during stabilization when using the sterilized stabilizing composition. According to one embodiment, cell surface epitopes of cells are preserved. According to one embodiment, cell surface proteins such as CD proteins are preserved. The preservation of cell surface epitopes and cell surface proteins is an advantage as it allows characterizing and/or isolating contained cells based on these cell surface characteristics. In particular, it allows the analysis of tumor markers present on the cell surface or the isolation of specific cells based on said markers. Suitable stabilizing compositions for that purpose are e.g. described in WO 2014/049022 and WO 2014/146781 to which it is referred.

In embodiments, the stabilizing composition used is suitable for stabilizing the proteome.

Step b) Irradiating the Composition for Sterilization

The method further comprises in step b) irradiating the stabilization composition for sterilization. As explained above, the composition is irradiated prior to contacting the composition with a biological sample. The aim is to provide a sterilized stabilization composition comprising a caspase inhibitor that can be used for stabilizing an extracellular nucleic acid population in a biological sample e.g. by contacting the sample with the sterilized composition.

Several irradiation forms are suitable and can be applied. Irradiation forms suitable for sterilization of compositions and devices are known to the skilled person. For example, ionizing irradiation can be used, ionizing forms of irradiation suitable for sterilization of compositions and devices likewise being known to the skilled person. Examples of ionizing irradiation are gamma irradiation, electron beam irradiation, X-ray and ionizing ultraviolet radiation. For performing the present invention, gamma irradiation, electron beam irradiation and X-ray are preferred; gamma irradiation and X-ray are more preferred. Irradiation by gamma irradiation is most preferred.

Gamma irradiation dosage is measured in kilogray (kGy) units, which quantify the absorbed energy of radiation. One gray is the absorption of one joule of radiation energy by one kilogram of matter (one kGy=one joule/gram).

The composition can be irradiated with irradiation dose of 5 kGy to 35 kGy, 6 kGy to 30 kGy, 7 kGy to 26 kGy, or about 8 kGy to about 25 kGy, such as about 8 kGy to about 15 kGy or about 15 kGy to about 25 kGy. Irradiation with an irradiation dose of about 8 kGy to about 15 kGy offers the advantage of comparably mild irradiation conditions that further support the maintenance of stabilization properties in the irradiated composition. Irradiation with an irradiation dose of about 15 kGy to about 25 kGy is likewise well feasible and particularly cost efficient, which represents an important advantage for large scale production. The composition can be irradiated by gamma irradiation with an irradiation dose of about 8 kGy to about 25 kGy, about 8 kGy to about 15 kGy or about 15 kGy to about 25 kGy. The composition can be irradiated by gamma irradiation with an irradiation dose of 5 kGy to 35 kGy, 6 kGy to 30 kGy, 7 kGy to 26 kGy, or about 8 kGy to about 25 kGy, such as about 8 kGy to about 15 kGy or about 15 kGy to about 25 kGy.

The irradiation dose can be applied over a wide range of irradiation times. While irradiation time has been found not to be a critical parameter for the irradiation of the stabilizing solution, it may be preferred from a practical and economical point of view to choose comparably short irradiation times. The skilled person is familiar with choosing appropriate irradiation times. Exemplary ranges comprise 1 second to 1 hour, 1 second to 30 min, 2 seconds to 10 min, or 5 seconds to 1 min.

Typically, the composition is irradiated with an irradiation dose high enough to ensure that the composition is sterilized.

"Sterility" or "sterilized" as used herein can in particular be defined by the probability of a viable microorganism on the product after it has been sterilized. This probability can be referred to as a sterility assurance level (SAL). By way of example, a SAL of $10^{-6}$ is frequently used for the sterilization of medical devices. A SAL of $10^{-6}$ as used herein can in particular mean a probability of 1 in 1,000,000 of finding a non-sterile unit, such as a non-sterile composition or device after sterilization. "Sterility" or "sterilized" as used herein can in particular refer to a SAL of $10^{-4}$ or less, more preferably $10^{-5}$ or less, most preferably $10^{-6}$ or less. According to one embodiment, "sterility" or "sterilized" signifies "free from viable microorganisms".

Appropriate validation methods in order to demonstrate that a sterilization process routinely delivers a chosen SAL are known to the skilled person and for irradiation are e.g. set out in ANSI/AAMI/ISO 11137:2006.

Accordingly, sterilization by irradiation can result in a sterility assurance level (SAL) of a composition or device of $10^{-4}$ or less, more preferably $10^{-5}$ or less, most preferably $10^{-6}$ or less. Irradiation can fulfil the requirements of ISO norms ISO11137-1:2006, ISO11137-2:2012, and/or ISO11137-3:2006.

According to a preferred embodiment, sterility is achieved by irradiation with an irradiation dose of 5 kGy to 35 kGy, 6 kGy to 30 kGy, 7 kGy to 26 kGy, or about 8 kGy to about 25 kGy, such as about 8 kGy to about 15 kGy or about 15 kGy to about 25 kG, about 8 kGy to about 15 kGy being particularly preferred, wherein preferably, irradiation is by gamma irradiation.

The form in which the composition is irradiated is not limited. Thus, the composition can for example be irradiated in a solid or in a liquid form. However, for all embodiments described herein it is preferred that the composition is irradiated for sterilization in a liquid, preferably aqueous, form.

The at least one compound selected from N-acetyl-cysteine, glutathione, a water-soluble vitamin, and vitamin E or a derivative thereof were found to be particularly active in protecting liquid, especially aqueous stabilization compositions comprising one or more caspase inhibitors, in particular comprising one or more peptidic caspase inhibitors. This is surprising, because liquid compositions frequently have been found to be difficult to sterilize in the prior art (e.g. in the pharmaceutical field) without impairing the function of the composition. Irradiating compositions suitable for stabilizing an extracellular nucleic acid population of a biological sample comprising one or more caspase inhibitors in a liquid, in particular aqueous, form is desirable. This allows to provide sterilized stabilization compositions that can be conveniently handled and mixed with biological samples, in particular liquid biological samples such as blood, plasma or serum.

If the composition is irradiated in a liquid, preferably aqueous form, it is possible to initially provide, e.g. prepare the composition in step a) in a solid form that is then dissolved in a suitable solvent to provide a liquid, preferably aqueous composition that is then irradiated for sterilization. This can be done e.g. by dissolving the composition prior or during step b).

According to one embodiment, the stabilization composition is irradiated in a non-solid state. According to one embodiment, the stabilization composition is irradiated in a non-frozen state.

The stabilization composition comprising at least one caspase inhibitor can be sterilized in a sample collection device such as a container. The container can be a tube, more preferably a blood collection tube. The container typically consists of materials suitable for irradiation. For example, the container, such as a blood collection tube, can comprise or consists of polyethylene terephthalate. The collection device can be a device according to the seventh aspect of the invention.

Irradiating the composition for sterilization can provide a sterilized composition. Accordingly, the method of the first aspect of the invention preferably is a method of producing a sterilized composition suitable for stabilizing an extracellular nucleic acid population of a biological sample, the method comprising:

a) providing a stabilization composition as described above; and b) sterilizing the composition by irradiation.

Further details and embodiments of the stabilizing composition were described above and it is referred to the respective disclosure. In embodiments, the sterilized composition is suitable to additionally stabilize intracellular nucleic acids (in particular intracellular RNA and/or intracellular DNA, such as e.g. genomic DNA). In embodiments, the sterilized composition is suitable to additionally stabilize cell characteristics, such as e.g. cell surface characteristics and/or the cell morphology. It is referred to the above disclosure which also applies here. The composition preferably is sterilized in a liquid, more preferably aqueous, form. It is referred to the above disclosure.

Specific Embodiments According to the First Aspect of the Invention

Suitable and preferred embodiments of the method according to the first aspect of the invention are described in the following.

According to one embodiment of the first aspect of the invention, a method of producing a sterilized composition suitable for stabilizing an extracellular nucleic acid population of a biological sample is provided, the method comprising:

a) providing a liquid, preferably aqueous, composition comprising:

i. at least one caspase inhibitor, preferably a pancaspase inhibitor, more preferably a caspase inhibitor comprising a modified caspase-specific peptide. Said caspase-specific peptide can be modified by an aldehyde, nitrile or ketone compound. According to one embodiment, the caspase specific peptide is modified, preferably at the carboxyl terminus, with an O-Phenoxy (OPh) or a fluoromethyl ketone (FMK) group. According to one embodiment, the caspase inhibitor is selected from the group consisting of Q-VD-OPh, Boc-D-(OMe)-FMK and Z-VAD (OMe)-FMK. According to one embodiment, the caspase inhibitor is selected from the group consisting of Q-VD-OPh and Z-VAD(OMe)-FMK, most preferred Q-VD-OPh.

ii. one or more of the following compounds:
   N-acetyl-cysteine in a concentration of 0.05 mg/ml to 15 mg/ml, 0.1 mg/ml to 10 mg/ml, 0.1 mg/ml to 7.5 mg/ml, 0.1 mg/ml to 5 mg/ml, 0.1 mg/ml to 2 mg/ml, 0.2 mg/ml to 1 mg/ml, or 0.3 mg/ml to 0.8 mg/ml,
   glutathione in reduced form in a concentration of 0.03 mg/ml to 10 mg/ml, 0.04 mg/ml to 7.5 mg/ml, 0.075 mg/ml to 5 mg/ml, 0.15 mg/ml to 4 mg/ml, 0.3 mg/ml to 3 mg, 0.4 mg/ml to 2 mg/ml, or 0.4 mg/ml to 1.3 mg/ml and/or
   ascorbic acid in a concentration of less than 20 mg/ml, such as 1 mg/ml to 15 mg/ml, 0.2 mg/ml to 14 mg/ml, 0.5 mg/ml to 13.5 mg/ml, 1 mg/ml to 13 mg/ml, 1.5 mg/ml to 12 mg/ml, or 2 mg/ml to 11 mg/ml,
   a B vitamin, preferably vitamin B6, in a concentration of 0.1 mg/ml to 15 mg/ml, 0.1 mg/ml to 14 mg/ml, 0.1 mg/ml to 11 mg/ml, 0.2 mg/ml to 7.5 mg/ml, or 0.2 mg/ml to 2 mg/ml,
   the composition optionally further comprising one or more components selected from:
iii. at least one poly(oxyethylene) polymer as stabilizing agent, wherein preferably the poly(oxyethylene) polymer is a polyethylene glycol, more preferably an unsubstituted polyethylene glycol,
iv. at least one primary, secondary or tertiary amide, preferably an N,N-dialkylpropanamide (e.g. N,N-dimethlypropanamide) and/or butanamide,
v. an anticoagulant and/or a chelating agent, preferably EDTA; and
b) irradiating the composition for sterilization, preferably by gamma irradiation.

In embodiments, the at least one poly(oxyethylene) polymer, which preferably is a polyethylene glycol, is selected from a low molecular weight poly(oxyethylene) polymer, preferably a low molecular weight poly(oxyethylene) polymer having a molecular weight of 1000 or less, and/or a high molecular weight poly(oxyethylene) polymer having a molecular weight of at least 1500.

The composition can be sterilized by irradiating the composition.

According to a further embodiment of the first aspect of the invention, a method of producing a sterilized composition suitable for stabilizing an extracellular nucleic acid population of a biological sample is provided, the method comprising:
a) providing a liquid, preferably aqueous, composition comprising:
   i. at least one caspase inhibitor, preferably a pancaspase inhibitor, more preferably a caspase inhibitor comprising a modified caspase-specific peptide. Said caspase-specific peptide can be modified by an aldehyde, nitrile or ketone compound. According to one embodiment, the caspase specific peptide is modified, preferably at the carboxyl terminus, with an O-Phenoxy (OPh) or a fluoromethyl ketone (FMK) group. According to one embodiment, the caspase inhibitor is selected from the group consisting of Q-VD-OPh, Boc-D-(OMe)-FMK and Z-VAD (OMe)-FMK. According to one embodiment, the caspase inhibitor is selected from the group consisting of Q-VD-OPh and Z-VAD(OMe)-FMK, most preferred Q-VD-OPh.

ii. one or more of the following compounds:
   N-acetyl-cysteine in a concentration of 0.05 mg/ml to 15 mg/ml, 0.1 mg/ml to 10 mg/ml, 0.1 mg/ml to 7.5 mg/ml, 0.1 mg/ml to 5 mg/ml, 0.1 mg/ml to 2 mg/ml, 0.2 mg/ml to 1 mg/ml, or 0.3 mg/ml to 0.8 mg/ml,
   glutathione in reduced form in a concentration of 0.03 mg/ml to 10 mg/ml, 0.04 mg/ml to 7.5 mg/ml, 0.075 mg/ml to 5 mg/ml, 0.15 mg/ml to 4 mg/ml, 0.3 mg/ml to 3 mg, 0.4 mg/ml to 2 mg/ml, or 0.4 mg/ml to 1.3 mg/ml and/or
   ascorbic acid in a concentration of less than 20 mg/ml, such as 1 mg/ml to 15 mg/ml, 0.2 mg/ml to 14 mg/ml, 0.5 mg/ml to 13.5 mg/ml, 1 mg/ml to 13 mg/ml, 1.5 mg/ml to 12 mg/ml, or 2 mg/ml to 11 mg/ml, the composition optionally further comprising one or more components selected from:
iii. at least one high molecular weight poly(oxyethylene) polymer having a molecular weight of at least 1500, preferably in a range of 2000 to 40000, more preferred 2500 to 30000, 2500 to 25000 or 3000 to 20000,
iv. at least one primary, secondary or tertiary amide, preferably an N,N-dialkylpropanamide (e.g. N,N-dimethlypropanamide) and/or butanamide,
v. at least one further poly(oxyethylene) polymer having a molecular weight that is at least 100, preferably at least 200, at least 300 or at least 400 below the molecular weight of the high molecular weight poly(oxyethylene) polymer used and wherein said further poly(oxyethylene) polymer preferably is a low molecular weight poly(oxyethylene) having a molecular weight of 1000 or less, preferably having a molecular weight in a range of 200 to 800 or 200 to 600, and
vi. an anticoagulant and/or a chelating agent, preferably EDTA; and
b) irradiating the composition for sterilization, preferably by gamma irradiation.

The composition can be sterilized by irradiating the composition.

According to a further embodiment of the first aspect of the invention, a method of producing a sterilized composition suitable for stabilizing an extracellular nucleic acid population of a biological sample is provided, the method comprising:
a) providing a liquid composition which preferably is aqueous, comprising:
   i. at least one caspase inhibitor, preferably a pancaspase inhibitor, more preferably a caspase inhibitor comprising a modified caspase-specific peptide as described above, most preferred Q-VD-OPh,
   ii. at least one compound as defined in Table A or Table B above, preferably wherein the composition comprises N-acetyl-cysteine,
   the composition optionally further comprising one or more components selected from:
   iii. at least one high molecular weight poly(oxyethylene) polymer having a molecular weight of at least 1500, preferably in a range of 2000 to 40000, more preferred 2500 to 30000, 2500 to 25000 or 3000 to 20000, iv. at least one primary, secondary or tertiary amide, preferably an N,N-dialkylpropanamide (e.g. N,N-dimethlypropanamide) and/or butanamide, v. at least one further poly(oxyethylene) polymer having a molecular weight that is at least 100, preferably at least 200, at least 300 or at least 400 below the molecular weight of the high molecular weight poly(oxyethylene) polymer used and wherein said further poly(oxyethylene) polymer preferably is a low molecular weight poly(oxyethylene) having a molecular weight of 1000 or less, preferably having a molecular weight in a range of 200 to 800 or 200 to 600, and vi. an anticoagulant and/or a chelating agent, preferably EDTA; and b) irradiating the composition for sterilization, preferably by gamma irradiation.

The stabilization composition can be sterilized by irradiating the composition.

According to a preferred embodiment, the present invention provides a method of producing a sterilized composition suitable for stabilizing an extracellular nucleic acid population of a biological sample, the method comprising:
a) providing an aqueous composition comprising:
i. at least one pancaspase inhibitor, more preferred more preferably a caspase inhibitor comprising a modified caspase-specific peptide as described above, most preferred Q-VD-OPh, ii. N-acetyl-cysteine in a concentration of 0.05 mg/ml to 15 mg/ml, 0.1 mg/ml to 10 mg/ml, 0.1 mg/ml to 7.5 mg/ml, 0.1 mg/ml to 5 mg/ml, 0.1 mg/ml to 2 mg/ml, 0.2 mg/ml to 1 mg/ml, or 0.3 mg/ml to 0.8 mg/ml and optionally further comprising:
iii. at least one poly(oxyethylene) polymer as stabilizing agent, wherein preferably the poly(oxyethylene) polymer is a polyethylene glycol, more preferably an unsubstituted polyethylene glycol, iv. at least one primary, secondary or tertiary amide, preferably an N,N-dialkylpropanamide (e.g. N,N-dimethlypropanamide) and/or butanamide, and v. optionally an anticoagulant and/or a chelating agent, preferably EDTA; and b) irradiating the composition for sterilization, preferably by gamma irradiation, more preferably with a dose of 5 kGy to 35 kGy, 6 kGy to 30 kGy, 7 kGy to 26 kGy, about 8 kGy to about 25 kGy, or about 8 kGy to about 15 kGy.

In embodiments, the at least one poly(oxyethylene) polymer, which preferably is a polyethylene glycol, is selected from a low molecular weight poly(oxyethylene) polymer, preferably a low molecular weight poly(oxyethylene) polymer having a molecular weight of 1000 or less, and/or a high molecular weight poly(oxyethylene) polymer having a molecular weight of at least 1500.

The stabilization composition can be sterilized by irradiating the composition.

According to a further preferred embodiment, the present invention provides a method of producing a sterilized composition suitable for stabilizing an extracellular nucleic acid population of a biological sample, the method comprising:
a) providing an aqueous composition comprising:
i. at least one pancaspase inhibitor, more preferred more preferably a caspase inhibitor comprising a modified caspase-specific peptide as described above, most preferred Q-VD-OPh, ii. N-acetyl-cysteine in a concentration of 0.05 mg/ml to 15 mg/ml, 0.1 mg/ml to 10 mg/ml, 0.1 mg/ml to 7.5 mg/ml, 0.1 mg/ml to 5 mg/ml, 0.1 mg/ml to 2 mg/ml, 0.2 mg/ml to 1 mg/ml, or 0.3 mg/ml to 0.8 mg/ml, and optionally further comprising:
iii. at least one high molecular weight poly(oxyethylene) polymer having a molecular weight of at least 1500, preferably in a range of 2000 to 40000, more preferred 2500 to 30000, 2500 to 25000 or 3000 to 20000, iv. at least one primary, secondary or tertiary amide, preferably an N,N-dialkylpropanamide (e.g. N,N-dimethlypropanamide) and/or butanamide, v. at least one further poly(oxyethylene) polymer having a molecular weight that is at least 100, preferably at least 200, at least 300 or at least 400 below the molecular weight of the high molecular weight poly(oxyethylene) polymer used and wherein said further poly(oxyethylene) polymer preferably is a low molecular weight poly(oxyethylene) having a molecular weight of 1000 or less, preferably having a molecular weight in a range of 200 to 800 or 200 to 600, and vi. optionally an anticoagulant and/or a chelating agent, preferably EDTA; and b) irradiating the composition for sterilization, preferably by gamma irradiation, more preferably with a dose of 5 kGy to 35 kGy, 6 kGy to 30 kGy, 7 kGy to 26 kGy, about 8 kGy to about 25 kGy, or about 8 kGy to about 15 kGy.

The stabilization composition can be sterilized by irradiating the composition.

According to one embodiment, in the above preferred embodiment, the aqueous composition provided in step a) comprises glutathione in reduced form in a concentration of 0.03 mg/ml to 10 mg/ml, 0.04 mg/ml to 7.5 mg/ml, 0.075 mg/ml to 5 mg/ml, 0.15 mg/ml to 4 mg/ml, 0.3 mg/ml to 3 mg, 0.4 mg/ml to 2 mg/ml, or 0.4 mg/ml to 1.3 mg/ml, and/or comprises ascorbic acid in a concentration of less than 20 mg/ml, such as 0.05 mg/ml to 15 mg/ml, 0.1 mg/ml to 14 mg/ml, 0.5 mg/ml to 13.5 mg/ml, 1 mg/ml to 13 mg/ml, 1.5 mg/ml to 12 mg/ml, or 2 mg/ml to 11 mg/ml.

Glutathione in reduced form and ascorbic acid can be comprised in the composition in addition to N-acetyl-cysteine or as an alternative to N-acetyl-cysteine. However, as explained before, it is advantageous that the composition comprises N-acetyl-cysteine.

According to a further preferred embodiment, the present invention provides a method of producing a sterilized composition suitable for stabilizing an extracellular nucleic acid population of a biological sample, the method comprising:
a) providing an aqueous composition comprising:
i. the caspase inhibitor Q-VD-OPh, ii. N-acetyl-cysteine in a concentration of 0.05 mg/ml to 15 mg/ml, 0.1 mg/ml to 10 mg/ml, 0.1 mg/ml to 7.5 mg/ml, 0.1 mg/ml to 5 mg/ml, 0.1 mg/ml to 2 mg/ml, 0.2 mg/ml to 1 mg/ml, or 0.3 mg/ml to 0.8 mg/ml, the composition optionally further comprising:
iii. at least one poly(oxyethylene) polymer as stabilizing agent, wherein preferably the poly(oxyethylene) polymer is a polyethylene glycol, more preferably an unsubstituted polyethylene glycol, iv. at least one primary, secondary or tertiary amide, preferably an N,N-dialkylpropanamide (e.g. N,N-dimethlypropanamide) and/or butanamide, and v. optionally an anticoagulant and/or a chelating agent, preferably EDTA; and b) sterilizing the composition by gamma irradiation, preferably with a dose of 5 kGy to 35 kGy, 6 kGy to 30 kGy, 7 kGy to 26 kGy, about 8 kGy to about 25 kGy, or about 8 kGy to about 15 kGy.

In embodiments, the at least one poly(oxyethylene) polymer, which preferably is a polyethylene glycol, is selected from a low molecular weight poly(oxyethylene) polymer, preferably a low molecular weight poly(oxyethylene) polymer having a molecular weight of 1000 or less, and/or a high molecular weight poly(oxyethylene) polymer having a molecular weight of at least 1500.

According to a further preferred embodiment, the present invention provides a method of producing a sterilized composition suitable for stabilizing an extracellular nucleic acid population of a biological sample, the method comprising:
a) providing an aqueous composition comprising:
   i. the caspase inhibitor Q-VD-OPh,
   ii. N-acetyl-cysteine in a concentration of 0.05 mg/ml to 15 mg/ml, 0.1 mg/ml to 10 mg/ml, 0.1 mg/ml to 7.5 mg/ml, 0.1 mg/ml to 5 mg/ml, 0.1 mg/ml to 2 mg/ml, 0.2 mg/ml to 1 mg/ml, or 0.3 mg/ml to 0.8 mg/ml,
   the composition optionally further comprising:
   iii. at least one high molecular weight poly(oxyethylene) polymer having a molecular weight of at least 1500, preferably in a range of 2000 to 40000, more preferred 2500 to 30000, 2500 to 25000 or 3000 to 20000,
   iv. at least one primary, secondary or tertiary amide, preferably an N,N-dialkylpropanamide (e.g. N,N-dimethlypropanamide) and/or butanamide,
   v. at least one further poly(oxyethylene) polymer having a molecular weight that is at least 100, preferably at least 200, at least 300 or at least 400 below the molecular weight of the high molecular weight poly(oxyethylene) polymer used and wherein said further poly(oxyethylene) polymer preferably is a low molecular weight poly(oxyethylene) having a molecular weight of 1000 or less, preferably having a molecular weight in a range of 200 to 800 or 200 to 600, and
   vi. an anticoagulant and/or a chelating agent, preferably EDTA; and
b) sterilizing the composition by gamma irradiation, preferably with a dose of 5 kGy to 35 kGy, 6 kGy to 30 kGy, 7 kGy to 26 kGy, about 8 kGy to about 25 kGy, or about 8 kGy to about 15 kGy.

According to one embodiment, the composition provided in step a) and irradiated in step b) does not comprise tannic acid and does not comprise gallic acid. According to one embodiment, the composition further does not comprise mannitol, isopropanol and/or Tween-80 or other compounds that can interfere with the stabilization effect. According to one embodiment, the composition has a mildly acidic pH.

According to one embodiment, the stabilization composition comprises the caspase inhibitor Q-VD-OPh in a concentration selected from 0.35 µg/ml to 70 µg/ml, 0.7 µg/ml to 63 µg/ml, 1.74 µg/ml to 59 µg/ml, 10.5 µg/ml to 56 µg/ml, or 15 µg/ml to 50 µg/ml, 20 µg/ml to 45 µg/ml, 25 µg/ml to 40 µg/ml and 30 µg/ml to 38 µg/ml.

B. Method for Stabilizing an Extracellular Nucleic Acid Population

According to a second aspect, the present invention provides a method for stabilizing an extracellular nucleic acid population comprised in a cell-containing biological sample comprising:
a) producing a sterilized composition suitable for stabilizing an extracellular nucleic acid population of a biological sample according to a method of the first aspect of the invention; and
b) contacting the cell-containing biological sample with the sterilized composition.

Also contemplated is a method for stabilizing an extracellular nucleic acid population comprised in a cell-containing biological sample comprising:
a) obtaining a composition according to the sixth aspect of the invention, wherein the composition is sterilized, or obtaining a sample collection device according to the seventh aspect of the invention, wherein the composition comprised therein is sterilized; and
b) contacting the cell-containing biological sample with the sterilized composition.

Suitable and preferred embodiments of the stabilization composition and the compounds used for sterilization protection were described above and it is referred to the above disclosure which also applies here. According to a preferred embodiment, the stabilized extracellular nucleic acid population is ccfDNA.

After contacting the cell-containing biological sample with the composition, the resulting mixture can for example comprise:
a) at least one caspase inhibitor, preferably a pancaspase inhibitor, more preferred Q-VD-OPh, preferably in a concentration that lies in a range of 0.1 µM to 20 µM, 0.2 µM to 18 µM, 0.5 µM to 17 µM, 3 µM to 16 µM, more preferred 3 µM to 12 µM;

and one or more of
b) N-acetyl-cysteine in a concentration range selected from 0.05 mM to 13.4 mM, 0.09 mM to 8.9 mM, 0.09 mM to 6.7 mM, 0.09 mM to 4.5 mM, 0.09 mM to 1.8 mM, 0.18 mM to 0.9 mM, or 0.27 mM to 0.71 mM;
c) glutathione, preferably in reduced form, in a concentration range selected from 0.01 mM to 4.2 mM, 0.02 mM to 3.15 mM, 0.03 mM to 2.1 mM, 0.06 mM to 1.68 mM, 0.13 mM to 1.26 mM, 0.17 mM to 0.95 mM or 0.17 mM to 0.61 mM;
d) a water soluble vitamin, preferably ascorbic acid, in a concentration range selected from less than 16.5 mM, such as 0.08 mM to 12.4 mM, 0.83 mM to 10.72 mM, 1.24 mM to 9.9 mM, or 1.65 mM to 9.1 mM;
e) vitamin E or a derivative thereof, preferably a water-soluble vitamin E derivative, more preferably trolox, in a concentration range selected from 0.29 mM to 2.9 mM, 0.44 mM to 1.74 mM, 0.52 mM to 1.16 mM, or 0.58 mM to 0.81 mM.

It is also contemplated that the resulting mixture can comprise a B vitamin, preferably vitamin B6, in a concentration range selected from 0.08 mM to 12.9 mM, 0.08 mM to 12 mM, 0.1 mM to 9.4 mM, 0.17 mM to 6.4 mM, or 0.17 mM to 1.7 mM.

The use of N-acetyl-cysteine is preferred.

After the cell-containing biological sample has been contacted with the sterilized stabilization composition, the resulting mixture can comprise one or more of:
a) one or more compounds according to formula 1 in a concentration that lies in a range of 0.25% to 5%, 0.3% to 4%, 0.4% to 3%, 0.5% to 2.5% or 0.75% to 2%;

b) at least one poly(oxyethylene) polymer, wherein preferably the poly(oxyethylene) polymer is a polyethylene glycol, more preferably an unsubstituted polyethylene glycol;
c) a chelating agent, more preferably EDTA.

In embodiments, the at least one poly(oxyethylene) polymer, which preferably is a polyethylene glycol, is selected from a low molecular weight poly(oxyethylene) polymer, preferably a low molecular weight poly(oxyethylene) polymer having a molecular weight of 1000 or less, and/or a high molecular weight poly(oxyethylene) polymer having a molecular weight of at least 1500.

Accordingly, after the cell-containing biological sample has been contacted with the sterilized stabilization composition, the resulting mixture can comprise one or more of:
  a) one or more compounds according to formula 1 in a concentration that lies in a range of 0.25% to 5%, 0.3% to 4%, 0.4% to 3%, 0.5% to 2.5% or 0.75% to 2%;
  b) a high molecular weight poly(oxyethylene) polymer in a concentration range selected from 0.1% to 3% (w/v), 0.2% to 2.5% (w/v), 0.25% to 2% (w/v), 0.3% to 1.75% (w/v) and 0.35% to 1.5% (w/v) or selected from 0.25% to 1.5% (w/v), 0.3% to 1.25% (w/v), 0.35% to 1% (w/v) and 0.4% to 0.75% (w/v);
  c) a low molecular weight poly(oxyethylene) polymer in a concentration range selected from 0.5% to 10%, 1.5% to 9%, 1.75% to 8%, 2% to 7% and 2.5% to 6%;
  d) a chelating agent, more preferably EDTA.

According to one embodiment, the cell-containing sample is a blood sample. In this embodiment, stabilization preferably involves the use of an anticoagulant which can be a chelating agent such as EDTA.

As described herein, in embodiments, the sterilized composition is suitable to additionally stabilize intracellular nucleic acids such as intracellular DNA (e.g. genomic DNA) and/or RNA. According to one embodiment, the degradation of nucleic acids present in the cell-containing sample is reduced due to the stabilization. In particular, intracellular RNA is stabilized. Preferably, the transcriptome and/or transcript levels in cells contained in the sample are stabilized. Details were described above. According to one embodiment, the transcript level of one or more marker genes selected from c-fos, IL-1beta, IL-8 and p53 is stabilized for at least 12 h, for at least 24 h, preferably for at least 48 h upon stabilization. According to one embodiment, upon contact of the stabilizing composition with a blood sample the transcript level of one or more marker genes selected from c-fos, IL-1beta, IL-8 and p53 is stabilized for at least 12 h, for at least 24 h, preferably for at least 48 h upon stabilization, and wherein, in one embodiment, the volumetric ratio of the stabilizing composition to the cell-containing sample is selected from 10:1 to 1:20, 5:1 to 1:15, 1:1 to 1:10 and 1:2 to 1:5.

In embodiments, the sterilized composition is suitable to additionally stabilize cell characteristics, such as e.g. cell surface characteristics and/or the cell morphology. Importantly, the stabilized cells remain intact and thus can be isolated from the stabilized sample. It is referred to the above disclosure. In one embodiment, the stabilization method has one or more of the following characteristics:
  a) the stabilization allows the isolation of cells from the stabilized sample;
  b) the cell-containing sample is a blood sample and wherein cells contained in the blood sample are stabilized;
  c) the cell-containing sample is a blood sample and wherein white blood cells are stabilized;
  d) the morphology of cells is preserved;
  e) the morphology of nucleated cells is preserved;
  f) the sample is a blood sample and contained lymphocytes and/or monocytes are stabilized;
  g) cell surface epitopes are preserved; and/or
  h) cell surface proteins are preserved.

According to one embodiment, the sample is a blood sample and wherein the morphology of and/or cell surface epitopes on white blood cells, preferably lymphocytes, is preserved. As discussed above, also the characteristics of other cells comprised in the blood sample may be preserved, e.g. of circulating tumor cells, if present.

After the stabilization period, the method may comprise one or more of the following
  a) the stabilized sample is subjected to a nucleic acid analysis and/or detection method;
  b) extracellular nucleic acids are isolated from the stabilized sample;
  c) extracellular nucleic acids are isolated from the stabilized sample and the isolated nucleic acids are analysed and/or detected;
  d) cells comprised in the stabilized sample are removed;
  e) cells comprised in the stabilized sample are removed prior to performing an nucleic acid isolation, analysis and/or detection step;
  f) cells are removed from the stabilized sample and extracellular nucleic acids are isolated from the cell-free or cell-depleted portion of the stabilized sample;
  g) (i) the stabilized sample, (ii) the stabilized sample from which cells have been removed and/or (iii) cells removed from the sample are stored;
  h) cells are removed from the stabilized sample and are discarded; and/or
  i) cells are removed from the stabilized sample and nucleic acids are isolated from cells that were removed from the stabilized sample;
  j) cells are removed from the stabilized sample and biomolecules, such as proteins and/or metabolites, nucleic acids are isolated from cells that were removed from the stabilized sample;
  k) cells are removed from the stabilized sample and nucleic acids and biomolecules, such as proteins and/or metabolites, are isolated from cells that were removed from the stabilized sample
  l) cells are removed from the stabilized sample and extracellular nucleic acids are isolated from the cell-free or cell-depleted portion of the stabilized sample using a size selective nucleic acid isolation method.

Hence, the cell-containing biological sample that was stabilized using the method of the present invention can be analysed in a nucleic acid analytic and/or detection method and/or may be further processed. The stabilization of the biological sample may either be followed directly by techniques for analysing nucleic acids, or nucleic acids may first be isolated from the stabilized sample. Details regarding the nucleic acid isolation and analysis are also described below in conjunction with the third aspect of the present invention and it is referred to said disclosure.

Furthermore, as described, cells can be removed from the stabilized sample and analysed and/or nucleic acids can be isolated from the obtained cells. This allows e.g. to identify tumor cells. According to one embodiment, intracellular RNA is isolated from the cells contained in the stabilized sample and analysed. According to one embodiment, the method comprises performing a qualitative or quantitative analysis of one or more gene transcripts. Furthermore, in embodiments, the cells can be analysed for their morphology or cell surface characteristics.

According to one embodiment, the cell-containing sample is a blood sample and the sterilized stabilizing composition achieves a stabilization of white blood cells. This allows separating white blood cells from the stabilized sample. White blood cells are stabilized, if at least one type of the contained blood cells is stabilized during the stabilization period which preferably, is at least 12 h, more preferably at least 24 h, more preferably at least 48 h. According to one embodiment, lymphocytes and/or monocytes contained in the blood sample are stabilized. In one embodiment, the sterilized composition does not induce or promote the lysis of nucleated cells contained in the cell-containing sample. Thus, stabilization is not based on cell lysis. Preferably, when the cell containing sample is blood and the nucleic acid of interest is extracellular nucleic acid, in particular extracellular RNA, the sterilized stabilization composition prevents hemolysis. Most causes of in vitro hemolysis are related to specimen collection. However, in vitro hemolysis usually also occurs in a blood sample during ex vivo storage if no proper stabilization method is used. Depending on the extracellular nucleic acid of interest, hemolysis can be a considerable problem. If the extracellular nucleic acid of interest is DNA, hemolysis is less of a problem because red blood cells do not contain a nucleus and consequently, do not contain genomic DNA. Therefore, no intracellular DNA is released from the red blood cells during hemolysis. When the extracellular nucleic acid of interest is DNA, in particular the lysis or decay of white blood cells is a problem because in this case genomic DNA is released in addition to intracellular RNA. Therefore, when the extracellular nucleic acid of interest is extracellular DNA, in particular the lysis of white blood cells must be prevented. White blood cells may differ among each other in their stability characteristics. Thus, some types of white blood cells are more stable than others. However, generally, white blood cells are significantly more stable than red blood cells. Therefore, the lysis of red blood cells does not necessarily indicate that white blood cells were lysed. The different susceptibility of white blood cells and red blood cells to lysis is also used in the art to e.g. specifically lyse red blood cells, while preserving white cells in order to allow e. g. the collection of white blood cells. However, if the extracellular nucleic acid of interest is RNA, hemolysis and thus the lysis of red blood cells does constitute a problem. Mature red blood cells also do not contain RNA, however, their precursors (reticulocytes) do. Reticulocytes make up approximately 0.5% to 1% of the red blood cells and contain large amounts of globin RNA. Therefore, in particular when the extracellular nucleic acid of interest is RNA, a lysis of red blood cells and thus reticulocytes during storage should be prevented/reduced in order to reduce a dilution of the extracellular nucleic acid population, in particular the extracellular RNA population, with globin mRNA. In one embodiment, hemolysis can be efficiently prevented/reduced by the sterilized stabilizing composition (see e.g. WO 2014/146781 for suitable caspase inhibitor containing stabilizing compositions that can be sterilized using the teachings of the present invention). Thereby, the extracellular nucleic acid population is substantially preserved and furthermore, the stabilized blood sample, in particular the plasma or serum obtained from the stabilized blood sample, is due to the prevention of hemolysis and cell lysis in general also suitable for other standard laboratory analyses. Furthermore, prevention of lysis of white blood cells allows to isolate and analyse the respective cells. In particular, it allows isolating intracellular nucleic acids such as intracellular RNA from white blood cells or other preserved cells contained in the stabilized sample. Moreover, when stabilizing cells including non-nucleus cells (e.g. reticulocytes) and intracellular nucleic acids, one can e.g. also analyse the transcriptome of such non-nucleus cells.

C. Method for Isolating Extracellular Nucleic Acids

According to a third aspect, the present invention provides a method for isolating extracellular nucleic acids from a stabilized cell-containing biological sample comprising:
 a) stabilizing the cell-containing biological sample according to a method of the second aspect of the invention; and
 b) isolating extracellular nucleic acids.

In step a), the extracellular nucleic acid population comprised in the cell-containing sample is stabilized according to the method described in the second aspect of the present invention, wherein a sterilized stabilization composition as described above is used. It is referred to the above disclosure which also applies here.

If the cell-containing biological sample comprises large amounts of cells as is e.g. the case with whole blood, the cells are preferably separated from the remaining sample in order to obtain a cell-free, respectively cell-reduced or cell-depleted fraction of the stabilized sample from which the extracellular nucleic acids are then isolated in step b). Thus, according to one embodiment, cells are removed from the cell-containing sample between step a) and step b). This intermediate step may be obsolete if samples are processed which merely comprise minor amounts of residual cells such as e.g. plasma or serum and/or wherein the extracellular nucleic acid of interest is DNA. Due to the stabilization of the invention, the release of genomic DNA during the stabilization period from the contained cells is reduced or even prevented and furthermore, the fragmentation of genomic DNA is reduced because of the caspase inhibitor. Due to its considerably larger size, unfragmented genomic DNA can be distinguished from the smaller extracellular DNA. This allows e.g. to selectively isolate extracellular DNA even in the presence of unfragmented genomic DNA by using a size selective isolation protocol. However, in order to improve the results, it is preferred that cells (or potentially remaining cells) are removed from the stabilized sample prior to isolating the extracellular nucleic acids in step b) in order to reduce contaminations of the extracellular nucleic acid population with intracellular nucleic acids that would otherwise be released from the cells during nucleic acid isolation. To remove the contained cells is also advantageous if the extracellular nucleic acids of interest are RNA, because it can be difficult to distinguish intracellular RNA from extracellular RNA and furthermore, a dilution of the extracellular RNA can thereby be prevented. A cell removal step prior to step b) is generally advantageous and thus preferred, also if the extracellular nucleic acid of interest is DNA, because this allows to use standard nucleic acid isolation procedures in step b).

Depending on the type of cell-containing biological sample, cells, including residual cells, can be separated and removed e.g. by centrifugation, for example centrifugation at moderate speed, or by using means other than centrifugation, such as e.g. filtration, sedimentation or binding to surfaces e.g. on (optionally magnetic) particles if a centrifugation step is to be avoided. Respective cell separation methods are well-known in the prior art and thus, do not need to be described in detail. Respective cell removal steps can also be easily included into an automated sample preparation protocol. Respectively removed cells may also be processed further if desired. The cells can e.g. be stored, analysed and/or biomolecules such as e.g. nucleic acids or proteins can be isolated from the removed cells. Furthermore, intracellular nucleic acids (e.g. intracellular DNA and/or RNA) can be isolated from contained cells, e.g. after the cells were separated from the remaining sample. E.g. intracellular RNA can be isolated and used for gene expression analysis. For these embodiments, it is preferred that the sterilized composition also stabilizes intracellular nucleic acids, such as in particular RNA and/or cell characteristics as discussed above. It is referred to the respective disclosure.

Furthermore, it is also within the scope of the present invention to include further intermediate steps to work up the stabilized sample.

Extracellular nucleic acids are isolated in step b), preferably from the cell-free, respectively cell-depleted fraction of the stabilized sample, e.g. from supernatants or from plasma and/or serum in case the stabilized cell-containing sample was a blood sample. For isolating extracellular nucleic acids, any known nucleic acid isolation method can be used that is suitable for isolating nucleic acids from the stabilized sample, respectively the obtained cell-depleted sample. Examples for respective purification methods include but are not limited to extraction, solid-phase extraction, silica-based purification methods, magnetic particle-based purification, phenol-chloroform extraction, chromatography, anion-exchange chromatography (using anion-exchange surfaces), electrophoresis, filtration, precipitation and combinations thereof. It is also within the scope of the present invention to specifically isolate specific target extracellular nucleic acids, e.g. by using appropriate probes coupled to a solid support that enable a sequence specific binding. Also any other nucleic acid isolating technique known by the skilled person can be used. Exemplary methods for isolating extracellular nucleic acids are described in WO 2013/045432 A1, which is incorporated herein by reference. The methods for extracellular nucleic acid isolation of WO 2013/045432 A1 can be applied in the method according to the third aspect of the invention.

D. Method for Processing and/or Analyzing Extracellular Nucleic Acids

According to a fourth aspect, the present invention provides a method for processing and/or analyzing extracellular nucleic acids comprising:
 a) isolating extracellular nucleic acids from a stabilized cell-containing biological sample according to a method of the third aspect of the invention; and
 b) processing and/or analyzing the isolated extracellular nucleic acids.

The method according to the third aspect which is used in step a) to isolate extracellular nucleic acids is described above and it is referred to the respective disclosure which also applies here. In step b) the isolated extracellular nucleic acids are then analysed and/or further processed. This can be done using suitable assay and/or analytical methods. E.g. they can be identified, modified, contacted with at least one enzyme, amplified, reverse transcribed, cloned, sequenced, contacted with a probe, be detected (their presence or absence) and/or can be quantified. Respective methods are well-known in the prior art and are commonly applied in the medical, diagnostic and/or prognostic field in order to analyze extracellular nucleic acids (see also the detailed description in the background of the present invention). Thus, after extracellular nucleic acids were isolated in step a), they can be analyzed e.g. to identify the presence, absence or severity of a disease state including but not being limited to a multitude of neoplastic diseases, in particular premalignancies and malignancies such as different forms of tumors or cancers. E.g. the isolated extracellular nucleic acids can be analysed in order to detect diagnostic and/or prognostic markers (e.g., fetal- or tumor-derived extracellular nucleic acids) in many fields of application, including but not limited to non-invasive prenatal genetic testing respectively screening, disease screening, screening for chromosomal aberrations, trisomies, point mutations, pathogen screening, oncology, cancer screening, early stage cancer screening, cancer therapy monitoring, genetic testing (genotyping), infectious disease testing, injury diagnostics, trauma diagnostics, transplantation medicine or many other diseases and, hence, are of diagnostic and/or prognostic relevance. According to one embodiment, the isolated extracellular nucleic acids are analyzed to identify and/or characterize a disease or a fetal characteristic. Thus, as discussed above, the isolation method described herein may further comprise a step c) of nucleic acid analysis and/or processing.

Therefore, according to one embodiment, the isolated extracellular nucleic acids are analysed in step b) to identify, detect, screen for, monitor or exclude a disease and/or at least one fetal characteristic.

E. Method for Producing a Sterilizable Composition

According to a fifth aspect, the present invention provides a method for producing a sterilizable composition, wherein the composition in sterilized form is suitable for stabilizing an extracellular nucleic acid population of a biological sample, the method comprising:
 a) preparing a composition comprising:
  i. at least one caspase inhibitor, and
  ii. at least one compound selected from a thioalcohol (which preferably is N-acetyl-cysteine or glutathione), a water-soluble vitamin, and vitamin E or a derivative thereof.

The method can further comprise:
 b) sterilizing the composition.

The method can be used for producing a sterilizable composition as those provided in step a) of the first aspect of the invention or a sterilisable composition according to the sixth aspect of the invention. The sequence in which the components of the composition are contacted with one another is not limited. For example, but not as a limitation, the composition in step a) can be prepared by first preparing a composition comprising one or more caspase inhibitors and then adding the at least one compound selected from a thioalcohol (which preferably is N-acetyl-cysteine and/or glutathione), a water-soluble vitamin, and vitamin E or a derivative thereof to the composition. If desired, the at least one compound selected from a thioalcohol (which preferably is N-acetyl-cysteine and/or glutathione), a water-soluble vitamin, and vitamin E or a derivative thereof can also be added prior to adding the one or more caspase inhibitors. When a liquid composition (such as an aqueous composition) is prepared, the liquid (e.g. water) can be provided first for convenience, however this is not required. Likewise, the composition in step a) can e.g. be prepared by contacting the individual components of the composition to be prepared simultaneously or sequentially with one another in any order. So the components of the composition can be contacted with each other. They are preferably mixed to yield a liquid composition, preferably an aqueous composition. The liquid composition may be a homogenous mixture of only one phase but it is also within the scope of the present invention that a liquid composition comprises solid components such as e.g. precipitates. Step a) of the method according to the fifth aspect of the invention can correspond to step a) of the method according to the first aspect of the invention. It is referred to the above disclosure. There, also suitable and preferred embodiments of the stabilizing composition and the achievable stabilization characteristics are described.

According to optional step b), the composition is then sterilized. Sterilization can be achieved by irradiation or other suitable means. In particular, sterilization can be achieved as described above in conjunction with the method of the first aspect of the invention. It is referred to the above disclosure.

F. Sterilizable Compositions

According to a sixth aspect, the present invention provides a sterilizable composition, wherein the composition in sterilized form is suitable for stabilizing an extracellular nucleic acid population of a biological sample. The composition is a composition as provided in step a) of the method of the first aspect of the invention. Suitable sterilizable compositions according to the invention have been described above when discussing the method according to the first aspect and it is referred to the respective disclosure. It is in particular referred to the above disclosure regarding the details of that composition, in particular the comprised components, suitable and preferred embodiments therefor and suitable and preferred concentrations and other characteristics discussed above. In embodiments, the sterilizable composition is suitable to additionally stabilize intracellular nucleic acids (in particular intracellular RNA and/or intracellular DNA (e.g. genomic DNA)). In embodiments, the sterilizable composition is suitable to additionally stabilize cell characteristics, such as e.g. cell surface characteristics and/or the cell morphology. Details were described above and it is referred to the above disclosure.

Preferably, the composition is sterilized. As discussed, sterilization by irradiation such as gamma irradiation is preferred. According to one embodiment, the composition is a sterilized composition obtainable and/or obtained by the method according to the first aspect of the invention. A sterilized composition suitable for stabilizing an extracellular nucleic acid population of a biological sample prepared with a method according to the first aspect of the invention therefore is contemplated and preferred.

Preferably, the composition is a liquid, more preferably the composition is aqueous.

The sterilizable compositions of the sixth aspect of the invention can be used for stabilizing the extracellular nucleic acid population in a cell-containing biological sample, preferably a blood sample. In embodiments, the sterilizable compositions can be used to additionally stabilize intracellular nucleic acids (in particular intracellular RNA and/or intracellular DNA), preferable the gene expression profile. In embodiments, the sterilizable composition can be used to additionally stabilize cell characteristics, such as e.g. cell surface characteristics and/or the cell morphology. It is referred to the above disclosure.

Advantageously, the compositions are used in sterilized form.

G. Collection Devices

According to a seventh aspect of the invention, a collection device for collecting a cell-containing biological sample, preferably a blood sample, is also provided. The collection device is subsequently also referred to as container.

The device comprises the composition according to the sixth aspect of the invention. Therefore, the composition comprised in the device can be a composition provided in step a) of the method according to the first aspect of the invention. It is referred to the above disclosure for details.

Accordingly in one embodiment, the collection device comprises a composition, which preferably is liquid, more preferably aqueous, and that comprises:
  a) one or more caspase inhibitors,
  b) one or more compound selected from a thioalcohol (which preferably is N-acetyl-cysteine or glutathione), a water-soluble vitamin, and vitamin E or a derivative thereof as discussed above, wherein, preferably, the composition comprises N-acetyl-cysteine,
  c) at least one poly(oxyethylene) polymer, which preferably is a high molecular weight poly(oxyethylene) polymer having a molecular weight of at least 1500, as stabilizing agent,
  and optionally one or more, preferably two or more further additives selected from the group consisting of:
  d) at least one further poly(oxyethylene) polymer having a molecular weight that is at least 100, preferably at least 200, at least 300 or at least 400 below the molecular weight of the first poly(oxyethylene) polymer, which preferably is a high molecular weight poly(oxyethylene) polymer, wherein said further poly(oxyethylene) polymer preferably is a low molecular weight poly(oxyethylene) polymer having a molecular weight of 1000 or less;
  e) at least one primary, secondary or tertiary amide;
  f) an anticoagulant and/or a chelating agent.

Preferably, the stabilization composition comprises one or more of the compounds according to the invention in concentrations as disclosed above in the first aspect of the invention when discussing feature ii, more preferably as disclosed above in Table A. Suitable compounds and concentrations are also shown in Table B. The use of N-acetyl-cysteine is particularly preferred.

Accordingly in one embodiment, the collection device comprises a composition, which preferably is liquid, more preferably aqueous, and that comprises:
  a) one or more caspase inhibitors, preferably a pancaspase inhibitor, more preferred a caspase inhibitor comprising a modified caspase-specific peptide, even more preferred a caspase inhibitor selected from the group consisting of Q-VD-OPh, Z-VAD(OMe)-FMK and Boc-D-(OMe)-FMK, most preferably Q-VD-OPh;
  b) one or more compound selected from a thioalcohol (which preferably is N-acetyl-cysteine or glutathione), a water-soluble vitamin (which preferably is Vitamin B6 or ascorbic acid), and vitamin E or a derivative thereof as discussed above, wherein, preferably, the composition comprises N-acetyl-cysteine,
  c) at least one poly(oxyethylene) polymer as stabilizing agent, wherein preferably the poly(oxyethylene) polymer is a polyethylene glycol, more preferably an unsubstituted polyethylene glycol;
  and optionally one or more, preferably two further additives selected from the group consisting of:
  d) at least one primary, secondary or tertiary amide;
  e) an anticoagulant and/or a chelating agent.

In embodiments, the at least one poly(oxyethylene) polymer, which preferably is a polyethylene glycol, is selected from a low molecular weight poly(oxyethylene) polymer, preferably a low molecular weight poly(oxyethylene) polymer having a molecular weight of 1000 or less, and/or a high molecular weight poly(oxyethylene) polymer having a molecular weight of at least 1500.

Preferably, the stabilization composition comprises one or more of the compounds according to the invention in concentrations as disclosed above when discussing feature ii, more preferably as disclosed above in Table A or Table B. The use of N-acetyl-cysteine is particularly preferred.

In a further embodiment, the collection device comprises a stabilization composition, which preferably is liquid, more preferably aqueous, and that comprises:
- a) at least one caspase inhibitor, preferably a pancaspase inhibitor, more preferably a caspase inhibitor comprising a modified caspase-specific peptide. Said caspase-specific peptide can be modified by an aldehyde, nitrile or ketone compound. According to one embodiment, the caspase specific peptide is modified, preferably at the carboxyl terminus, with an O-Phenoxy (OPh) or a fluoromethyl ketone (FMK) group. According to one embodiment, the caspase inhibitor is selected from the group consisting of Q-VD-OPh, Boc-D-(OMe)-FMK and Z-VAD(OMe)-FMK. According to one embodiment, the caspase inhibitor is selected from the group consisting of Q-VD-OPh and Z-VAD(OMe)-FMK, most preferred Q-VD-OPh.
- b) one or more of the following compounds:
  N-acetyl-cysteine in a concentration of 0.05 mg/ml to 15 mg/ml, 0.1 mg/ml to 10 mg/ml, 0.1 mg/ml to 7.5 mg/ml, 0.1 mg/ml to 5 mg/ml, 0.1 mg/ml to 2 mg/ml, 0.2 mg/ml to 1 mg/ml, or 0.3 mg/ml to 0.8 mg/ml,
  glutathione in reduced form in a concentration of 0.03 mg/ml to 10 mg/ml, 0.04 mg/ml to 7.5 mg/ml, 0.075 mg/ml to 5 mg/ml, 0.15 mg/ml to 4 mg/ml, 0.3 mg/ml to 3 mg, 0.4 mg/ml to 2 mg/ml, or 0.4 mg/ml to 1.3 mg/ml and/or
  ascorbic acid in a concentration of less than 20 mg/ml, such as 1 mg/ml to 15 mg/ml, 0.2 mg/ml to 14 mg/ml, 0.5 mg/ml to 13.5 mg/ml, 1 mg/ml to 13 mg/ml, 1.5 mg/ml to 12 mg/ml, or 2 mg/ml to 11 mg/ml,
  a B vitamin, preferably vitamin B6, in a concentration of 0.1 mg/ml to 15 mg/ml, 0.1 mg/ml to 14 mg/ml, 0.1 mg/ml to 11 mg/ml, 0.2 mg/ml to 7.5 mg/ml, or 0.2 mg/ml to 2 mg/ml,
  the composition optionally further comprising one or more components selected from:
- c) at least one poly(oxyethylene) polymer as stabilizing agent, wherein preferably the poly(oxyethylene) polymer is a polyethylene glycol, more preferably an unsubstituted polyethylene glycol,
- d) at least one primary, secondary or tertiary amide, preferably an N,N-dialkylpropanamide (e.g. N,N-dimethylpropanamide) and/or butanamide, and
- e) an anticoagulant and/or a chelating agent, preferably EDTA.

In embodiments, the at least one poly(oxyethylene) polymer, which preferably is a polyethylene glycol, is selected from a low molecular weight poly(oxyethylene) polymer, preferably a low molecular weight poly(oxyethylene) polymer having a molecular weight of 1000 or less, and/or a high molecular weight poly(oxyethylene) polymer having a molecular weight of at least 1500.

In a further embodiment, the collection device comprises a stabilization composition, which preferably is liquid, more preferably aqueous, and that comprises:
- a) at least one caspase inhibitor, preferably a pancaspase inhibitor, more preferably a caspase inhibitor comprising a modified caspase-specific peptide. Said caspase-specific peptide can be modified by an aldehyde, nitrile or ketone compound. According to one embodiment, the caspase specific peptide is modified, preferably at the carboxyl terminus, with an O-Phenoxy (OPh) or a fluoromethyl ketone (FMK) group. According to one embodiment, the caspase inhibitor is selected from the group consisting of Q-VD-OPh, Boc-D-(OMe)-FMK and Z-VAD(OMe)-FMK. According to one embodiment, the caspase inhibitor is selected from the group consisting of Q-VD-OPh and Z-VAD(OMe)-FMK, most preferred Q-VD-OPh.
- b) one or more of the following compounds:
  N-acetyl-cysteine in a concentration of 0.05 mg/ml to 15 mg/ml, 0.1 mg/ml to 10 mg/ml, 0.1 mg/ml to 7.5 mg/ml, 0.1 mg/ml to 5 mg/ml, 0.1 mg/ml to 2 mg/ml, 0.2 mg/ml to 1 mg/ml, or 0.3 mg/ml to 0.8 mg/ml,
  glutathione in reduced form in a concentration of 0.03 mg/ml to 10 mg/ml, 0.04 mg/ml to 7.5 mg/ml, 0.075 mg/ml to 5 mg/ml, 0.15 mg/ml to 4 mg/ml, 0.3 mg/ml to 3 mg, 0.4 mg/ml to 2 mg/ml, or 0.4 mg/ml to 1.3 mg/ml and/or
  ascorbic acid in a concentration of less than 20 mg/ml, such as 0.1 mg/ml to 15 mg/ml, 0.2 mg/ml to 14 mg/ml, 0.5 mg/ml to 13.5 mg/ml, 1 mg/ml to 13 mg/ml, 1.5 mg/ml to 12 mg/ml, or 2 mg/ml to 11 mg/ml, the composition optionally further comprising one or more components selected from:
- c) at least one high molecular weight poly(oxyethylene) polymer having a molecular weight of at least 1500, preferably in a range of 2000 to 40000, more preferred 2500 to 30000, 2500 to 25000 or 3000 to 20000,
- d) at least one primary, secondary or tertiary amide, preferably an N,N-dialkylpropanamide (e.g. N,N-dimethylpropanamide) and/or butanamide,
- e) at least one further poly(oxyethylene) polymer having a molecular weight that is at least 100, preferably at least 200, at least 300 or at least 400 below the molecular weight of the high molecular weight poly(oxyethylene) polymer used and wherein said further poly(oxyethylene) polymer preferably is a low molecular weight poly(oxyethylene) having a molecular weight of 1000 or less, preferably having a molecular weight in a range of 200 to 800 or 200 to 600, and
- f) an anticoagulant and/or a chelating agent, preferably EDTA.

In a further embodiment, the collection device comprises a stabilization composition, which preferably is liquid, more preferably aqueous, and that comprises:
- a) at least one pancaspase inhibitor, more preferred more preferably a caspase inhibitor comprising a modified caspase-specific peptide as described above, most preferred Q-VD-OPh,
- b) N-acetyl-cysteine in a concentration of 0.05 mg/ml to 15 mg/ml, 0.1 mg/ml to 10 mg/ml, 0.1 mg/ml to 7.5 mg/ml, 0.1 mg/ml to 5 mg/ml, 0.1 mg/ml to 2 mg/ml, 0.2 mg/ml to 1 mg/ml, or 0.3 mg/ml to 0.8 mg/ml;

the composition optionally further comprising:
- c) at least one poly(oxyethylene) polymer as stabilizing agent, wherein preferably the poly(oxyethylene) polymer is a polyethylene glycol, more preferably an unsubstituted polyethylene glycol,
- d) at least one primary, secondary or tertiary amide, preferably an N,N-dialkylpropanamide (e.g. N,N-dimethylpropanamide) and/or butanamide, and
- e) an anticoagulant and/or a chelating agent, preferably EDTA.

In embodiments, the at least one poly(oxyethylene) polymer, which preferably is a polyethylene glycol, is selected from a low molecular weight poly(oxyethylene) polymer, preferably a low molecular weight poly(oxyethylene) polymer having a molecular weight of 1000 or less, and/or a high molecular weight poly(oxyethylene) polymer having a molecular weight of at least 1500.

In a further embodiment, the collection device comprises a stabilization composition, which preferably is liquid, more preferably aqueous, and that comprises:
a) at least one pancaspase inhibitor, more preferred more preferably a caspase inhibitor comprising a modified caspase-specific peptide as described above, most preferred Q-VD-OPh,
b) N-acetyl-cysteine in a concentration of 0.05 mg/ml to 15 mg/ml, 0.1 mg/ml to 10 mg/ml, 0.1 mg/ml to 7.5 mg/ml, 0.1 mg/ml to 5 mg/ml, 0.1 mg/ml to 2 mg/ml, 0.2 mg/ml to 1 mg/ml, or 0.3 mg/ml to 0.8 mg/ml;

the composition optionally further comprising:
c) at least one high molecular weight poly(oxyethylene) polymer having a molecular weight of at least 1500, preferably in a range of 2000 to 40000, more preferred 2500 to 30000, 2500 to 25000 or 3000 to 20000,
d) at least one primary, secondary or tertiary amide, preferably an N,N-dialkylpropanamide (e.g. N,N-dimethylpropanamide) and/or butanamide,
e) at least one further poly(oxyethylene) polymer having a molecular weight that is at least 100, preferably at least 200, at least 300 or at least 400 below the molecular weight of the high molecular weight poly(oxyethylene) polymer used and wherein said further poly(oxyethylene) polymer preferably is a low molecular weight poly(oxyethylene) having a molecular weight of 1000 or less, preferably having a molecular weight in a range of 200 to 800 or 200 to 600, and
f) optionally an anticoagulant and/or a chelating agent, preferably EDTA.

The composition comprised in the collection device can be provided and e.g. prepared as described in step a) of the method according to the first aspect of the invention, either directly in the collection device, or it can be filled into the collection device after preparation.

Providing a respective collection device, e.g. a container, such as a sample collection tube, preferably a blood collection tube, comprising a composition according to the sixth aspect of the invention has the advantage that the cell-containing biological sample is immediately stabilized as soon as the sample is collected in the respective device.

The stabilizing composition and/or the individual compounds used for stabilization comprised in the collection container can be provided in a liquid, semi-liquid or in a dry form. The compounds used for stabilization may also be provided as separate entities in the container and may also be provided in different forms in the container. E.g. one component may be provided in dry form while the other compound may be provided as liquid. Other combinations are also feasible. Suitable formulation and manufacturing options are known to the skilled person. The advantage of using a solid stabilizing composition is that solids are usually chemically more stable than liquids. According to one embodiment, the inner wall of the container is treated/covered with a stabilizing composition according to the present invention or with individual components thereof, such as e.g. the anticoagulant. Said composition or component can be applied to the inner walls using e.g. a spray-dry-method. Liquid removal techniques can be performed on the stabilizing composition in order to obtain a substantially solid state protective composition. Such liquid removal conditions and techniques are described in PCT/EP2015/055699 and reference is made to this disclosure.

As explained above, it is however preferred that the stabilizing composition is provided in a liquid, preferably aqueous form. This has advantages with regard to sterilization by irradiation, and also has advantages for specific samples such as e.g. blood samples. Liquid compositions have the advantage that the mixture with the cell-containing biological sample to be stabilised can be quickly achieved, thereby basically providing an immediate stabilizing effect as soon as the sample comes into contact with the liquid stabilizing composition. Furthermore, liquid compositions are advantageous if larger amounts of stabilization compositions are used which accordingly, cannot or are difficult to spray-dry or if the composition hampers providing a dry composition.

The stabilizing composition is comprised in the container in an amount effective to provide the stabilization of the amount of sample to be collected in said container. According to one embodiment, the liquid stabilizing composition is contacted with the biological sample in a volumetric ratio selected from 10:1 to 1:20, 5:1 to 1:15, 1:1 to 1:10, 1:4 to 1:10 and 1:5 to 1:9, in particular about 1:6 to 1:8.

Preferably, the collection device is sterilizable, more preferably it is sterilizable using the method according to the first aspect of the invention. Again, it is referred to the above disclosure in the first aspect of the invention for details, which also apply here. Accordingly, irradiating the collection device comprising the composition in a liquid, preferably aqueous, form is very preferred. If the collection device initially comprises the composition in a solid form, the composition can be brought into a liquid form prior to irradiation.

The device and the composition comprised therein can be sterilized together, e.g. in a method according to the first aspect of the invention. This advantageously allows to provide a sterilized end-product ready for sample collection.

Thus preferably, the device is sterilized. More preferably, the device is a sterilized device obtainable and/or obtained by a method according to the first aspect of the invention. A device comprising a sterilized composition suitable for stabilizing an extracellular nucleic acid population of a biological sample prepared with a method according to the first aspect of the invention therefore is contemplated and preferred.

The collection device can be evacuated. The evacuation is preferably effective for drawing a specific volume of a fluid cell-containing biological sample into the interior. Thereby, it is ensured that the correct amount of sample is contacted with the pre-filled amount of the stabilizing composition comprised in the container, and accordingly, that the stabilization is efficient. According to one embodiment, the container comprises a tube having an open end sealed by a septum. E.g. the container is pre-filled with a defined amount of the stabilizing composition either in solid or liquid form and is provided with a defined vacuum and sealed with a septum. The septum is constructed such that it is compatible with the standard sampling accessories (e.g. cannula, etc.). When contacted with e.g. the cannula, a sample amount that is predetermined by the vacuum is collected in the container. A respective embodiment is in particular advantageous for collecting blood. A suitable container is e.g. disclosed in U.S. Pat. No. 6,776,959.

The container can be made of glass, plastic or other suitable materials. Plastic materials can be oxygen impermeable materials or may contain an oxygen impermeable layer. Alternatively, the container can be made of air-permeable plastic material. The container according to the present invention preferably is made of a transparent material. Examples of suitable transparent thermoplastic materials include polycarbonates, polyethylene, polypropylene and polyethyleneterephthalate. The container may have a suitable dimension selected according to the required volume of the biological sample being collected. As described above, preferably, the container is evacuated to an internal pressure below atmospheric pressure. Such an embodiment is particularly suitable for collecting body fluids such as whole blood. The pressure is preferably selected to draw a predetermined volume of a biological sample into the container. In addition to such vacuum tubes also non-vacuum tubes, mechanical separator tubes or gel-barrier tubes can be used as sample containers, in particular for the collection of blood samples. Examples of suitable containers and capping devices are disclosed in U.S. Pat. No. 5,860,397 and US 2004/0043505. As container for collecting the cell-containing sample also further collection devices, for example a syringe, a urine collection device or other collection devices can be used. The type of the container may also depend on the sample type to be collected and suitable containers are also available to the skilled person.

According to one embodiment, the container has an open top, a bottom, and a sidewall extending there between defining a chamber, wherein a composition according to the sixth aspect of the invention or a composition provided in step a) of the method according to the first aspect of the invention is comprised in the chamber. It may be comprised therein in liquid or solid form. According to one embodiment, it is a liquid, preferably an aqueous liquid. According to one embodiment the container is a tube, the bottom is a closed bottom, the container further comprises a closure in the open top, and the chamber is at a reduced pressure. The advantages of a reduced pressure in the chamber were described above. Preferably, the closure is capable of being pierced with a needle or cannula, and the reduced pressure is selected to draw a specified volume of a liquid sample into the chamber. According to one embodiment, the chamber is at a reduced pressure selected to draw a specified volume of a liquid sample into the chamber, and the stabilizing composition is a liquid and is disposed in the chamber such that the volumetric ratio of the stabilizing composition to the specified volume of the cell-containing sample is selected from 10:1 to 1:20, 5:1 to 1:15 and 1:1 to 1:10 and preferably is 1:5 to 1:10, more preferably 1:6 to 1:8. The associated advantages were described above and are also discussed in PCT/EP2015/055699.

Preferably, the container is for drawing blood from a patient. According to one embodiment, it is for drawing 10 ml blood from a patient. According to one embodiment, the stabilisation composition is a liquid and the volume is 2 ml or less and may lie in a range of 0.5 ml to 2 ml, 0.75 ml to 1.75 ml and 1 ml to 1.5 ml.

Also provided is a method comprising the step of collecting, preferably drawing, a biological sample, preferably blood, from a patient directly into a chamber of a device or container according to the seventh aspect of the present invention.

H. Kits

According to an eights aspect, the present invention provides a kit comprising a composition according to the sixth aspect of the invention or a collection device according to the seventh aspect of the invention. The kit can further comprise further components, such as reagents for isolating extracellular nucleic acids.

I. Uses

According to a ninth aspect, the present invention is directed to the use of at least one compound selected from the group consisting of a thioalcohol (preferably N-acetyl-cysteine or glutathione), a water-soluble vitamin, and vitamin E or a derivative thereof, for protecting a composition suitable for stabilizing an extracellular nucleic acid population of a biological sample or components thereof during sterilization, in particular sterilization by irradiation.

These compounds are in particular suitable as discussed above to protect a contained caspase inhibitor during irradiation from degradation. The degree of degradation is significantly reduced when using one or more of these compounds. Irradiation can be preferably ionizing irradiation, more preferably gamma irradiation, electron beam irradiation, or X-ray, gamma irradiation being most preferred. The irradiation and/or sterilization conditions applied can be as discussed above in relation with the first aspect of the invention.

The disclosure of the method according to the first aspect of the invention regarding suitable compounds of the invention and combinations of compounds as well as suitable concentrations also applies for the present aspect. The compound can for example be selected from N-acetyl-cysteine, glutathione (preferably in reduced form), ascorbic acid, and/or trolox. N-acetyl-cysteine is highly preferred. Suitable concentrations are also described above and the compounds can for example and without limitation be applied in a concentration as indicated in Table A above. Suitable concentrations are also indicated in Table B above.

The caspase inhibitor can in particular be selected from the group consisting of Q-VD-OPh, Boc-D-(OMe)-FMK and Z-VAD(OMe)-FMK. The caspase inhibitor can be selected from Q-VD-OPh and Z-VAD(OMe)-FMK, most preferably, the caspase inhibitor is Q-VD-OPh.

J. Further Aspects

According to a tenth aspect, the present invention provides for the use of at least one radical scavenger in protecting an aqueous composition comprised in a sample collection device, in particular a blood collection tube, during irradiation.

According to an eleventh aspect, a method of sterilizing an aqueous composition comprised in a sample collection device is provided, the method comprising:

a) preparing an aqueous composition comprising at least one radical scavenger comprised in the sample collection device, and b) sterilizing the composition by irradiation.

The aqueous composition of the tenth and eleventh aspect of the invention can be a composition for stabilizing a component comprised in a biological sample, such as a cell containing biological sample, preferably blood. Examples of biological samples of interest have been described in the first aspect of the invention, and the samples stabilized by the aqueous composition can be such samples. Preferably, the aqueous composition to be protected comprises a caspase inhibitor. The caspase inhibitor can be an inhibitor as disclosed in WO 2013/045457 A1 or WO 2013/045458 A1. Suitable caspase inhibitors and concentrations have been disclosed above in the first aspect of the invention. Reference is made to this disclosure, which also applies here. Also, suitable and preferred aqueous compositions have been disclosed above in the first aspect of the invention. This disclosure also applies here, meaning that aqueous compositions according to the first aspect are examples of aqueous compositions that can be used in the tenth and eleventh aspect of the invention. The aqueous composition in particular can be a composition for stabilizing circulating tumor cells, circulating cell-free RNA, circulating cell-free miRNA, viruses and/or exosomes. Stabilization can facilitate subsequent isolation, analysis and/or diagnostics. Circulating tumor cells are a particular concern in mammals and humans suffering from cancer. Analysis of circulating tumor cells can e.g. provide information on the tumor burden, tumor stage and/or on formation of distant metastasis. Circulating cell-free RNA and circulating cell-free miRNA are examples of extracellular nucleic acid populations. Viruses can be for example contained in a biological sample from a mammal or human infected by the virus. Exosomes are cell-derived vesicles that are present in many biological fluids, including blood and urine. Exosomes are e.g. involved in coagulation and intercellular signaling. Analysis of cell free RNA and miRNA can be used to identify circulating biomarkers, detection of somatic mutations and oncogene expression. In embodiments, the sterilized aqueous composition is suitable to stabilize intracellular nucleic acids (in particular intracellular RNA and/or intracellular DNA). In embodiments, the sterilized aqueous composition is suitable to additionally stabilize cell characteristics, such as e.g. cell surface characteristics and/or the cell morphology. Details of such compositions and stabilization characteristics were described above and it is referred to the above disclosure which also applies here.

The at least one radical scavenger according to the tenth and eleventh aspect can be a compound capable of reacting with a free radical in a biological system. It can in particular be at least one compound selected from a thiol (such as N-acetyl-cysteine or glutathione), a water-soluble vitamin, and vitamin E or a derivative thereof as described in the first aspect of the invention. Suitable compounds and concentrations can be as described in the first aspect of the invention and apply. Preferably, the at least one radical scavenger is active to protect the aqueous composition during irradiation so as to reduce or eliminate a reduction of stabilization function of the aqueous composition due to irradiation. Activity in reducing or eliminate a reduction of stabilization function can be determined by comparing the stabilization functions of a sterilized aqueous composition comprising the at least one radical scavenger and of an aqueous composition sterilized under identical compositions and differing from the composition to be tested preferably only in that the at least one radical scavenger is not comprised.

Suitable sample collection devices that can be used in the tenth and eleventh aspect of the invention have been described above in the seventh aspect of the invention, and this description also applies here. Accordingly, the collection device can be evacuated. It can be made of glass, plastic or other suitable materials. According to one embodiment, the collection device or container can have an open top, a bottom, and a sidewall extending there between defining a chamber, wherein the aqueous composition is comprised.

The method for isolating extracellular nucleic acids from a stabilized cell-containing biological sample such as e.g. a blood sample has been described above in conjunction with the third aspect. According to a further aspect, a method for isolating nucleic acids from a stabilized cell-containing biological sample is provided comprising
  a) stabilizing a cell-containing biological sample, wherein stabilization comprises
    i) obtaining a sterilized composition according to a method of the first aspect of the invention; or
    ii) obtaining a composition according to the sixth aspect of the invention, wherein the composition is sterilized; or
    iii) obtaining a sample collection device according to the seventh aspect of the invention, wherein the composition comprised therein is sterilized;
    and contacting the cell-containing biological sample with the sterilized composition; and
  b) isolating nucleic acids from the stabilized sample.

Details regarding the sterilized stabilizing compositions and their stabilizing properties were described in detail above and it is referred to the above disclosure which also applies here. In step b), intracellular nucleic acids and/or extracellular nucleic acids can be isolated from the stabilized sample. Suitable isolation methods were described above in conjunction with the third aspect of the present invention and it is referred to the respective disclosure which also applies here. In embodiments, cells are removed from the cell-containing stabilized sample prior to isolating the nucleic acids. In embodiments, intracellular nucleic acids (e.g. DNA and/or RNA) are isolated from contained cells, e.g. after the cells were separated from the remaining sample. E.g. RNA can be isolated and used for gene expression analysis. Details were described above and it is referred to the respective disclosure.

The isolated nucleic acids can then be analyzed and/or further processed in a step c) using suitable assay and/or analytical methods.

According to a further aspect, a method for isolating cells from a stabilized cell-containing biological sample is provided comprising
  a) stabilizing a cell-containing biological sample, wherein stabilization comprises
    i) obtaining a sterilized composition according to a method of the first aspect of the invention; or
    ii) obtaining a composition according to the sixth aspect of the invention, wherein the composition is sterilized; or
    iii) obtaining a sample collection device according to the seventh aspect of the invention, wherein the composition comprised therein is sterilized;
    and contacting the cell-containing biological sample with the sterilized composition; and
  b) isolating cells from the stabilized sample.

The isolated cells can be e.g. further analysed. As discussed above, in embodiments, the sterilized stabilizing composition also preserves cell surface characteristics (e.g. cell surface epitopes or proteins) and/or the cell morphology. Details were described above and it is referred to the above disclosure which also applies here.

According to a further aspect, a method is provided comprising the step of collecting a sample from a patient directly into a chamber of a collection device according to the seventh aspect of the present invention. Details with respect to the collection device and the sample were described above. It is referred to the respective disclosure. According to one embodiment, a blood sample is collected, preferably it is withdrawn from the patient.

This invention is not limited by the exemplary methods and materials disclosed herein, and any methods and materials similar or equivalent to those described herein can be used in the practice or testing of embodiments of this invention. Numeric ranges are inclusive of the numbers defining the range. The headings provided herein are not limitations of the various aspects or embodiments of this invention which can be read by reference to the specification as a whole.

As used in the subject specification and claims, the singular forms "a", "an" and "the" include plural aspects unless the context clearly dictates otherwise. Thus, for example, reference to "a caspase inhibitor" includes a single type of caspase inhibitor, as well as two or more caspase inhibitors. Reference to "the disclosure" and "the invention"

and the like includes single or multiple aspects taught herein; and so forth. Aspects taught herein are encompassed by the term "invention".

As used in the present specification, the expression "about" is intended to signify the given value±10%.

According to one embodiment, subject matter described herein as comprising certain steps in the case of methods or as comprising certain ingredients in the case of compositions, solutions and/or buffers refers to subject matter consisting of the respective steps or ingredients. It is preferred to select and combine preferred embodiments described herein and the specific subject-matter arising from a respective combination of preferred embodiments also belongs to the present disclosure.

Also disclosed are the following items:

1. A method for producing a sterilized composition suitable for stabilizing an extracellular nucleic acid population of a biological sample, the method comprising:
   a) providing a composition comprising:
      i. at least one caspase inhibitor, and
      ii. at least one compound selected from a thioalcohol and a vitamin or a derivative thereof; and
   b) irradiating the composition for sterilization.
2. The method of item 1, the method comprising:
   a) providing a composition comprising:
      i. at least one caspase inhibitor, and
      ii. at least one compound selected from a thioalcohol, a water-soluble vitamin or a derivative thereof, and a water-soluble derivate of a fat-soluble vitamin; and
   b) irradiating the composition for sterilization.
3. The method of item 1 or 2, the method comprising:
   a) providing a composition comprising:
      i. at least one caspase inhibitor, and
      ii. at least one compound selected from a thioalcohol that is N-acetyl-cysteine or glutathione, a water-soluble vitamin or a derivative thereof, and a water-soluble derivate of a fat-soluble vitamin, optionally wherein the at least one compound is selected from a thioalcohol that is N-acetyl-cysteine or glutathione, a water-soluble vitamin, and a water-soluble vitamin E derivate; and
   b) irradiating the composition for sterilization.
4. The method according to one or more of items 1 to 3, wherein irradiating the composition for sterilization has one or more of the following characteristics:
   a) the composition is irradiated by ionizing irradiation;
   b) the composition is irradiated by gamma irradiation, electron beam irradiation, or X-ray;
   c) the composition is irradiated by gamma irradiation or X-ray;
   d) the composition is irradiated by gamma irradiation;
   e) the composition is irradiated with an irradiation dose of 5 kGy to 35 kGy, 6 kGy to 30 kGy, 7 kGy to 26 kGy, about 8 kGy to about 25 kGy, or about 8 kGy to about 15 kGy;
   f) the composition is irradiated by gamma irradiation with an irradiation dose of 5 kGy to 35 kGy, 6 kGy to 30 kGy, 7 kGy to 26 kGy, about 8 kGy to about 25 kGy, or about 8 kGy to about 15 kGy;
   g) the composition is irradiated by gamma irradiation with an irradiation dose of 8 kGy to 25 kGy, or 8 kGy to 15 kGy; and/or
   h) sterilization by irradiation results in a sterility assurance level (SAL) of the composition of $10^{-6}$ or less.
5. The method according to one or more of items 1 to 4, wherein the composition has one or more of the following characteristics:
   a) the composition is prepared in solid form;
   b) the composition is prepared in solid form and is dissolved prior to irradiation to provide a liquid composition which is preferably aqueous;
   d) the composition is prepared and irradiated in a liquid form;
   e) the composition is aqueous;
   f) the composition has an acidic pH;
   g) the composition has a pH of 4.0 to 7.0, a pH of 4.1 to 6.9, a pH of 4.2 to 6.8, a pH of 4.3 to 6.6, a pH of 4.4 to 6.3, a pH of 4.5 to 6.0, or a pH of 4.5 to 5.5 and/or
   h) the composition is buffered.
6. The method according to one or more of items 1 to 5, comprising irradiating the composition in a liquid, preferably aqueous, form.
7. The method according to one or more of items 1 to 6, wherein the composition comprises the at least one compound selected from a thioalcohol that is N-acetyl-cysteine or glutathione, a water-soluble vitamin or a derivative thereof, and a water-soluble derivative of a fat-soluble vitamin in a concentration of less than 20 mg/ml, 15 mg/ml or less, 10 mg/ml or less, 7 mg/ml or less, 3 mg/ml or less, or 1.5 mg/ml or less.
8. The method according to one or more of items 1 to 7, wherein the composition comprises
   i. a compound selected from N-acetyl-cysteine, glutathione, wherein the glutathione is preferably in reduced form, a B vitamin, preferably vitamin B6, ascorbic acid or a derivative thereof, and trolox;
   ii. a compound selected from N-acetyl-cysteine, glutathione, ascorbic acid or a derivative thereof, and trolox, wherein the glutathione is preferably in reduced form;
   iii. a compound selected from N-acetyl-cysteine, glutathione, wherein the glutathione is preferably in reduced form, a B vitamin, preferably vitamin B6, and ascorbic acid;
   iv. a compound selected from N-acetyl-cysteine, glutathione, and ascorbic acid or a derivative thereof, wherein the glutathione is preferably in reduced form; or
   v. N-acetyl-cysteine.
9. The method according to one or more of items 1 to 8, the method comprising:
   a) providing a composition comprising:
      i. at least one caspase inhibitor, preferably as defined in item 15, and
      ii. at least one of
         aa) N-acetyl-cysteine in a concentration of 0.05 mg/ml to 15 mg/ml, 0.1 mg/ml to 10 mg/ml, 0.1 mg/ml to 7.5 mg/ml, 0.1 mg/ml to 5 mg/ml, 0.1 mg/ml to 2 mg/ml, 0.2 mg/ml to 1 mg/ml, or 0.3 mg/ml to 0.8 mg/ml;
         ab) glutathione in a concentration of 0.03 mg/ml to 10 mg/ml, 0.04 mg/ml to 7.5 mg/ml, 0.075 mg/ml to 5 mg/ml, 0.15 mg/ml to 4 mg/ml, 0.3 mg/ml to 3 mg, 0.4 mg/ml to 2 mg/ml, or 0.4 mg/ml to 1.3 mg/ml, wherein the glutathione is preferably in reduced form;
         ac) ascorbic acid or a derivative thereof in a concentration of less than 20 mg/ml, such as 0.1 mg/ml to 15 mg/ml, 1 mg/ml to 13 mg/ml, 1.5 mg/ml to 12 mg/ml, or 2 mg/ml to 11 mg/ml;
         ad) a B vitamin, preferably vitamin B6, in a concentration of 0.1 mg/ml to 15 mg/ml, 0.1 mg/ml to 14 mg/ml, 0.1 mg/ml to 11 mg/ml, 0.2 mg/ml to 7.5 mg/ml, or 0.2 mg/ml to 2 mg/ml;

ae) trolox in a concentration of 0.5 mg/ml to 5 mg/ml, 0.75 mg/ml to 3 mg/ml, 0.9 mg/ml to 2 mg/ml, or 1 mg/ml to 1.4 mg/ml; and
b) irradiating the composition for sterilization,
wherein preferably, the composition comprises N-acetyl-cysteine in a concentration as defined in aa).

10. The method according to item 9, wherein the composition is irradiated in a liquid, preferably aqueous form and/or wherein the composition is irradiated by gamma irradiation for sterilization.

11. The method according to one or more of items 1 to 10, wherein the composition has one or more of the following characteristics:
   a) the composition comprises N-acetyl-cysteine;
   b) the composition comprises N-acetyl-cysteine in a concentration of 0.05 mg/ml to 15 mg/ml, 0.1 mg/ml to 10 mg/ml, 0.1 mg/ml to 7.5 mg/ml, 0.1 mg/ml to 5 mg/ml, 0.1 mg/ml to 2 mg/ml, 0.2 mg/ml to 1 mg/ml, or 0.3 mg/ml to 0.8 mg/ml;
   c) the composition comprises N-acetyl-cysteine and is sterilized by irradiation in a liquid, preferably aqueous, form; and/or
   d) the composition comprises N-acetyl-cysteine in a concentration of 0.05 mg/ml to 15 mg/ml, 0.1 mg/ml to 10 mg/ml, 0.1 mg/ml to 7.5 mg/ml, 0.1 mg/ml to 5 mg/ml, 0.1 mg/ml to 2 mg/ml, 0.2 mg/ml to 1 mg/ml, or 0.3 mg/ml to 0.8 mg/ml and is sterilized in an aqueous, liquid form.

12. The method according to one or more of items 1 to 11, wherein the composition has one or more of the following characteristics:
   a) the composition comprises glutathione;
   b) the composition comprises glutathione in reduced form;
   c) the composition comprises glutathione in a concentration of 0.03 mg/ml to 10 mg/ml, 0.04 mg/ml to 7.5 mg/ml, 0.075 mg/ml to 5 mg/ml, 0.15 mg/ml to 4 mg/ml, 0.3 mg/ml to 3 mg, 0.4 mg/ml to 2 mg/ml, or 0.4 mg/ml to 1.3 mg/ml, wherein the glutathione is preferably in reduced form;
   d) the composition comprises glutathione and is sterilized in a liquid, preferably aqueous, form, wherein the glutathione is preferably in reduced form; and/or
   e) the composition comprises glutathione in a concentration of 0.03 mg/ml to 10 mg/ml, 0.04 mg/ml to 7.5 mg/ml, 0.075 mg/ml to 5 mg/ml, 0.15 mg/ml to 4 mg/ml, 0.3 mg/ml to 3 mg, 0.4 mg/ml to 2 mg/ml, or 0.4 mg/ml to 1.3 mg/ml and is sterilized in an aqueous, liquid form, wherein the glutathione is preferably in reduced form.

13. The method according to one or more of items 1 to 12, wherein the composition has one or more of the following characteristics:
   a) the composition comprises at least one water-soluble vitamin or a derivative thereof, wherein preferably the water-soluble vitamin is selected from ascorbic acid or a derivative thereof, vitamin B1, vitamin B2, vitamin B3, vitamin B6, folate or folic acid, vitamin B12, biotin and pantothenic acid, more preferably wherein the composition comprises ascorbic acid;
   b) the composition comprises at least one water-soluble vitamin or a derivative thereof, preferably selected from ascorbic acid, vitamin B1, vitamin B2, vitamin B3, vitamin B6, folate or folic acid, vitamin B12, biotin and pantothenic acid, more preferably ascorbic acid or a derivative thereof, in a concentration of less than 20 mg/ml, such as 0.1 mg/ml to 15 mg/ml, 1 mg/ml to 13 mg/ml, 1.5 mg/ml to 12 mg/ml, or 2 mg/ml to 11 mg/ml;
   c) the composition comprises at least one water-soluble vitamin or a derivative thereof and is sterilized in a liquid, preferably aqueous, form;
   d) the composition comprises ascorbic acid and is sterilized in a liquid, preferably aqueous, form;
   e) the composition comprises at least one water-soluble vitamin or a derivative thereof in a concentration of less than 20 mg/ml, such as 0.1 mg/ml to 15 mg/ml, 1 mg/ml to 13 mg/ml, 1.5 mg/ml to 12 mg/ml, or 2 mg/ml to 11 mg/ml and is sterilized in a liquid, preferably aqueous, form;
   f) the composition comprises ascorbic acid or a derivative thereof in a concentration of less than 20 mg/ml, wherein the concentration can be selected from 0.1 mg/ml to 15 mg/ml, 1 mg/ml to 13 mg/ml, 1.5 mg/ml to 12 mg/ml, or 2 mg/ml to 11 mg/ml and wherein the composition is sterilized by irradiation in a liquid, preferably aqueous form;
   g) the composition comprises a B vitamin, preferably Vitamin B6, in a concentration of 0.1 mg/ml to 15 mg/ml, 0.1 mg/ml to 14 mg/ml, 0.1 mg/ml to 11 mg/ml, 0.2 mg/ml to 7.5 mg/ml, or 0.2 mg/ml to 2 mg/ml; and/or
   h) the composition comprises a B vitamin, preferably Vitamin B6, in a concentration of 0.1 mg/ml to 15 mg/ml, 0.1 mg/ml to 14 mg/ml, 0.1 mg/ml to 11 mg/ml, 0.2 mg/ml to 7.5 mg/ml, or 0.2 mg/ml to 2 mg/ml, and wherein the composition is sterilized by irradiation in a liquid, preferably aqueous form.

14. The method according to one or more of items 1 to 13, wherein the composition has one or more of the following characteristics:
   a) the composition comprises a water-soluble derivative of a fat-soluble vitamin, wherein optionally the fat-soluble vitamin is selected from vitamin E, vitamin D, vitamin A and vitamin K;
   b) the composition comprises a water-soluble vitamin E derivative, wherein preferably the water-soluble vitamin E derivative is trolox;
   c) the composition comprises trolox;
   d) the composition comprises a water-soluble derivative of a fat-soluble vitamin, preferably a water-soluble vitamin E derivative, more preferably trolox, in a concentration of 0.5 mg/ml to 5 mg/ml, 0.75 mg/ml to 3 mg/ml, 0.9 mg/ml to 2 mg/ml, or 1 mg/ml to 1.4 mg/ml;
   e) the composition comprises a water-soluble derivative of a fat-soluble vitamin and is sterilized by irradiation in a liquid, preferably aqueous, form;
   f) the composition comprises a water-soluble vitamin E derivative, preferably trolox, and is sterilized in a liquid, preferably aqueous, form;
   g) the composition comprises a water-soluble derivative of a fat-soluble vitamin in a concentration of 0.5 mg/ml to 5 mg/ml, 0.75 mg/ml to 3 mg/ml, 0.9 mg/ml to 2 mg/ml, or 1 mg/ml to 1.4 mg/ml and is sterilized in a liquid, preferably aqueous, form; and/or
   h) the composition comprises a water-soluble vitamin E derivative, optionally trolox, in a concentration of 0.5 mg/ml to 5 mg/ml, 0.75 mg/ml to 3 mg/ml, 0.9 mg/ml to 2 mg/ml, or 1 mg/ml to 1.4 mg/ml and is sterilized in a liquid, preferably aqueous, form.

15. The method according to one or more of items 1 to 14, wherein the caspase inhibitor has one or more of the following characteristics:
   a) the caspase inhibitor is a pancaspase inhibitor;
   b) the caspase inhibitor comprises a modified caspase-specific peptide;
   c) the caspase inhibitor comprises a modified caspase-specific peptide that is modified, preferably at the carboxyl terminus, with an O-Phenoxy (OPh) group;
   d) the caspase inhibitor comprises a modified caspase-specific peptide that is modified, preferably at the N-terminus, with a glutamine (Q) group;
   e) the caspase inhibitor is selected from the group consisting of Q-VD-OPh, Boc-D-(OMe)-FMK and Z-Val-Ala-Asp(OMe)-FMK;
   f) the caspase inhibitor is selected from the group consisting of Q-VD-OPh and Z-Val-Ala-Asp(OMe)-FMK; and/or
   g) the caspase inhibitor is Q-VD-OPh.

16. The method according to one or more of items 1 to 15, wherein the composition further comprises one or more of:
   a) an anticoagulant and/or a chelating agent, preferably EDTA;
   b) a poly(oxyethylene) polymer as stabilizing agent; and/or
   c) at least one primary, secondary or tertiary amide.

17. The method according to one or more of items 1 to 16, wherein the composition further comprises at least one poly(oxyethylene) polymer, optionally wherein the composition has one or more of the following characteristics:
   a) the poly(oxyethylene) polymer is a polyethylene glycol, preferably unsubstituted polyethylene glycol;
   b) the composition comprises a poly(oxyethylene) polymer which is a high molecular weight poly(oxyethylene) polymer having a molecular weight of at least 1500;
   c) the composition comprises at least one poly(oxyethylene) polymer having a molecular weight below 1500, preferably a low molecular weight poly(oxyethylene) polymer having a molecular weight of 1000 or less, more preferably the molecular weight lies in a range selected from 100 to 800, 150 to 700, 200 to 600 and 200 to 500;
   d) the composition comprises a poly(oxyethylene) polymer which is a high molecular weight poly(oxyethylene) polymer having a molecular weight of at least 1500 and at least one further poly(oxyethylene) polymer that is at least 100, preferably at least 200, at least 300 or at least 400 below the molecular weight of the a high molecular weight poly(oxyethylene) polymer, wherein said further poly(oxyethylene) polymer preferably is a low molecular weight poly(oxyethylene) polymer having a molecular weight of 1000 or less; and/or
   e) the composition comprises a poly(oxyethylene) polymer which is a high molecular weight poly(oxyethylene) polymer and a poly(oxyethylene) polymer which is a low molecular weight poly(oxyethylene) polymer, wherein said high molecular weight poly(oxyethylene) polymer has a molecular weight that lies in a range selected from 1500 to 50000, 1500 to 40000, 2000 to 30000, 2500 to 25000, 3000 to 20000, 3500 to 15000 and 4000 to 12500 and/or wherein said low molecular weight poly(oxyethylene) polymer has a molecular weight of 1000 or less and wherein preferably, the molecular weight lies in a range selected from 100 to 1000, 150 to 800, 150 to 700, 200 to 600 and 200 to 500.

18. The method according to one or more of items 1 to 17, wherein the composition further comprises at least one primary, secondary or tertiary amide, optionally wherein the composition has one or more of the following characteristics:
   a) the composition comprises at least one primary, secondary or tertiary amide according to formula 1

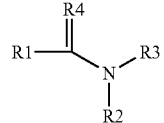

formula 1 wherein R1 is a hydrogen residue or an alkyl residue, preferably a C1-C5 alkyl residue, a C1-C4 alkyl residue or a C1-C3 alkyl residue, more preferred a C1-C2 alkyl residue, R2 and R3 are identical or different and are selected from a hydrogen residue and a hydrocarbon residue, preferably an alkyl residue, with a length of the carbon chain of 1-20 atoms arranged in a linear or branched manner, and R4 is an oxygen, sulphur or selenium residue, preferably R4 is oxygen; and/or
   b) the composition comprises a N,N-dialkylpropanamide, preferably N,N-dimethlypropanamide, and/or butanamide.

19. The method according to one or more of items 1 to 18, wherein the composition comprises at least one compound according to formula 1

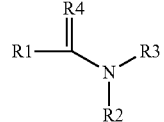

formula 1 wherein R1 is a hydrogen residue or an alkyl residue, preferably a C1-C5 alkyl residue, a C1-C4 alkyl residue or a C1-C3 alkyl residue, more preferred a C1-C2 alkyl residue, R2 and R3 are identical or different and are selected from a hydrogen residue and a hydrocarbon residue, preferably an alkyl residue, with a length of the carbon chain of 1-20 atoms arranged in a linear or branched manner, and R4 is an oxygen, sulphur or selenium residue, preferably R4 is oxygen.

20. The method according to item 19, wherein the at least one compound according to formula 1 is a primary, secondary or tertiary carboxylic acid amide.

21. The method according to one or more of items 1 to 20, wherein the sterilized composition has one or more of the following characteristics:
   i) it is suitable for stabilizing intracellular nucleic acids comprised in a cell-containing sample wherein preferably, intracellular RNA and/or intracellular DNA is stabilized;
   ii) it reduces the degradation of nucleic acids present in a cell-containing sample due to the stabilization;
   iii) it is suitable for stabilizing the transcriptome and/or transcript levels in cells contained in the sample, wherein preferably, it is suitable for stabilizing the transcript level of one or more marker genes selected from c-fos, IL-1beta, IL-8 and p53 is stabilized for at least 12 h, at least 24 h, preferably at least 48 h upon stabilization.

22. The method according to one or more of items 1 to 21, wherein the sterilized composition does not induce lysis of nucleated cells or cells in general.

23. The method according to one or more of items 1 to 22, wherein the sterilized composition does not comprise a cross-linking agent that induces nucleic acid-nucleic acid, protein-nucleic acid and/or protein-protein crosslinks and does not involve the use of a formaldehyde releaser.

24. The method according to one or more of items 1 to 23, wherein the sterilized composition has the following stabilization characteristics:
  a) the stabilization allows the isolation of cells from the stabilized cell-containing sample;
  b) the cell-containing sample is a blood sample and wherein cells contained in the blood sample are stabilized;
  c) the cell-containing sample is a blood sample and wherein white blood cells are stabilized;
  d) the morphology of cells is preserved;
  e) the morphology of nucleated cells is preserved;
  f) the sample is a blood sample and contained lymphocytes and/or monocytes are stabilized;
  g) cell surface epitopes are preserved; and/or
  h) cell surface proteins are preserved.

25. A sterilizable composition, wherein the composition in sterilized form is suitable for stabilizing an extracellular nucleic acid population of a biological sample, wherein the composition is a composition as provided in step a) of one or more of items 1 to 18 or one or more of items 19 to 24, and wherein preferably the composition is sterilized.

26. A method for stabilizing an extracellular nucleic acid population comprised in a cell-containing biological sample comprising:
  a) obtaining a sterilized composition suitable for stabilizing an extracellular nucleic acid population of a biological sample according to the method defined in one or more of items 1 to 18 or one or more of items 19 to 24, or obtaining a composition according to item 25 in sterilized form; and
  b) contacting the cell-containing biological sample with the sterilized composition for stabilization.

27. A method for isolating extracellular nucleic acids from a stabilized cell-containing biological sample comprising:
  a) stabilizing the cell-containing biological sample according to the method of item 26; and
  b) isolating extracellular nucleic acids.

28. A method for processing and/or analyzing extracellular nucleic acids comprising:
  a) isolating extracellular nucleic acids from a stabilized cell-containing biological sample according to the method of item 27; and
  b) processing and/or analyzing the isolated extracellular nucleic acids.

29. Use of at least one compound selected from the group consisting of a thioalcohol and a vitamin or a derivative thereof for protecting a composition suitable for stabilizing an extracellular nucleic acid population of a biological sample or components thereof during sterilization by irradiation.

30. The use of item 29, wherein the at least one compound is selected from the group consisting of a thioalcohol, a water-soluble vitamin or a derivative thereof, and a water-soluble derivative of a fat-soluble vitamin; or
  wherein the at least one compound selected from a thioalcohol that is N-acetyl-cysteine or glutathione, a water-soluble vitamin or a derivative thereof, and a water-soluble derivate of a fat-soluble vitamin; or
  wherein the at least one compound is selected from a thioalcohol that is N-acetyl-cysteine or glutathione, a water-soluble vitamin, and a water-soluble vitamin E derivate; or
  wherein the at least one compound is selected from a thioalcohol that is N-acetyl-cysteine or glutathione, ascorbic acid or a derivative thereof, and a water-soluble vitamin E derivate.

31. A method for producing a sterilizable composition, wherein the composition in sterilized form is suitable for stabilizing an extracellular nucleic acid population of a biological sample, the method comprising:
  a) preparing a composition comprising:
    i. at least one caspase inhibitor, and
    ii. at least one compound selected from a thioalcohol and a vitamin or a derivative thereof, and optionally
  b) sterilizing the composition.

32. The method of item 31, wherein the composition prepared in step a) of item 31 is a composition as prepared in step a) of one or more of items 1-18 or one or more of items 19-24.

33. A sample collection device such as a container, preferably a sample collection tube, comprising the sterilizable composition according to item 25.

34. A kit comprising the sterilizable composition according to item 25 or a sample collection device according to item 33.

35. A method for isolating nucleic acids from a stabilized cell-containing biological sample comprising
  a) stabilizing a cell-containing biological sample, wherein stabilization comprises
    i) obtaining a sterilized composition according to a method defined in one or more of items 1 to 24; or
    ii) obtaining a composition according to item 25, wherein the composition is sterilized; or
    iii) obtaining a sample collection device according to item 33, wherein the composition comprised therein is sterilized;
    and contacting the cell-containing biological sample with the sterilized composition; and
  b) isolating nucleic acids from the stabilized sample.

36. The method according to item 35, wherein step b) comprises isolating intracellular nucleic acids, preferably intracellular RNA and/or intracellular DNA.

37. The method according to item 35 or 36, comprising removing cells from the stabilized sample and isolating nucleic acids from the removed cells.

38. A method for isolating cells from a stabilized cell-containing biological sample comprising
  a) stabilizing a cell-containing biological sample, wherein stabilization comprises
    i) obtaining a sterilized composition according to a method defined in one or more of items 1 to 24; or
    ii) obtaining a composition according to item 25, wherein the composition is sterilized; or
    iii) obtaining a sample collection device according to item 33, wherein the composition comprised therein is sterilized;
    and contacting the cell-containing biological sample with the sterilized composition; and
  b) isolating cells from the stabilized sample.

39. A sterilized composition obtainable and/or obtained by the method according to one or more of items 1-24.

40. A sterilized sample collection device such as a container, preferably a sample collection tube, comprising a sterilized composition according to item 39, wherein the sterilized sample collection device is obtainable and/or obtained by the method according to one or more of items 1-24.

This application claims priority from EP 15 195 656.2, filed on Nov. 20, 2015, and from EP 16 163 863.0, filed on Apr. 5, 2016. The contents of EP 15 195 656.2 and of EP 16 163 863.0 are incorporated herein by reference in their entirety.

EXAMPLES

The examples are for illustrative purpose only and are not to be construed as limiting this invention in any manner.
Abbreviations Used:
ccfDNA: circulating, cell-free DNA
PEG: Polyethylene glycol
EDTA: Ethylenediaminetetraacetic acid
DMPA: Dimethylpropionamide
HPLC: high-performance liquid chromatography
BCT: Blood collection tube
kGy: kilo Gray
DMSO: Dimethyl sulfoxide

I. EXPERIMENTAL PROCEDURES

The effect of sterilization, in particular by gamma irradiation, on compositions for the stabilization of extracellular nucleic acid populations (hereinafter also designated as "stabilization reagent" or "stabilization composition") was determined by two different means. The chemical degradation profile of the stabilization compositions was evaluated by high-performance liquid chromatography (HPLC). A functional assay was performed to determine the impact of the sterilization on the stabilizing activity of the compositions on extracellular nucleic acids. In this assay, ccfDNA was analysed as a preferred embodiment of an extracellular nucleic acid population.

The inventors were able to identify compounds that surprisingly are able to mitigate or even abolish the chemical degradation occurring during sterilization in the stabilization compositions. Importantly, these compounds at the same time allowing for optimal function of the stabilization compositions once sterilized.

1. HPLC Testing of Stabilization Reagents:

Caspase inhibitor (Q-VD-OPh) was dissolved and diluted in DMSO for generation of a standard curve. Concentrations of 7.5, 15, 30 and 60 µg/ml were used to generate the standard curve.

Stabilization reagents containing a mixture of caspase inhibitor, EDTA, DMPA and PEG were tested before and after gamma irradiation. Unique peaks for caspase inhibitor were identified and compared to the standard curve for total quantification of caspase inhibitor. The concentration of caspase inhibitor was determined before and after irradiation, and these concentrations were compared for relative quantification.

2. Production of PAXgene Blood ccfDNA Alpha Tubes:

For the production of PAXgene Blood ccfDNA Alpha blood collection tubes (Alpha BCT), BD standard tubes for 10 ml blood draw were filled with 1.3-1.7 ml ccfDNA stabilization reagent. The exemplary stabilization reagents tested comprised a mixture of caspase inhibitor (Q-VD-OPh), K2EDTA, DMPA, PEG300 and PEG10000, according to PCT/EP2015/055699. A vacuum was applied to the tubes to allow for a 10.25 ml blood draw. Tubes were sterilized by gamma irradiation using Cobalt-60 as energetic gamma ray source in a range of 5 to 35 kGy.

3. Stabilization of Whole Blood:

Blood was drawn into Alpha BCT for stabilization of the ccfDNA level. 10 ml spray dried EDTA tubes (BD) with 1.8 mg K2EDTA per ml of whole blood served as non-stabilized negative control. Blood and reagents were mixed by inverting the tube ten times. Stabilized and non-stabilized blood samples were stored at room temperature standing in an upright position.

4. Preparation of Plasma:

Whole blood samples were centrifuged at ambient temperature for 15 min at 1.900×g. The clear plasma fraction was transferred into a fresh centrifuge tube. In a second round, plasma samples were centrifuged for 10 min at 16.000×g in case of non-stabilized EDTA-blood or for 10 min at 1.900×g in case of stabilized Alpha BCT blood. The supernatant was transferred into a new tube and used either directly for the purification of ccfDNA or stored at −20° C. until use.

5. Manual Purification of ccfDNA with the QIAamp Circulating Nucleic Acid Kit:

DNA from plasma was isolated with the QIAamp circulating nucleic acid kit (QIAGEN GmbH), using the protocol for purification of circulating nucleic acids from 1 ml, 2 ml, or 3 ml serum or plasma. If not stated otherwise, 2 ml of plasma was mixed with proteinase K and lysis buffer ACL, incubated for 30 min at 60° C., mixed with buffer ACB, bound on QIAamp Mini columns with the use of a QIAvac 24 Plus vacuum manifold, washed and eluted with 60 µl elution buffer AVE, according to the manufactures recommendations.

6. Automated Purification of ccfDNA on the QIAsymphony:

ccfDNA from 2 ml plasma was isolated with a preliminary version of the QIAsymphony Circulating DNA protocol and kit (QIAGEN). If not stated otherwise, the QIAsymphony robot mixed 2 ml of plasma with proteinase K, binding buffer and magnetic beads. Beads with bound DNA were washed three times and DNA was eluted using 60 µl elution buffer.

7. Quantitative, Real Time PCR Assay and Calculation of ccfDNA Copies:

To measure the amount of ccfDNA, a real time PCR assay on Abi Prism HT7900 (Life Technologies) was performed with 3 µl of eluate. In a 20 µl assay volume using QuantiTect Multiplex PCR Kit reagents (QIAGEN GmbH), two fragments of the human 18S rDNA gene were amplified in a multiplex PCR. Total quantification was achieved by comparison with a standard curve generated with human genomic DNA diluted from 3000 to 0.3 genome equivalents (1 genome equivalent equates to around 6.6 µg of human genomic DNA).

TABLE 1

DNA target sequences detected by real time PCR

| Target description | position | Sequence position | 5'-3' | dye |
|---|---|---|---|---|
| h 18S rDNA 66bp amplicon | p12 - region of chromosome 13, 14, 15, 21, 22 | forward reverse probe | GCCGCTAGAGGTGAAATTCTTG CATTCTTGGCAAATGCTTTCG ACCGGCGCAAGACGGACCAGA | 5' Bodipy-BHQ 3' |
| h18S rDNA 500bp amplicon | p12 - region of chromosome 13, 14, 15, 21, 22 | forward reverse probe | GTCGCTCGCTCCTCTCCTACTT GGCTGCTGGCACCAGACTT CTAATACATGCCGACGGGCGCTGAC | 5' FAM-BHQ 3' |

Quantification of the 66 bp fragment was used to reflect the total amount of 18S rDNA copies in the plasma. Quantification of the 500 bp was used to determine the amount of 18S rDNA copies which derived from apoptotic or mechanically lysed leukocytes from whole blood. Cell-free DNA has a typical length of 140-170 bp (Forshew et al. (2012) Cancer Genomics 4(136) 136ra68). Therefore 500 bp fragments are derived from apoptotic, lysed or otherwise destructed blood cells. The increase of copy numbers from the 500 bp fragment between day 0 and 3 or 6 days storage, was used as a measurement of stability efficiency.

II. EXAMPLES

1. Example 1: Effect of Gamma Irradiation on ccfDNA Stabilization

PAXgene Blood ccfDNA Alpha tubes were produced and sterilized by gamma irradiation with different energy levels. Samples of 10 ml whole blood from eight donors were collected in 10 ml spray dry K2EDTA tubes (non-stabilized controls) and in PAXgene Blood ccfDNA Alpha tubes. Plasma was generated from 5 ml of stabilized or non-stabilized blood samples directly after blood draw. Residual blood was stored for additional 6 days at room temperature before plasma generation. ccfDNA was purified manually from 2 ml plasma, copy numbers of 18S rDNA gene were determined in triplicates by real time PCR.

The stabilization reagent mixture according to PCT/EP2015/055699 (for one Alpha tube) was: 11.45 µl caspase inhibitor (Q-VD-OPh; 1 mg dissolved in 388 µl DMSO); the reagent further comprised PEG10.000, PEG300, EDTA and DMPA, water ad 1.7 ml. After addition of whole blood, the Alpha tubes comprised Q-VD-OPh at a final concentration of approx. 5 µM.

The non-stabilized controls comprised K2EDTA at a final concentration of 1.8 mg/ml in whole blood.

Figure 1:
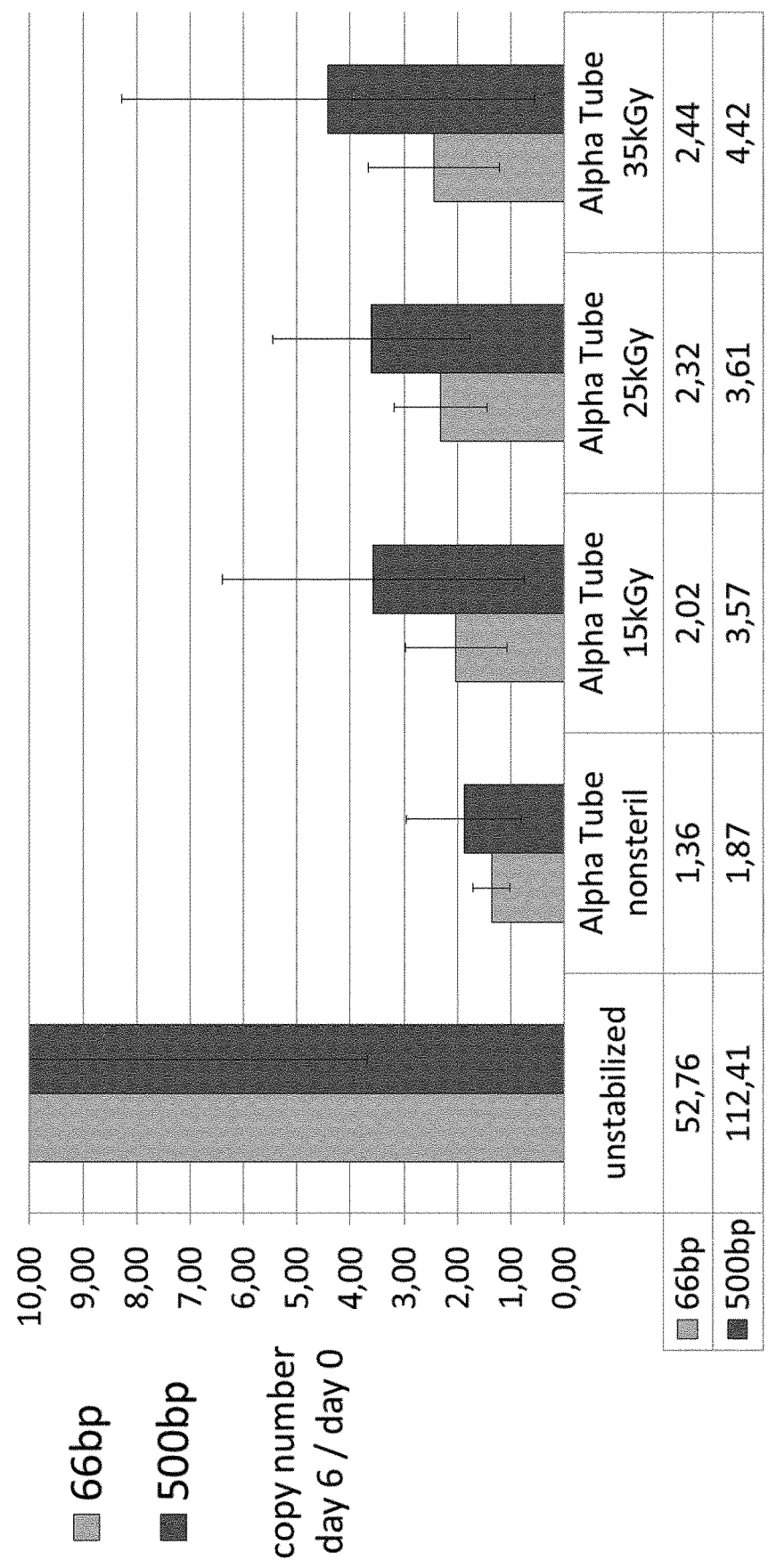
FIG. 1: Effect of gamma irradiation on the stabilization properties of a caspase inhibitor containing composition. The effect is analysed based on the ccfDNA level in plasma. The figure shows the average change and standard deviation of copy numbers (x fold change) of 66 bp and 500 bp fragments of the 18S rDNA gene in non-stabilized EDTA blood (left) and in stabilized blood samples drawn into tubes comprising a stabilization composition comprising a caspase inhibitor (non-sterile or sterilized with different doses of gamma irradiation) after storage.

The effect of gamma irradiation on the ccfDNA level in plasma is shown in FIG. 1. The figure shows the average change and standard deviation of copy numbers (x fold change) of 66 bp and 500 bp fragments of the 18S rDNA gene in non-stabilized EDTA blood (left) and in stabilized blood samples drawn into Alpha tubes (nonsterile or sterilized with different doses of gamma irradiation). Samples were from 8 donors and stored for 6 days at room temperature.

As can be seen, the ratio of copy numbers (day 6/day 0) is lower in stabilized samples (Alpha tubes) compared to the non-stabilized control (EDTA blood, left), demonstrating that stabilization of extracellular nucleic acids had occurred in the stabilized samples. However, as can be seen when comparing stabilized samples, the efficiency of ccfDNA stabilization decreases with increasing doses of gamma irradiation used to sterilize the stabilizing reagent prior to adding the blood sample to be stabilized. Decreasing stabilization efficiency associated with increasing doses of gamma irradiation is visualized by the increasing ratio of copy numbers (day 6/day 0) obtained for increasing radiation doses.

Conclusion:

Gamma irradiation used for sterilization has a dose-dependent effect on the subsequent ccfDNA stabilization by the stabilization reagent when applied to a stabilization reagent comprising a caspase inhibitor. The higher the irradiation dose applied for sterilization, the less is the stabilization in subsequent applications.

2. Example 2: Degradation of Caspase Inhibitor by Gamma Irradiation

Figure 2:
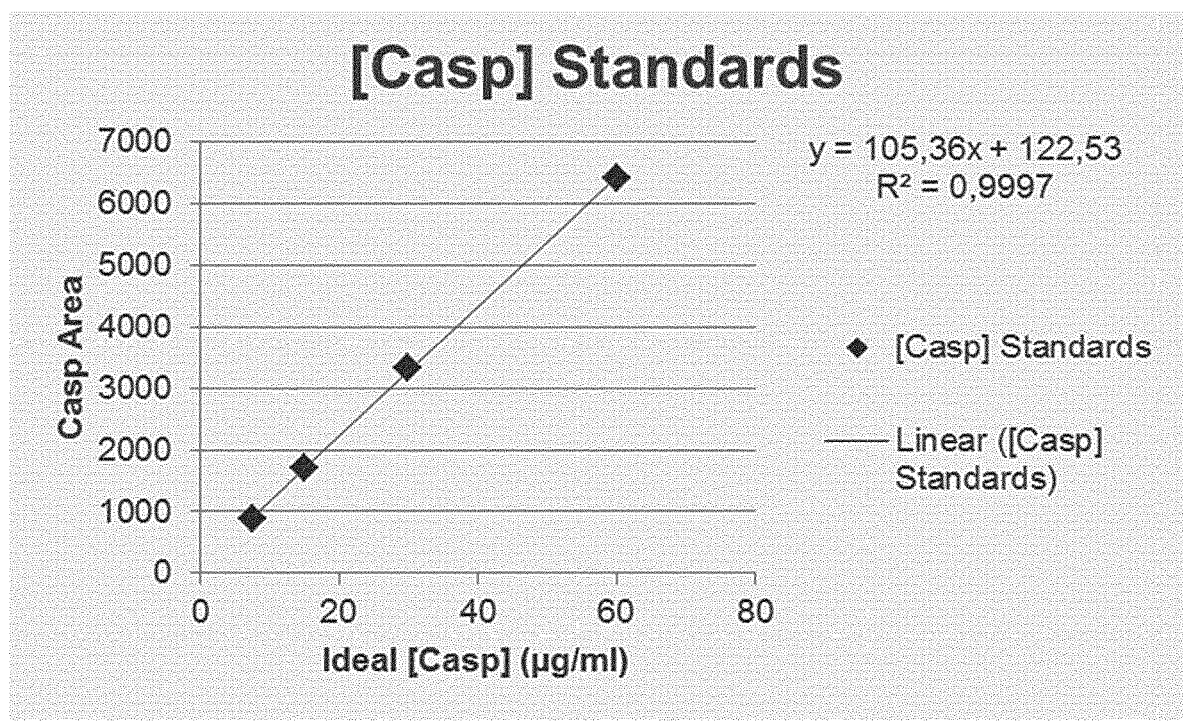
FIG. 2: HPLC standard curve prepared with different concentrations of pure caspase inhibitor dissolved in DMSO.

PAXgene Blood ccfDNA Alpha tubes were produced and sterilized with different energy levels by gamma irradiation. For quantification by HPLC, a standard curve was generated for caspase inhibitor (Q-VD-OPh) dissolved in DMSO only. The standard curve generated is shown in FIG. 2. Table 2 (below) indicates the concentrations of caspase inhibitor as well as peak area and retention times for the different concentrations of caspase inhibitor.

TABLE 2

Results of HPLC analysis; preparation of standard curve.

| Standard | Caspase inhibitor Area | Retention time (min) | [Caspase inhibitor] (µg/ml) |
|---|---|---|---|
| Level 1 (7.5 µg/ml) | 877.8911 | 26.2441 | 7.6628 |
| Level 2 (15 µg/ml) | 1708.6633 | 26.2605 | 15.4100 |
| Level 3 (30 µg/ml) | 3335.8472 | 26.3373 | 30.6098 |
| Level 4 (60 µg/ml) | 6420.9580 | 26.3873 | 59.5803 |

As a next step, stabilization reagents from Alpha tubes were measured before and after irradiation, in order to determine the concentrations of caspase inhibitor. Unique peaks for caspase inhibitor were compared to the standard curve for total quantification. The percentage of non-degraded caspase inhibitor after sterilization was calculated by comparison to non-sterilized Alpha tubes.

The results are shown in Table 3 (below). The table shows the peak area and retention times for the different samples tested determined by HPLC, as well as the concentration of inhibitor calculated based on the standard curve.

TABLE 3

Results of HPLC analysis; determination of % caspase inhibitor left after irradiation.

|  | Caspase inhibitor Area | Retention time (min) | [Caspase inhibitor] (µg/ml) |
|---|---|---|---|
| [Caspase inhibitor] ~15 µg/ml | 1708.6633 | 26.2605 | 15.4100 |
| A13-2 Bulk Solution (before filling into Alpha Tubes) | 1682.2621 | 26.3736 | 15.1219 |
| Alpha Tube batch 13-1 (non-irradiated) | 1742.5447 | 26.4114 | 15.6875 |
| Alpha Tube batch 13-3 Tube (irradiated 15 kGy) | 294.2026 | 26.3655 | 2.0992 |
| % left after irradiation |  |  | 13.38 |

Peaks caused by other components in the stabilization reagent according to PCT/EP2015/055699 occur earlier in the process than that for the caspase inhibitor. While the caspase inhibitor occurs at 26 min, the further components are closer to the 16-22 min range. Thus comparing the HPLC results of the stabilization reagent with the HPLC results for caspase inhibitor only (used for the generation of the standard curve) demonstrates that there is no interference caused by the other constituents (EDTA, PEG and DMPA) with the detection of caspase inhibitor in the stabilization reagent.

Conclusion:

In conclusion, HPLC is a useful technique for quantifying the degree of caspase inhibitor degradation caused by gamma irradiation. Degradation of caspase inhibitor occurs during irradiation and the decreased stabilization of ccDNA level after sterilization (see FIG. 1) is associated with a decreased concentration of intact, non-degraded caspase inhibitor.

To further examine the impact of different doses of gamma irradiation on caspase inhibitor, caspase inhibitor was quantified in PAXgene Blood ccfDNA Alpha tubes from different batches of stabilization reagent, sterilized with different doses of gamma irradiation. The Alpha tubes comprised a stabilization reagent as detailed above in Table 3.

The results are shown in Table 4 (below). As can be seen, gamma irradiation has a dose-dependent effect on caspase inhibitor degradation.

Conclusions:

Gamma irradiation has a dose-dependent effect on caspase inhibitor degradation in a stabilization reagent. The higher the irradiation dose, the more degradation occurs. HPLC can be used for quantification of the degradation effect caused by gamma irradiation on caspase inhibitor.

3. Example 3: Effect of Addition of Scavengers on ccfDNA Stabilization

In order to prevent degradation of caspase inhibitor during sterilization by gamma irradiation, components where tested for their ability to protect the caspase inhibitor from degradation during irradiation. To exclude that the additional components themselves have a negative impact on the level of extracellular nucleic acid, these compounds were added to stabilizing reagents comprising a caspase inhibitor (Q-VD-OPh) and further comprising PEG, EDTA and DMPA, and tested in functional assays.

Samples of 10 ml whole blood from eight donors were collected in 10 ml spray dry K2EDTA tubes. Directly after blood draw, non-stabilized blood samples were stabilized by addition of 1.7 ml of a ccfDNA stabilization reagent according to PCT/EP2015/055699 with or without addition of the different compounds tested for their impact on extracellular nucleic acid stabilization.

The stabilization reagent comprised (for 10 ml K2EDTA whole blood): 11.45 µl caspase inhibitor (Q-VD-OPh; 1 mg dissolved in 388 µl DMSO), the reagent further comprised PEG10.000, PEG300, EDTA and DMPA, water ad 1.7 ml. Scavengers were added as further detailed below.

After addition of whole blood, the Alpha tubes comprised Q-VD-OPh at a final concentration of 5 µM.

Plasma was generated from 5 ml of stabilized blood samples directly after the blood draw (day 0). Residual blood was stored for additional 6 days at room temperature before plasma was generated (day 6). ccfDNA was purified from 2 ml plasma, and copy numbers of the 18S rDNA gene were determined in triplicates by real time PCR.

a) Addition of N-Acetyl-Cysteine, Ascorbic Acid, Gallic Acid and Tannic Acid

Figure 3:
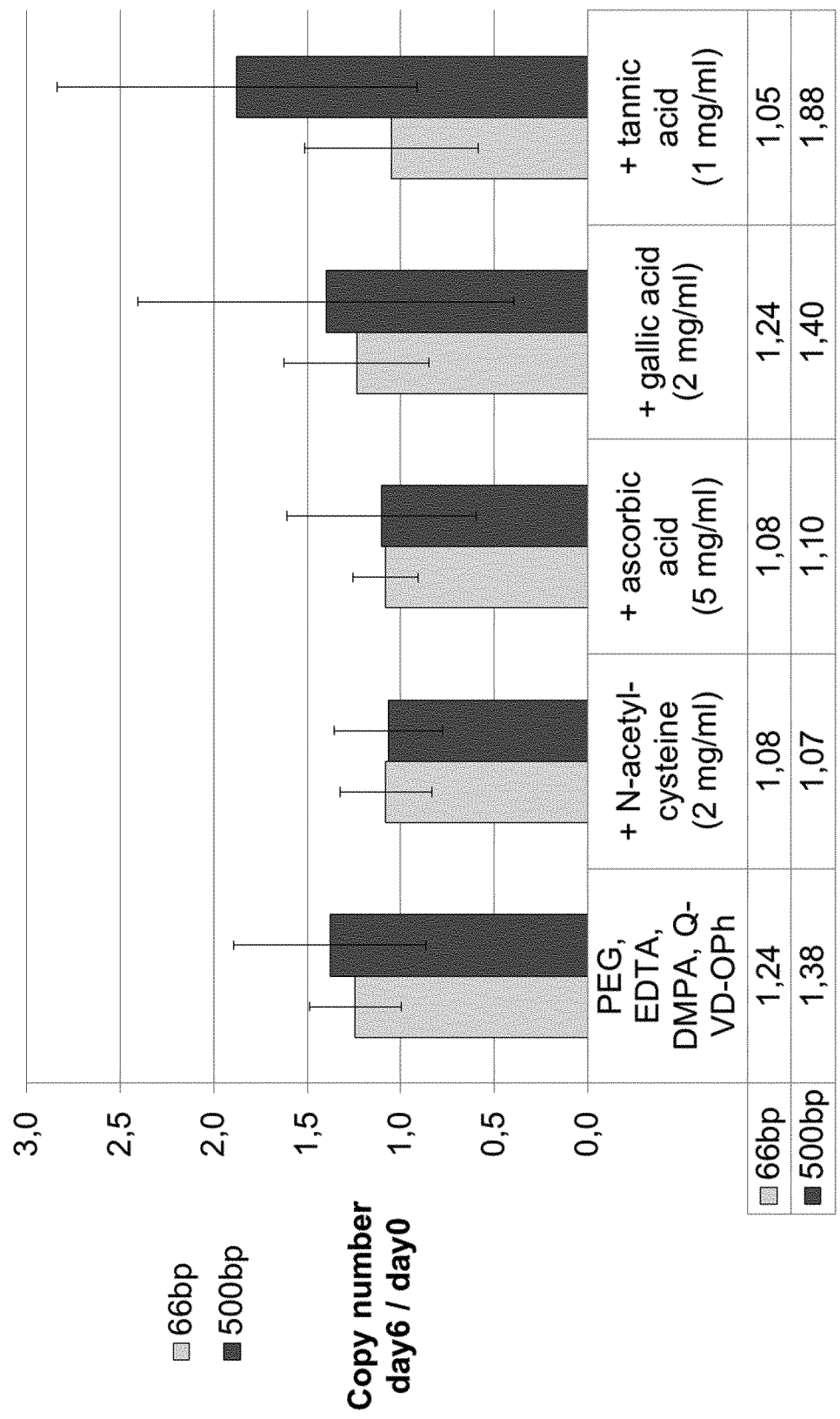
FIG. 3: Addition of N-acetyl-cysteine, ascorbic acid, gallic acid and tannic acid to the caspase inhibitor containing stabilization composition. Average change of copy numbers (x fold change) of 66 bp and 500 bp fragments of the 18S rDNA gene in stabilized blood after storage.

N-acetyl-cysteine, ascorbic acid, gallic acid or tannic acid were added to the stabilization reagent in concentrations as indicated in FIG. 3: N-acetyl-cysteine, 2 mg/ml; ascorbic acid, 5 mg/ml; gallic acid, 2 mg/ml; tannic acid, 1 mg/ml.

The final concentrations in whole blood were: 1.7 mM N-acetyl-cysteine or 4.0 mM ascorbic acid or 1.7 mM gallic acid or 0.09 mM tannic acid.

TABLE 4

Quantification of caspase inhibitor in PAXgene Blood ccfDNA Alpha tube from different batches of stabilization reagent, sterilized with different doses of gamma irradiation.

| PAXgene Blood ccfDNA Alpha-Tube batch | Irradiation (kGy) | Initial [C-Inh] at DOM [µg/ml] | HPLC Testing [C-Inh] (µg/ml) | % Detected | % Remaining C-Inh from Solution |
|---|---|---|---|---|---|
| A13 1 | 0 | 18 | 15.688 | 87.15% | 100.00% |
| A13 1-1 | 18.6 | 18 | 0.634 | 3.52% | 4.06% |
| A13 1-2 | 29.7 | 18 | 0.064 | 0.35% | 0.41% |
| A13 1-3 | 39.3 | 18 | 0.033 | 0.18% | 0.21% |
| A13 2 | 0 | 18 | 15.586 | 86.59% | 100.00% |
| A13 2-1 | 15.8 | 18 | 2.360 | 13.11% | 15.14% |
| A13 2-2 | 27.1 | 18 | 0.603 | 3.35% | 3.87% |
| A13 2-3 | 37.5 | 18 | 0.103 | 0.57% | 0.66% |

The results are shown in FIG. 3. The figure shows the average change of copy numbers (x fold change) of 66 bp and 500 bp fragments of the 18S rDNA gene in stabilized blood after storage for stabilization reagent only (left) and upon addition of N-acetyl-cysteine, ascorbic acid, gallic acid or tannic acid. Results are from blood from 8 donors stored for 6 days at room temperature.

Conclusions:

The addition of certain radical scavengers such as ascorbic acid and N-acetyl-cysteine to the caspase inhibitor containing stabilization reagent is possible without affecting the ccfDNA stabilization characteristics.

Figure 4:
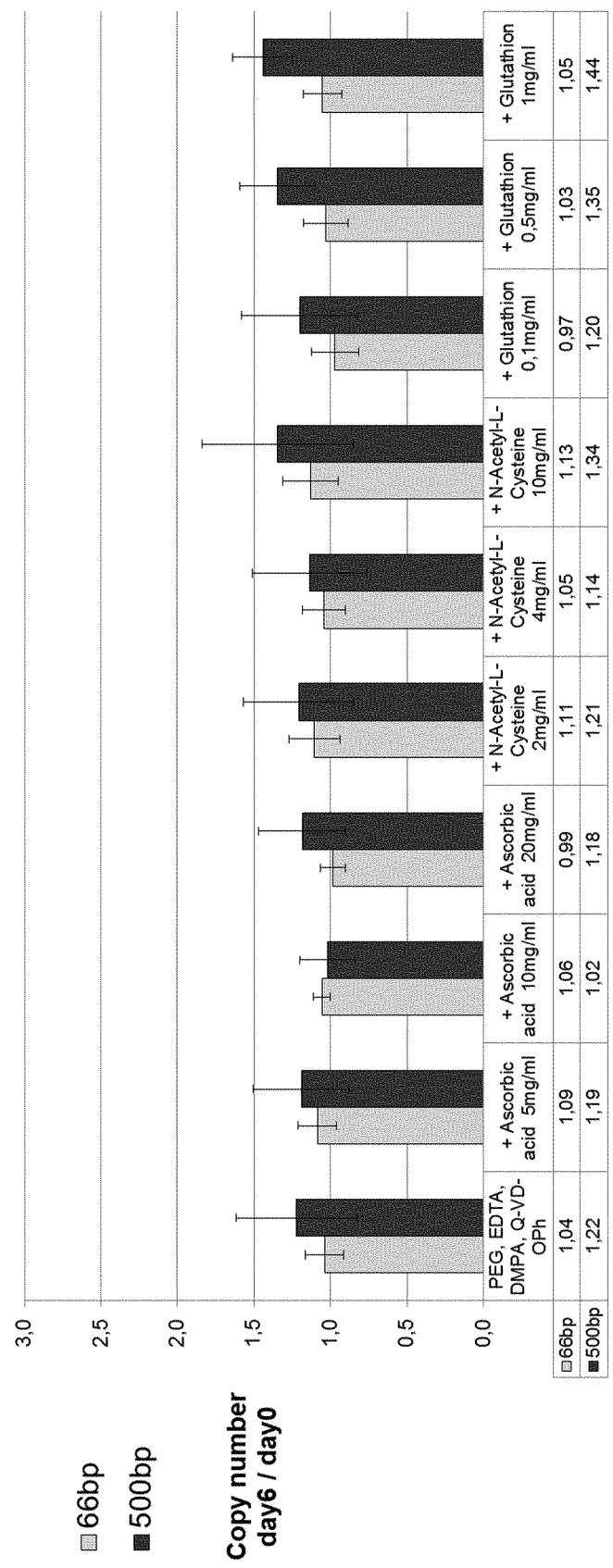
FIG. 4: Addition of ascorbic acid, N-acetyl-cysteine and glutathione (reduced) in different concentrations to the caspase inhibitor containing stabilization composition. Average change of copy numbers (x fold change) of 66 bp and 500 bp fragments of the 18S rDNA gene in stabilized blood after storage.

However, it was surprisingly found that the addition of certain radical scavengers such as tannic acid or gallic acid, reported in the prior art to be effective against gamma radiation induced free radicals, lead to an increased release of DNA in blood stabilized with the ccfDNA stabilization reagent, as can be seen in FIG. 3 by increased ratio of 500 bp copy numbers between day 6 and day 0 and the high standard deviation for both the 66 and the 500 bp fragments. These compounds are thus unsuitable for use in a composition for stabilizing an extracellular nucleic acid population.

b) Addition of Ascorbic Acid, N-Acetyl-Cysteine and Glutathione (Reduced) in Different Concentrations In a further experiment ascorbic acid, N-acetyl-cysteine or glutathione (reduced) were added to the stabilization reagent in concentrations as indicated in FIG. 4: ascorbic acid, 5 mg/ml, 10 mg/ml or 20 mg/ml; N-acetyl-cysteine, 2 mg/ml, 4 mg/ml or 10 mg/ml; glutathione (reduced), 0.1 mg/ml, 0.5 mg/ml or 1 mg/ml.

The final concentrations in whole blood were: 4.0 mM or 8.0 mM or 16.0 mM ascorbic acid; 1.7 mM or 3.5 mM or 8.7 mM N-acetyl-cysteine; or 0.05 mM or 0.23 mM or 0.47 mM glutathione (reduced).

The results are shown in FIG. 4. The figure shows the average change of copy numbers (x fold change) of 66 bp and 500 bp fragments of the 18S rDNA gene in stabilized blood after storage for stabilization reagent only (left) and upon addition of ascorbic acid, N-acetyl-cysteine or glutathione (reduced) in different concentrations. Blood was from 8 donors and had been stored for 6 days at room temperature.

Figure 5:
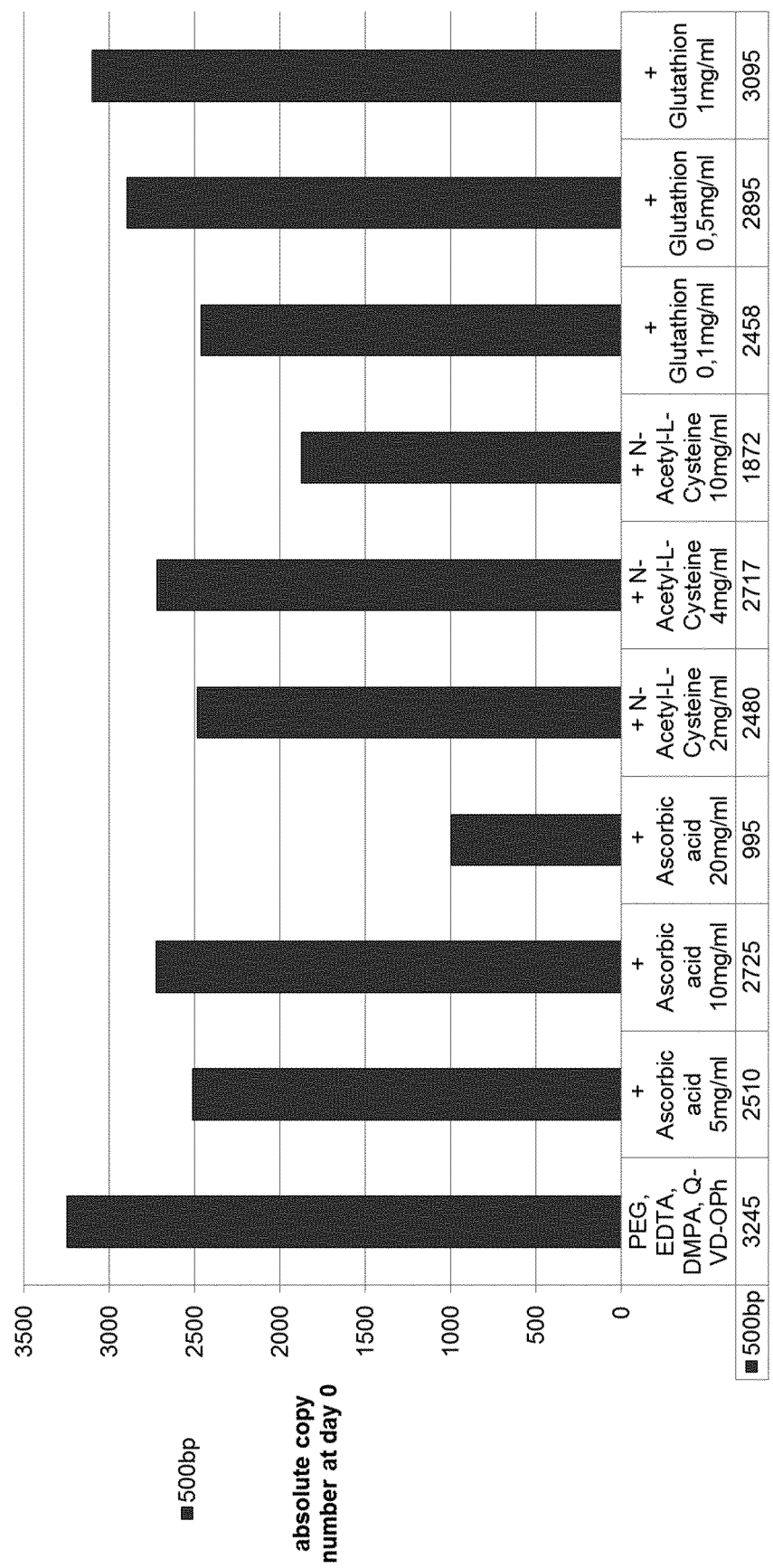
FIG. 5: Addition of ascorbic acid, N-acetyl-cysteine and glutathione in different concentrations to the caspase inhibitor containing stabilization composition. Average total copy numbers of the 500 bp fragment of the 18S rDNA gene in stabilized blood after storage.

FIG. 5 shows the average total copy numbers of the 500 bp fragment of the 18S rDNA gene in stabilized blood as determined directly after blood collection.

Conclusion:

Stabilization reagents comprising ascorbic acid, N-acetyl-cysteine or glutathione (reduced) showed good stabilization properties at the tested concentrations (FIG. 4). As can be seen from FIG. 5, the addition of ascorbic acid in a concentration of 20 mg/ml, a concentration reported in the art to be (radio-)protective against gamma radiation induced free radicals, lead to reduced ccfDNA absolute copy numbers.

c) Addition of Different Combinations of Ascorbic Acid, N-Acetyl-Cysteine and Glutathione In another experiment the influence of different combinations of ascorbic acid, N-acetyl-cysteine and glutathione on the ccfDNA stabilization characteristics of the stabilizing reagents was tested.

To that end, ascorbic acid, N-acetyl-cysteine and glutathione (reduced) were added to the stabilization reagent in combinations and concentrations as indicated in FIG. 6: ascorbic acid (2 mg/ml) and glutathione (0.2 mg/ml); N-acetyl-cysteine (1 mg/ml) and glutathione (0.2 mg/ml); ascorbic acid (2 mg/ml) and N-acetyl-cysteine (1 mg/ml); ascorbic acid (2 mg/ml), N-acetyl-cysteine (1 mg/ml) and glutathione (0.2 mg/ml).

The final concentrations in whole blood were: 1.65 mM ascorbic acid and 0.1 mM glutathione (reduced); 0.9 mM N-acetyl-cysteine and 0.1 mM glutathione (reduced); 1.65 mM ascorbic acid and 0.9 mM N-acetyl-cysteine; 1.65 mM ascorbic acid and 0.9 mM N-acetyl-cysteine and 0.1 mM glutathione (reduced).

The results are shown in FIG. 6. The figure shows the average change of copy numbers (x fold change) of 66 bp and 500 bp fragments of the 18S rDNA gene in stabilized blood from 8 donors stored for 6 days at room temperature.

As can be seen from FIG. 6, good ccfDNA stabilization characteristics could be obtained with the tested scavenger combinations.

Conclusions:

The addition of combinations of radical scavengers according to the invention such as ascorbic acid, N-acetyl-cysteine and glutathione (reduced) in suitable concentrations to a stabilization reagent comprising a caspase inhibitor is possible without affecting the ccfDNA stabilization characteristics.

4. Example 4: Effect of Addition of Scavengers on Caspase Inhibitor Concentration and ccfDNA Stabilization after Gamma Irradiation The effect of scavenger addition on caspase inhibitor degradation during sterilization by gamma irradiation was analyzed. Also, the effect of scavenger addition (prior to sterilization in order to protect the caspase inhibitor) on the ccfDNA stabilization characteristics of the (sterilized) stabilizing reagents was assessed.

Stabilization reagents were produced with or without the addition of radical scavengers and sterilized in bulk by gamma irradiation. The caspase inhibitor concentration was measured by HPLC before and after irradiation to determine the effect of scavenger addition on caspase inhibitor degradation during sterilization by gamma irradiation.

The stabilization reagents comprised (for 10 ml K2EDTA whole blood): 11.45 µl caspase inhibitor (Q-VD-OPh; 1 mg dissolved in 388 µl DMSO), the reagents further comprised PEG10.000, PEG300, EDTA and DMPA, water ad 1.7 ml. Scavengers were added as further detailed below. After addition of whole blood, the Alpha tubes comprised Q-VD-OPh at a final concentration of 5 µM.

Scavengers were added to the stabilization reagent in concentrations as indicated in the Table 5 (below).

TABLE 5

Quantification of caspase inhibitor in stabilization reagent with or without scavenger before and after gamma irradiation

| Stabilization reagent + scavenger | Type | Volume (ml) | Irradiation (kGy) | [Casp] (Pre-Irr) [µg/ml] | [Casp] (Post-Irr) [µg/ml] | % C-Inh Remaining |
|---|---|---|---|---|---|---|
| PEG, EDTA, DMPA, Q-VD-OPh | Reference | 50 | 25 | 16.505 | 0.9382 | 5.68% |
| + Gallic acid (500 µg/ml-2.9 mM) | scavenger | 50 | 25 | 16.633 | 0.5888 | 3.54% |
| + Ascorbic acid (5 mg/ml-27.5 mM) | scavenger | 50 | 25 | 16.522 | 12.5986 | 76.25% |
| + N-acetyl-L-cysteine (2 mg/ml-12 mM) | scavenger | 50 | 25 | 16.468 | 14.1849 | 86.14% |
| + Glutathion (100 µg/ml-320 µM) | scavenger | 50 | 25 | 16.454 | 10.4422 | 63.46% |
| + Mannitol (0.5%) | scavenger | 50 | 25 | 16.554 | 1.0667 | 6.44% |
| + Isopropanol (1%) | scavenger | 50 | 25 | 16.572 | 0.8517 | 5.14% |
| + Trolox (4 mM) | scavenger | 50 | 25 | 16.534 | 3.0195 | 18.26% |
| + Trolox (5 mM in DMSO) | scavenger | 50 | 25 | 16.649 | 3.3548 | 20.15% |
| + Tween-80 (0.6 mM) | scavenger | 50 | 25 | 16.550 | 0.8856 | 5.35% |

To analyze the effect of scavenger addition prior to sterilization on the ccfDNA stabilization characteristics of the sterilized stabilizing reagents, samples of 10 ml whole blood from eight donors were collected in 10 ml spray dry K2EDTA tubes and stabilized with 1.7 ml each of the ccfDNA stabilization reagent with or without scavenger. Plasma was generated from 5 ml of stabilized blood samples directly after blood draw. Residual blood was stored for additional 6 days at room temperature before plasma generation. ccfDNA was purified from 2 ml plasma, copy numbers of 18S rDNA gene were determined in triplicates by real time PCR.

Figure 7:
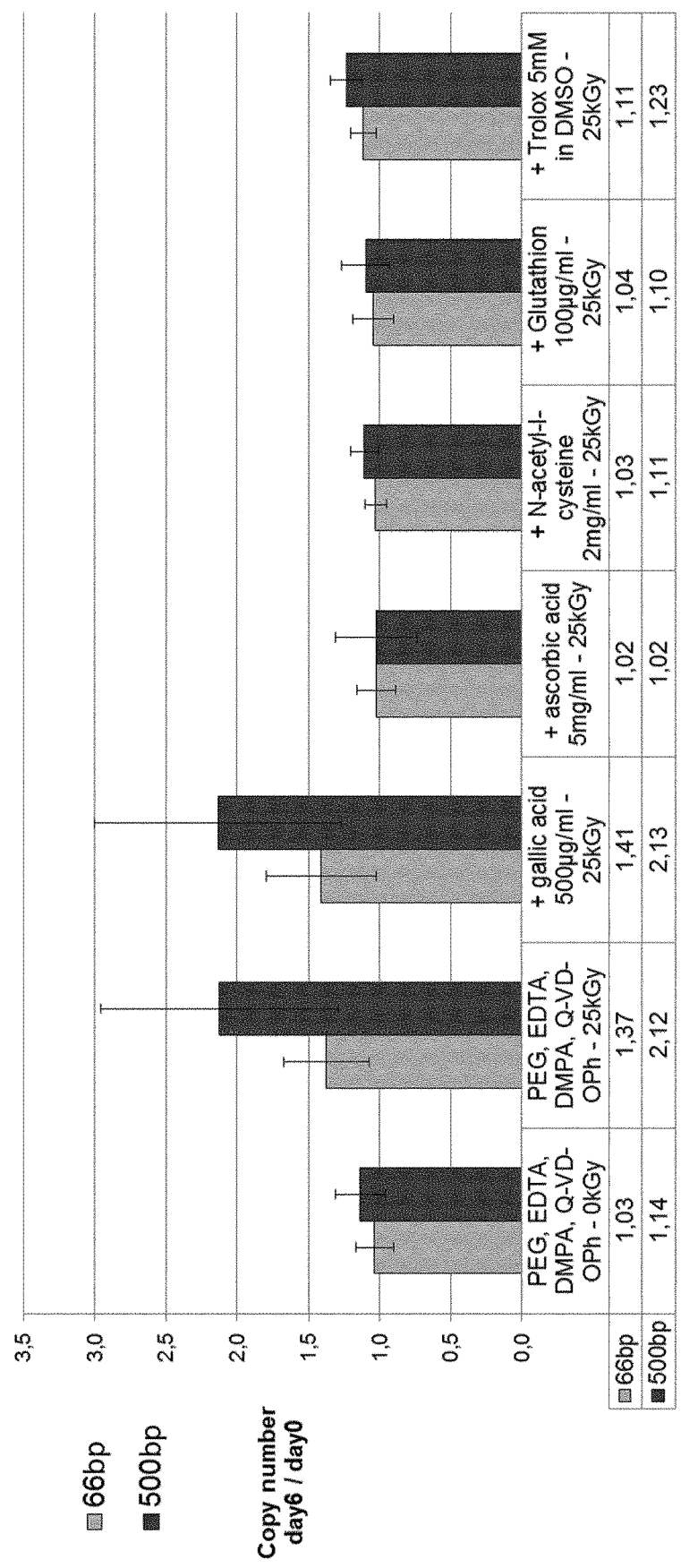
FIG. 7: Effect of gamma irradiation on ccfDNA level in stabilized blood with addition of scavengers. Average change of copy numbers (x fold change) of 66 bp and 500 bp fragments of the 18S rDNA gene in blood samples stabilized with irradiated stabilization reagents after storage.

The scavengers added and the concentrations used are indicated in FIG. 7. Final concentrations in whole blood were 0.42 mM gallic acid, 4.0 mM ascorbic acid, 12 mM N-acetyl-cysteine, 0.05 mM glutathione or 0.73 mM Trolox.

The results are shown in FIG. 7. The average change of copy numbers (x fold change) of 66 bp and 500 bp fragments of the 18S rDNA gene in blood samples stabilized with irradiated stabilization reagents comprising a caspase inhibitor and containing different scavengers. Mean value from 8 donors stored for 6 days at room temperature.

As visible from the higher ratio of total copy numbers of the 66 and 500 bp fragments between day 6 after blood draw and day 0, directly after blood draw, as well as the large standard deviations, gallic acid did not prevent the decreased ccfDNA stabilization induced by gamma irradiation. This is in line with the high degradation rate measured by HPLC (Table 5). In contrast thereto, scavengers such as ascorbic acid, N-acetyl-cysteine, glutathione stabilized the level of ccfDNA as measured by the ratio of copies between day 6 and day 0. Also trolox showed a stabilization effect.

Conclusions:

Surprisingly, only the addition of selected scavengers such as ascorbic acid, N-acetyl-cysteine, glutathione and Trolox prevents degradation of caspase inhibitor caused by gamma irradiation in a stabilization reagent comprising a caspase inhibitor, such as for example a stabilization reagent according to PCT/EP2015/055699.

Likewise surprisingly, addition of certain scavengers such as ascorbic acid, N-acetyl-cysteine, glutathione and Trolox prevents the negative effect of gamma irradiation on the stability level of ccfDNA in blood stabilized with a stabilization reagent comprising a caspase inhibitor.

In contrast, a number of scavengers published to dispose free radicals do not prevent caspase inhibitor degradation caused by irradiation and/or caused an increased level of ccfDNA after blood storage and thus interfered with the stabilization. This applies in particular to gallic acid.

5. Example 5: Overview of Scavenger Activities

An overview of the tested scavengers indicating protection against gamma irradiation on the one hand and effect on ccfDNA stability on the other is shown in Table 6.

TABLE 6

Summary-scavengers and concentrations tested for protection of caspase inhibitor containing stabilization reagents against gamma irradiation. Concentration 1 indicates the concentration of the tested compounds in mg/ml. Concentration 2 indicates the concentration of the tested compounds as weight per volume (w/v) or volume per volume (v/v), depending on whether the compounds are liquids or solids.

| Scavenger | Concentration 1 | Concentration 2 | Effect on ccfDNA stability | Protection against gamma irradiation |
|---|---|---|---|---|
| Ascorbic acid | 5-10 mg/ml | 0.5-1% (w/v) | neutral | high |
| Ascorbic acid | 20 mg/ml | 2% (w/v) | significantly reduced ccfDNA yield | — |
| N-acetyl-L-cysteine | 0.5-10 mg/ml | 0.05-1% (w/v) | neutral | high |
| Glutathion (reduced) | 0.1-1 mg/ml | 0.01-0.1% (w/v) | neutral | high |
| Trolox | 1.25 mg/ml | 0.125% (w/v) | neutral | medium |
| Mannitol | 5 mg/ml | 0.5% (w/v) | | none |
| Isopropanol | — | 1% (v/v) | | none |
| Gallic acid | 0.5-2 mg/ml | 0.2% (w/v) | increased level of ccfDNA after blood storage | none |

TABLE 6-continued

Summary-scavengers and concentrations tested for protection of caspase inhibitor containing stabilization reagents against gamma irradiation. Concentration 1 indicates the concentration of the tested compounds in mg/ml. Concentration 2 indicates the concentration of the tested compounds as weight per volume (w/v) or volume per volume (v/v), depending on whether the compounds are liquids or solids.

| Scavenger | Concentration 1 | Concentration 2 | Effect on ccfDNA stability | Protection against gamma irradiation |
|---|---|---|---|---|
| Tween-80 | 0.74 mg/ml | 0.07% (v/v) | | none |
| Tannic acid | 1 mg/ml | 0.1% | increased level of ccfDNA after blood storage | — |

Conclusions:

Only the addition of specific radical scavengers such as ascorbic acid, N-acetyl-cysteine, glutathione and Trolox, in particular ascorbic acid, N-acetyl-cysteine and glutathione prevents or efficiently reduces the degradation of the caspase inhibitor as a result of sterilization by gamma irradiation. Surprisingly, the addition of these radical scavengers preserves the quality of the ccfDNA stabilization that is achieved with the stabilization compositions that comprise a caspase inhibitor.

Effective scavenging compounds and their effective concentrations differ significantly from previously published radioprotective excipients. For example, gallic acid and tannic acid, but also mannitol, isopropanol and Tween-80 were previously described as scavengers. However they did not provide protection against gamma irradiation for a stabilization reagent comprising a caspase inhibitor. Also, previously described scavengers such as tannic acid and gallic acid interfered with the stabilizing effect of the stabilizing reagent.

6. Example 6: Effect of Scavenger and Caspase Inhibitor Concentration on Caspase Inhibitor Protection During Gamma Irradiation Stabilization reagents according to PCT/EP2015/055699 were produced with or without the addition of radical scavengers in different concentrations and with different concentrations of caspase inhibitor. PAXgene Blood ccfDNA Alpha tubes were produced by filling 1.7 ml of the respective stabilization reagent into a standard Vacutainer. Tubes were sterilized by gamma irradiation with different energy levels. The caspase inhibitor concentration was measured by HPLC before and after irradiation (see Table 7 below).

The Stabilization Reagents Comprised Per Tube:

3.3 µl or 6.6 µl or 9.8 µl of caspase inhibitor (Q-VD-OPh; 18 mg dissolved in 2 ml DMSO; for blood final concentrations of 5, 10 or 15 µM respectively), the reagents further comprised PEG10.000, PEG300, EDTA and DMPA, water ad 1.7 ml.

Scavengers were added to the stabilization reagents in different concentrations and combinations as indicated in Table 7.

TABLE 7

Quantification of caspase inhibitor in stabilization reagent with or without scavenger in different concentrations and with different concentrations of caspase inhibitor before and after gamma irradiation.

| Stab. reagent + scavenger | Conc. scavenger in reagent | Final conc. of casp-inh. [µM] | Irra-diation (kGy) | HPLC Testing [C-Inh] (µg/ml) | % Remaining C-Inh vs w/o irra-diation |
|---|---|---|---|---|---|
| PEG, EDTA, DMPA, Q-VD-OPh | none | 5 | 0 | 14.7 | 100.0% |
| | none | 5 | 10 | 5.6 | 38.4% |
| | none | 5 | 20 | 0.8 | 5.3% |
| | none | 5 | 30 | 0.5 | 3.7% |
| +Ascorbic acid | 1 mg/ml | 5 | 0 | 18.2 | 100.0% |
| | 1 mg/ml | 5 | 10 | 12.7 | 69.7% |
| | 1 mg/ml | 5 | 20 | 7.0 | 38.5% |
| | 1 mg/ml | 5 | 30 | 5.0 | 27.3% |
| +Ascorbic acid | 2 mg/ml | 5 | 0 | 19.4 | 100.0% |
| | 2 mg/ml | 5 | 10 | 15.2 | 78.2% |
| | 2 mg/ml | 5 | 20 | 10.7 | 55.2% |
| | 2 mg/ml | 5 | 30 | 9.5 | 48.9% |
| +Ascorbic acid | 5 mg/ml | 5 | 0 | 19.2 | 100.0% |
| | 5 mg/ml | 5 | 10 | 16.0 | 83.1% |
| | 5 mg/ml | 5 | 20 | 12.8 | 66.7% |
| | 5 mg/ml | 5 | 30 | 12.1 | 63.1% |
| +Ascorbic acid | 5 mg/ml | 10 | 0 | 37.7 | 100.0% |
| | 5 mg/ml | 10 | 10 | 31.2 | 82.7% |
| | 5 mg/ml | 10 | 20 | 26.8 | 71.1% |
| | 5 mg/ml | 10 | 30 | 23.7 | 62.9% |
| +Ascorbic acid | 5 mg/ml | 15 | 0 | 55.5 | 100.0% |
| | 5 mg/ml | 15 | 10 | 46.4 | 83.6% |
| | 5 mg/ml | 15 | 20 | 40.6 | 73.2% |
| | 5 mg/ml | 15 | 30 | 35.5 | 63.9% |
| +Ascorbic acid | 10 mg/ml | 5 | 0 | 18.4 | 100.0% |
| | 10 mg/ml | 5 | 10 | 16.0 | 86.8% |
| | 10 mg/ml | 5 | 20 | 13.5 | 73.5% |
| | 10 mg/ml | 5 | 30 | 13.2 | 71.6% |
| +N-acetyl-L-cysteine | 0.5 mg/ml | 5 | 0 | 19.3 | 100.0% |
| | 0.5 mg/ml | 5 | 10 | 16.2 | 83.8% |
| | 0.5 mg/ml | 5 | 20 | 13.7 | 70.9% |
| | 0.5 mg/ml | 5 | 30 | 12.3 | 63.8% |
| +N-acetyl-L-cysteine | 1 mg/ml | 5 | 0 | 18.5 | 100.0% |
| | 1 mg/ml | 5 | 10 | 15.8 | 85.4% |
| | 1 mg/ml | 5 | 20 | 13.4 | 72.3% |
| | 1 mg/ml | 5 | 30 | 12.5 | 67.5% |
| +N-acetyl-L-cysteine | 2 mg/ml | 5 | 0 | 19.7 | 100.0% |
| | 2 mg/ml | 5 | 10 | 17.2 | 87.3% |
| | 2 mg/ml | 5 | 20 | 15.3 | 77.7% |
| | 2 mg/ml | 5 | 30 | 14.3 | 72.3% |
| +N-acetyl-L-cysteine | 2 mg/ml | 10 | 0 | 37.8 | 100.0% |
| | 2 mg/ml | 10 | 10 | 33.3 | 88.0% |
| | 2 mg/ml | 10 | 20 | 30.7 | 81.2% |
| | 2 mg/ml | 10 | 30 | 27.6 | 73.0% |
| +N-acetyl-L-cysteine | 2 mg/ml | 15 | 0 | 56.0 | 100.0% |
| | 2 mg/ml | 15 | 10 | 50.0 | 89.2% |
| | 2 mg/ml | 15 | 20 | 46.3 | 82.8% |
| | 2 mg/ml | 15 | 30 | 41.2 | 73.6% |
| +N-acetyl-L-cysteine | 4 mg/ml | 5 | 0 | 16.6 | 100.0% |
| | 4 mg/ml | 5 | 10 | 14.8 | 89.1% |
| | 4 mg/ml | 5 | 20 | 13.4 | 80.8% |
| | 4 mg/ml | 5 | 30 | 12.8 | 77.3% |
| +Glutathione | 0.05 mg/ml | 5 | 0 | 19.1 | 100.0% |
| | 0.05 mg/ml | 5 | 10 | 14.1 | 73.7% |
| | 0.05 mg/ml | 5 | 20 | 8.9 | 46.6% |
| | 0.05 mg/ml | 5 | 30 | 6.6 | 34.7% |
| +Glutathione | 0.1 mg/ml | 5 | 0 | 18.8 | 100.0% |
| | 0.1 mg/ml | 5 | 10 | 14.3 | 76.1% |
| | 0.1 mg/ml | 5 | 20 | 9.9 | 52.7% |
| | 0.1 mg/ml | 5 | 30 | 7.5 | 40.1% |
| +Glutathione | 0.1 mg/ml | 10 | 0 | 37.9 | 100.0% |
| | 0.1 mg/ml | 10 | 10 | 29.4 | 77.6% |
| | 0.1 mg/ml | 10 | 20 | 23.3 | 61.5% |
| | 0.1 mg/ml | 10 | 30 | 17.7 | 46.6% |
| +Glutathione | 0.1 mg/ml | 15 | 0 | 55.5 | 100.0% |
| | 0.1 mg/ml | 15 | 10 | 42.7 | 77.0% |
| | 0.1 mg/ml | 15 | 20 | 33.2 | 59.9% |
| | 0.1 mg/ml | 15 | 30 | 25.0 | 45.1% |
| +Glutathione | 0.2 mg/ml | 5 | 0 | 19.9 | 100.0% |
| | 0.2 mg/ml | 5 | 10 | 15.7 | 78.8% |

TABLE 7-continued

Quantification of caspase inhibitor in stabilization reagent with or without scavenger in different concentrations and with different concentrations of caspase inhibitor before and after gamma irradiation.

| Stab. reagent + scavenger | Conc. scavenger in reagent | Final conc. of casp-inh. [µM] | Irra-diation (kGy) | HPLC Testing [C-Inh] (µg/ml) | % Re-maining C-Inh vs w/o irra-diation |
|---|---|---|---|---|---|
| | 0.2 mg/ml | 5 | 20 | 11.9 | 59.8% |
| | 0.2 mg/ml | 5 | 30 | 10.2 | 51.1% |
| +Glutathione | 0.5 mg/ml | 5 | 0 | 18.7 | 100.0% |
| | 0.5 mg/ml | 5 | 10 | 15.4 | 82.0% |
| | 0.5 mg/ml | 5 | 20 | 12.3 | 65.7% |
| | 0.5 mg/ml | 5 | 30 | 11.1 | 59.3% |
| +Glutathione | 1 mg/ml | 5 | 0 | 20.0 | 100.0% |
| | 1 mg/ml | 5 | 10 | 16.8 | 83.7% |
| | 1 mg/ml | 5 | 20 | 13.8 | 68.9% |
| | 1 mg/ml | 5 | 30 | 12.6 | 62.8% |
| +Ascorbic acid & Glutathione | 2 mg/ml AA + 0.2 mg/ml Glut. | 5 | 0 | 18.7 | 100.0% |
| | 2 mg/ml AA + 0.2 mg/ml Glut. | 5 | 10 | 15.7 | 84.0% |
| | 2 mg/ml AA + 0.2 mg/ml Glut. | 5 | 20 | 12.7 | 67.8% |
| | 2 mg/ml AA + 0.2 mg/ml Glut. | 5 | 30 | 11.5 | 61.6% |
| +N-acetyl-L-cysteine & Ascorbic acid | 1 mg/ml NAC + 2 mg/ml AA | 5 | 0 | 17.6 | 100.0% |
| | 1 mg/ml NAC + 2 mg/ml AA | 5 | 10 | 15.5 | 88.3% |
| | 1 mg/ml NAC + 2 mg/ml AA | 5 | 20 | 13.8 | 78.4% |
| | 1 mg/ml NAC + 2 mg/ml AA | 5 | 30 | 13.3 | 75.8% |
| +Glutathione & N-acetyl-L-cysteine | 0.2 mg/ml Glut. + 1 mg/ml NAC | 5 | 0 | 19.4 | 100.0% |
| | 0.2 mg/ml Glut. + 1 mg/ml NAC | 5 | 10 | 16.8 | 86.7% |
| | 0.2 mg/ml Glut. + 1 mg/ml NAC | 5 | 20 | 14.7 | 75.7% |
| | 0.2 mg/ml Glut. + 1 mg/ml NAC | 5 | 30 | 13.2 | 68.4% |
| +N-acetyl-L-cysteine & Ascorbic acid | 2 mg/ml NAC + 0.5 mg/ml Asc. Ac. | 10 | 0 | 30.5 | 100.0% |
| | 2 mg/ml NAC + 0.5 mg/ml Asc. Ac. | 10 | 15 | 26.9 | 88.3% |
| +N-acetyl-L-cysteine & Ascorbic acid | 2 mg/ml NAC + 1 mg/ml Asc. Ac. | 10 | 0 | 30.6 | 100.0% |
| | 2 mg/ml NAC + 1 mg/ml Asc. Ac. | 10 | 15 | 27.4 | 89.6% |
| +N-acetyl-L-cysteine & Glutathione | 0.5 mg/ml NAC + 0.5 mg/ml Glut. | 10 | 0 | 30.9 | 100.0% |
| | 0.5 mg/ml NAC + 0.5 mg/ml Glut. | 10 | 15 | 25.3 | 81.9% |
| +N-acetyl-L-cysteine & Glutathione | 0.5 mg/ml NAC + 1 mg/ml Glut. | 10 | 0 | 29.8 | 100.0% |
| | 0.5 mg/ml NAC + 1 mg/ml Glut. | 10 | 15 | 24.7 | 83.1% |
| +N-acetyl-L-cysteine & Glutathione | 1 mg/ml NAC + 0.5 mg/ml Glut. | 10 | 0 | 31.0 | 100.0% |
| | 1 mg/ml NAC + 0.5 mg/ml Glut. | 10 | 15 | 26.0 | 83.8% |
| +N-acetyl-L-cysteine & Glutathione | 1 mg/ml NAC + 1 mg/ml Glut. | 10 | 0 | 30.3 | 100.0% |
| | 1 mg/ml NAC + 1 mg/ml Glut. | 10 | 15 | 25.6 | 84.7% |
| +N-acetyl-L-cysteine & Glutathione | 2 mg/ml NAC + 0.5 mg/ml Glut. | 10 | 0 | 29.6 | 100.0% |
| | 2 mg/ml NAC + 0.5 mg/ml Glut. | 10 | 15 | 25.7 | 86.8% |
| +N-acetyl-L-cysteine & Glutathione | 2 mg/ml NAC + 1 mg/ml Glut. | 10 | 0 | 29.8 | 100.0% |
| | 2 mg/ml NAC + 1 mg/ml Glut. | 10 | 15 | 26.0 | 87.1% |

Conclusions:

The radical scavengers useful in conjunction with the present invention are effective over a wide concentration range. For the concentration ranges tested (scavenger and caspase inhibitor) the level of protection conferred by a scavenger is largely independent from the caspase inhibitor concentration used. Radical scavengers can be combined to further improve protection.

7. Example 7: Effect of Scavenger Concentration in Sterilized Alpha Tubes on ccfDNA Stabilization A selection of PAXgene Blood ccfDNA Alpha tubes from Example 6 was used for a functional test to determine the ccfDNA stabilization characteristics. N-acetyl-cysteine was added to the stabilization reagents in different concentrations. Alpha tubes with 0.5, 1.0, 2.0 and 4.0 mg/ml N-acetyl-cysteine were prepared as indicated in FIG. 8. The tubes were used non-sterile or were sterilized with different doses of gamma irradiation prior to use. Samples of 10 ml whole blood from four donors each were collected in 10 ml spray dry K2EDTA tubes (non-stabilized controls) and Alpha tubes (sterilized and non-sterilized as controls). The final concentrations of N-acetyl-cysteine in whole blood were 0.44, 0.88, 1.75 and 3.5 mM. Non-stabilized control tubes comprised 1.8 mg/ml K2EDTA (final concentration in whole blood). Plasma was generated from 5 ml of stabilized or non-stabilized blood samples directly after blood draw. Residual blood was stored for additional 6 days at room temperature before plasma generation. ccfDNA was purified on the QIAsymphony from 2 ml plasma, copy numbers of 18S rDNA gene were determined in triplicates by real time PCR.

The Stabilization Reagents Comprised Per Tube:

3.3 µl of caspase inhibitor (Q-VD-OPh; 18 mg dissolved in 2 ml DMSO; for a blood final concentration of 5 µM), the reagents further comprised PEG10.000, PEG300, EDTA and DMPA, water ad 1.7 ml.

The stabilization of ccfDNA was analyzed by quantitative real time PCR. Results are shown in FIG. 8 A, B. The average change and standard deviation of copy numbers (x fold change) of 66 bp and 500 bp fragments of the 18S rDNA gene in non-stabilized EDTA blood and in stabilized blood samples drawn into Alpha tubes with 0.5, 1.0, 2.0 and 4.0 mg/ml N-acetyl-cysteine (non-sterile or sterilized with different doses of gamma irradiation) was compared.

As can be seen from FIG. 8 A, B, N-acetyl-cysteine at all concentrations tested provided excellent protection over a wide range of irradiation doses, and even at high doses of 30 kGy. Moreover, as can be seen from the non-irradiated (0Gy) stabilizing reagents comprising N-acetyl-L-cysteine, addition of N-acetyl-cysteine does not interfere with the stabilization of extracellular nucleic acids by the stabilization reagent.

Conclusion:

N-acetyl-cysteine works in a broad range of concentration for protection against gamma-irradiation. With addition of the radical scavenger into the stabilization reagent, the dose-dependent effect of gamma irradiation on ccfDNA stability is eliminated. N-acetyl-cysteine does not interfere with the stabilization of extracellular nucleic acids by the stabilization reagent and its use as protective agent to prevent degradation of the caspase inhibitor during irradiation is preferred.

8. Example 8: Effect of Addition of the Water-Soluble Vitamin B6 as Scavenger on ccfDNA Level Stabilization after Gamma Irradiation The effect of addition of vitamin B6 as a scavenger for prevention of caspase inhibitor degradation during sterilization by gamma irradiation was analyzed. Stabilization reagents were produced with or without the addition of vitamin B6 and sterilized in bulk by gamma irradiation with 30 kGy.

Samples of 10 ml whole blood from eight donors were collected in 10 ml spray dry K2EDTA tubes and stabilized by addition of 1.7 ml sterilized ccfDNA stabilization reagent with or without scavenger directly after blood draw. Blood samples were stored for 5 days at room temperature before plasma generation. Automated purification of ccfDNA on the QIAsymphony with stabilized blood samples was performed with the QIAsymphony PAXgene Blood ccfDNA kit and the protocol PAXcircDNA_2400_LAF (PreAnalytiX) from 2.4 ml plasma. As a control, ccfDNA purification from unstabilized blood samples was performed with the QIAsymphony Circulating DNA protocol and kit (QIAGEN) from 2.0 ml plasma. A stabilization reagent produced with the addition of vitamin B6, but that had not been sterilized, was also included into the experiment. Total copy numbers of 18S rDNA gene (500 bp fragment) were determined in triplicates by real time PCR.

The Stabilization Reagents Comprised (for 10 ml K2EDTA Whole Blood):

3.28 µl caspase inhibitor (Q-VD-OPh; 1 mg dissolved in 111 µl DMSO), the reagents further comprised PEG, EDTA and DMPA, water ad 1.7 ml. Suitable polyethylene glycols, such as PEG 300 and PEG 10.000, were described above. For the stabilization reagents that comprised the scavenger vitamin B6 (pyridoxine), vitamin B6 (pyridoxine) was added to the stabilization reagents in a concentration of 2 mg/ml. Final caspase inhibitor (Q-VD-OPh) concentration in the stabilized blood was approx. 5 µM. Final concentration of vitamin B6 (pyridoxine) in whole blood was approx. 1.7 mM.

The mean average total copy numbers of 500 bp fragment of the 18S rDNA gene in blood samples from 8 donors stored for 5 days at room temperature are shown in FIG. 9. Blood samples were stabilized with stabilization reagents with (left bar) or without (third bar from left) vitamin B6 as scavenger. These stabilization reagents had been sterilized (30 kGy). As controls, a stabilization reagent with vitamin B6 but that had not been sterilized (second bar from left) and unstabilized EDTA blood (fourth bar from left) were included.

In blood samples stabilized with stabilization reagents (irradiated as well as unirradiated) containing vitamin B6 as scavenger, the number of 500 bp fragments of the 18S rDNA gene was only half compared to the stabilization reagent without scavenger (irradiated). Since naturally occurring ccfDNA has a size of around 150 bp, longer fragments are derived from lysed or apoptotic white blood cells. The low number of 500 bp fragments of the 18S rDNA gene observed in blood samples stabilized with stabilization reagents comprising vitamin B6 as scavenger hence indicates that the blood was efficiently stabilized. In particular, the stabilization with the irradiated stabilization reagent comprising vitamin B6 was superior to stabilization observed with the irradiated stabilization reagent without scavenger. This indicates that stabilization properties of the stabilization reagent were efficiently protected by vitamin B6 during irradiation. In the negative control with unstabilized blood, the 500 bp fragment copy number was even 25-50 fold higher compared to the stabilized blood samples.

Conclusions:

Like the scavengers ascorbic acid, N-acetyl-L-cysteine, glutathione and Trolox, also the water-soluble vitamin B6 prevents the negative effect of gamma irradiation on the stability level of ccfDNA in blood stabilized with a stabilization reagent comprising a caspase inhibitor. Hence the addition of vitamin B6 protects the stabilization composition during irradiation and allows to prepare a sterilized stabilization composition with good stabilization properties.

9. Example 9: Effect of Different Caspase Inhibitors on ccfDNA Level Stabilization and Efficient Protection of Different Caspase Inhibitors During Sterilization The effect of addition of different caspase inhibitors (Boc-D-(OMe)-FMK and Z-VAD (OMe)-FMK) for stabilization of ccfDNA level in whole blood was tested. Also, the protection of these different caspase inhibitors from degradation during sterilization by irradiation was analyzed.

Stabilization reagents were produced with addition of Boc-D-(OMe)-FMK or Z-VAD (OMe)-FMK as caspase inhibitor with or without the scavenger N-acetyl-L-cysteine (NAC) as protector for sterilization. In cases where NAC was added, reagents were sterilized in bulk by gamma irradiation with 30 kGy. Stabilization of ccfDNA levels was compared to the PAXgene Blood ccfDNA tube (PreAnalytiX) and to unstabilized EDTA blood.

Samples of 10 ml whole blood from six donors were collected in 10 ml spray dry K2EDTA tubes and stabilized by addition of 1.7 ml stabilization reagent as well as collected into PAXgene Blood ccfDNA tubes or kept unstable. Blood sample were stored for 5 days at room temperature before plasma generation. Automated purification of ccfDNA on the QIAsymphony with stabilized blood samples was performed with the QIAsymphony PAXgene Blood ccfDNA kit and the protocol PAXcircDNA_2400_LAF (PreAnalytiX) from 2.4 ml plasma. As a control ccfDNA purification from unstabilized blood samples was performed with the QIAsymphony Circulating DNA protocol and kit (QIAGEN) from 2.0 ml plasma. Total copy numbers of 18S rDNA gene (500 bp fragment) were determined in triplicates by real time PCR.

The Stabilization Reagents Comprised (for 10 ml K2EDTA Whole Blood):

3.280 caspase inhibitor (Boc-D-(OMe)-FMK with 1 mg dissolved in 217 µl DMSO or Z-VAD (OMe)-FMK with 1 mg dissolved in 122 µl DMSO) the reagents further comprised PEG, EDTA and DMPA, water ad 1.7 ml. Suitable polyethylene glycols, such as PEG 300 and PEG 10.000, were described above. For the stabilization reagents that comprised N-acetyl-L-cysteine (NAC) as a scavenger, N-acetyl-L-cysteine was added to the stabilization reagents in a concentration of 0.5 mg/ml. Final caspase inhibitor concentration in the stabilized blood was approx. 5 µM. Final concentration of scavenger in whole blood was approx. 0.44 mM.

The mean average total copy numbers of 500 bp fragment of the 18S rDNA gene in blood samples from 6 donors stored for 5 days at room temperature are shown in FIG. 10. Blood samples were stabilized with stabilization reagents comprising different caspase inhibitors. Left bar: stabilization reagent comprising the caspase inhibitor Boc-D-(OMe)-FMK (non-sterilized); second bar from left: stabilization reagent comprising the caspase inhibitor Boc-D-(OMe)-FMK and N-acetyl-cysteine as scavenger (sterilized); third bar from left: stabilization reagent comprising the caspase inhibitor Z-VAD (OMe)-FMK (non-sterilized); fourth bar from left: stabilization reagent comprising the caspase inhibitor Z-VAD (OMe)-FMK and N-acetyl-cysteine as scavenger (sterilized); fifth bar from left: PAXgene Blood ccfDNA Tube; sixth bar from left: unstabilized EDTA blood.

As can be seen from FIG. 10, in blood samples stabilized with caspase inhibitors Boc-D-(OMe)-FMK or Z-VAD (OMe)-FMK copy numbers of the 500 bp fragment, which can be considered to be descended from apoptotic cells, were comparable to the fragment numbers in blood stabilized with the PAXgene Blood ccfDNA Tube. Thus, stabilization reagents comprising the caspase inhibitors Boc-D-(OMe)-FMK and Z-VAD (OMe)-FMK achieve good stabilization characteristics. Addition of the scavenger N-acetyl-L-cysteine (NAC) efficiently protected the caspase inhibitors Boc-D-(OMe)-FMK and Z-VAD (OMe)-FMK from gamma-irradiation. In the negative control with unstabilized blood, the 500 bp fragment copy number was 50-100 fold higher compared to the stabilized blood samples.

Conclusions:

Like the stabilizing reagent comprise caspase inhibitor Q-VD-OPh (see for example FIG. 9), stabilizing reagents comprising other caspase inhibitors such as Boc-D-(OMe)-FMK or Z-VAD (OMe)-FMK prevent the release of genomic DNA into plasma and thereby stabilize the ccfDNA level. The compounds used according to the invention, such as in particular N-acetyl-cysteine, protect stabilization reagents comprising different caspase inhibitors (like Q-VD-OPh, Boc-D-(OMe)-FMK or Z-VAD (OMe)-FMK) during gamma irradiation, and negative effects of gamma-irradiation can be prevented by addition of a radical scavenger such as N-acetyl-L-cysteine.

The invention claimed is:

1. A method for producing a sterilized composition, wherein the sterilized composition is capable of stabilizing an extracellular nucleic acid population of a biological sample, the method comprising:
  a) providing a composition comprising:
    i. at least one caspase inhibitor, and
    ii. at least one compound selected from a thioalcohol that is N-acetyl-cysteine or glutathione, a water-soluble vitamin, and a water-soluble vitamin E derivate; and
  b) irradiating the composition for sterilization,
  wherein the composition provided in a) and irradiated for sterilization in b) does not comprise a biological sample to be stabilized from a human or animal subject.

2. The method according to claim 1, wherein the method has one or more of the following characteristics:
  a) the composition is irradiated by ionizing irradiation;
  b) the composition is irradiated by gamma irradiation, electron beam irradiation, or X-ray;
  c) the composition is irradiated with an irradiation dose of 5 kGy to 35 kGy, 6 kGy to 30 kGy, 7 kGy to 26 kGy, about 8 kGy to about 25 kGy, or about 8 kGy to about 15 kGy;
  d) sterilization by irradiation results in a sterility assurance level (SAL) of the composition of $10^{-6}$ or less;
  e) the composition is irradiated in a liquid, optionally aqueous, form;
  f) the composition is prepared in solid form and is dissolved prior to irradiation to provide a liquid composition which is optionally aqueous;
  g) the composition is prepared and irradiated in a liquid, optionally aqueous, form;
  h) the composition is aqueous, has an acidic pH and/or is buffered; and/or
  i) the composition has a pH of 4.0 to 7.0, a pH of 4.1 to 6.9, a pH of 4.2 to 6.8, a pH of 4.3 to 6.6, a pH of 4.4 to 6.3, a pH of 4.5 to 6.0, or a pH of 4.5 to 5.5.

3. The method according to claim 1, wherein the composition comprises the at least one compound selected from a thioalcohol that is N-acetyl-cysteine or glutathione, a water-soluble vitamin, and a water-soluble vitamin E derivative in a concentration of less than 20 mg/ml, 15 mg/ml or less, 10 mg/ml or less, 7 mg/ml or less, 3 mg/ml or less, or 1.5 mg/ml or less, and/or
  wherein the composition comprises:
    i. a compound selected from N-acetyl-cysteine, glutathione, wherein the glutathione is optionally in reduced form, a B vitamin, optionally vitamin B6, ascorbic acid, and trolox;
    ii. a compound selected from N-acetyl-cysteine, glutathione, ascorbic acid, and trolox, wherein the glutathione is optionally in reduced form;
    iii. a compound selected from N-acetyl-cysteine, glutathione, wherein the glutathione is optionally in reduced form, a B vitamin, optionally vitamin B6, and ascorbic acid;
    iv. a compound selected from N-acetyl-cysteine, glutathione, and ascorbic acid, wherein the glutathione is optionally in reduced form; or
    v. N-acetyl-cysteine.

4. The method according to claim 1, the method comprising:
  a) providing a composition comprising:
    i. at least one caspase inhibitor, wherein optionally the caspase inhibitor has one or more of the following characteristics:
      a) the caspase inhibitor is a pancaspase inhibitor;
      b) the caspase inhibitor comprises a modified caspase-specific peptide;
      c) the caspase inhibitor comprises a modified caspase-specific peptide that is modified, optionally at the carboxyl terminus, with an O-Phenoxy (OPh) group;
      d) the caspase inhibitor comprises a modified caspase-specific peptide that is modified, optionally at the N-terminus, with a glutamine (Q) group;
      e) the caspase inhibitor is selected from the group consisting of Q-VD-OPh, Boc-D-(0Me)-FMK and Z-Val-Ala-Asp(OMe)-FMK;
      f) the caspase inhibitor is selected from the group consisting of Q-VD-OPh and Z-Val-Ala-Asp (OMe)-FMK; and/or g) the caspase inhibitor is Q-VD-OPh, and
ii. at least one of
aa) N-acetyl-cysteine in a concentration of 0.05 mg/ml to 15 mg/ml, 0.1 mg/ml to 10 mg/ml, 0.1 mg/ml to 7.5 mg/ml, 0.1 mg/ml to 5 mg/ml, 0.1 mg/ml to 2 mg/ml, 0.2 mg/ml to 1 mg/ml, or 0.3 mg/ml to 0.8 mg/ml;
ab) glutathione in a concentration of 0.03 mg/ml to 10 mg/ml, 0.075 mg/ml to 5 mg/ml, 0.15 mg/ml to 4 mg/ml or 0.4 mg/ml to 1.3 mg/ml, wherein the glutathione is optionally in reduced form;
ac) ascorbic acid in a concentration of less than 20 mg/ml, optionally 0.1 mg/ml to 15 mg/ml, 1 mg/ml to 13 mg/ml, 1.5 mg/ml to 12 mg/ml, or 2 mg/ml to 11 mg/ml;
ad) a B vitamin, optionally vitamin B6, in a concentration of 0.1 mg/ml to 15 mg/ml, 0.1 mg/ml to 14 mg/ml, 0.1 mg/ml to 11 mg/ml, 0.2 mg/ml to 7.5 mg/ml, or 0.2 mg/ml to 2 mg/ml; and
ae) trolox in a concentration of 0.5 mg/ml to 5 mg/ml, 0.75 mg/ml to 3 mg/ml, 0.9 mg/ml to 2 mg/ml, or 1 mg/ml to 1.4 mg/ml; and
b) irradiating the composition for sterilization.

5. The method according to claim 4, wherein the composition is irradiated in a liquid, optionally aqueous form, and/or wherein the composition is irradiated by gamma irradiation for sterilization.

6. The method according to claim 1, wherein the composition has one or more of the following characteristics:
a) the composition comprises N-acetyl-cysteine;
b) the composition comprises N-acetyl-cysteine in a concentration of 0.05 mg/ml to 15 mg/ml, 0.1 mg/ml to 10 mg/ml, 0.1 mg/ml to 7.5 mg/ml, 0.1 mg/ml to 5 mg/ml, 0.1 mg/ml to 2 mg/ml, 0.2 mg/ml to 1 mg/ml, or 0.3 mg/ml to 0.8 mg/ml;
c) the composition comprises N-acetyl-cysteine and is sterilized by irradiation in a liquid, optionally aqueous, form; and/or
d) the composition comprises N-acetyl-cysteine in a concentration of 0.05 mg/ml to 15 mg/ml, 0.1 mg/ml to 10 mg/ml, 0.1 mg/ml to 7.5 mg/ml, 0.1 mg/ml to 5 mg/ml, 0.1 mg/ml to 2 mg/ml, 0.2 mg/ml to 1 mg/ml, or 0.3 mg/ml to 0.8 mg/ml and is sterilized in an aqueous, liquid form.

7. The method according to claim 1, wherein the composition has one or more of the following characteristics:
a) the composition comprises glutathione;
b) the composition comprises glutathione in reduced form;
c) the composition comprises glutathione in a concentration of 0.03 mg/ml to 10 mg/ml, 0.075 mg/ml to 5 mg/ml, 0.15 mg/ml to 4 mg/ml, or 0.4 mg/ml to 1.3 mg/ml, wherein the glutathione is optionally in reduced form;
d) the composition comprises glutathione and is sterilized in a liquid, optionally aqueous, form, wherein the glutathione is optionally in reduced form; and/or
e) the composition comprises glutathione in a concentration of 0.03 mg/ml to 10 mg/ml, 0.075 mg/ml to 5 mg/ml, 0.15 mg/ml to 4 mg/ml, or 0.4 mg/ml to 1.3 mg/ml and is sterilized in an aqueous, liquid form, wherein the glutathione is optionally in reduced form.

8. The method according to claim 1, wherein the composition has one or more of the following characteristics:
a) the composition comprises at least one water-soluble vitamin, wherein optionally the water-soluble vitamin is selected from ascorbic acid, vitamin B1, vitamin B2, vitamin B3, vitamin B6, folate or folic acid, vitamin B12, biotin and pantothenic acid;
b) the composition comprises at least one water-soluble vitamin, optionally selected from ascorbic acid, vitamin B1, vitamin B2, vitamin B3, vitamin B6, folate or folic acid, vitamin B12, biotin and pantothenic acid, in a concentration of less than 20 mg/ml, optionally 0.1 mg/ml to 15 mg/ml, 1 mg/ml to 13 mg/ml, 1.5 mg/ml to 12 mg/ml, or 2 mg/ml to 11 mg/ml;
c) the composition comprises at least one water-soluble vitamin and is sterilized in a liquid, optionally aqueous, form;
d) the composition comprises ascorbic acid and is sterilized in a liquid, optionally aqueous, form;
e) the composition comprises at least one water-soluble vitamin in a concentration of less than 20 mg/ml, optionally 0.1 mg/ml to 15 mg/ml, 1 mg/ml to 13 mg/ml, 1.5 mg/ml to 12 mg/ml, or 2 mg/ml to 11 mg/ml mg/ml and is sterilized in a liquid, optionally aqueous, form;
f) the composition comprises ascorbic acid in a concentration of less than 20 mg/ml, wherein the concentration can be selected from 0.1 mg/ml to 15 mg/ml, 1 mg/ml to 13 mg/ml, 1.5 mg/ml to 12 mg/ml, or 2 mg/ml to 11 mg/ml and wherein the composition is sterilized by irradiation in a liquid, optionally aqueous, form;
g) the composition comprises a B vitamin, optionally Vitamin B6, in a concentration of 0.1 mg/ml to 15 mg/ml, 0.1 mg/ml to 14 mg/ml, 0.1 mg/ml to 11 mg/ml, 0.2 mg/ml to 7.5 mg/ml, or 0.2 mg/ml to 2 mg/ml; and/or
h) the composition comprises a B vitamin, optionally Vitamin B6, in a concentration of 0.1 mg/ml to 15 mg/ml, 0.1 mg/ml to 14 mg/ml, 0.1 mg/ml to 11 mg/ml, 0.2 mg/ml to 7.5 mg/ml, or 0.2 mg/ml to 2 mg/ml, and wherein the composition is sterilized by irradiation in a liquid, optionally aqueous, form.

9. The method according to claim 1, wherein the composition has one or more of the following characteristics:
a) the composition comprises a water-soluble vitamin E derivative, wherein optionally the water-soluble vitamin E derivative is trolox;
b) the composition comprises trolox;
c) the composition comprises a water-soluble vitamin E derivative, optionally trolox, in a concentration of 0.5 mg/ml to 5 mg/ml, 0.75 mg/ml to 3 mg/ml, 0.9 mg/ml to 2 mg/ml, or 1 mg/ml to 1.4 mg/ml;
d) the composition comprises a water-soluble vitamin E derivative, optionally trolox, and is sterilized in a liquid, optionally aqueous, form;
e) the composition comprises a water-soluble vitamin E derivative, optionally trolox, in a concentration of 0.5 mg/ml to 5 mg/ml, 0.75 mg/ml to 3 mg/ml, 0.9 mg/ml to 2 mg/ml, or 1 mg/ml to 1.4 mg/ml and is sterilized in a liquid, optionally aqueous, form.

10. The method according to claim 1, wherein the caspase inhibitor has one or more of the following characteristics:
a) the caspase inhibitor is a pancaspase inhibitor;
b) the caspase inhibitor comprises a modified caspase-specific peptide;
c) the caspase inhibitor comprises a modified caspase-specific peptide that is modified, optionally at the carboxyl terminus, with an O-Phenoxy (OPh) group;
d) the caspase inhibitor comprises a modified caspase-specific peptide that is modified, optionally at the N-terminus, with a glutamine (Q) group;

e) the caspase inhibitor is selected from the group consisting of Q-VD-OPh, Boc-D-(OMe)-FMK and Z-Val-Ala-Asp(OMe)-FMK;
f) the caspase inhibitor is selected from the group consisting of Q-VD-OPh and Z-Val-Ala-Asp(OMe)-FMK; and/or
g) the caspase inhibitor is Q-VD-OPh.

11. The method according to claim 1, wherein the composition further comprises one or more of:
   a) an anticoagulant and/or a chelating agent, optionally EDTA;
   b) a poly(oxyethylene) polymer as stabilizing agent; and/or
   c) at least one primary, secondary or tertiary amide.

12. The method according to claim 1, wherein the composition further comprises at least one poly(oxyethylene) polymer, optionally wherein the composition has one or more of the following characteristics:
   a) the poly(oxyethylene) polymer is a polyethylene glycol, optionally unsubstituted polyethylene glycol;
   b) the composition comprises a poly(oxyethylene) polymer which is a high molecular weight poly(oxyethylene) polymer having a molecular weight of at least 1500;
   c) the composition comprises at least one poly(oxyethylene) polymer having a molecular weight below 1500, optionally wherein the at least one poly(oxyethylene) polymer is a low molecular weight poly(oxyethylene) polymer having a molecular weight of 1000 or less or has a molecular weight that lies in a range selected from 100 to 800, 150 to 700, 200 to 600 and 200 to 500;
   d) the composition comprises a poly(oxyethylene) polymer which is a high molecular weight poly(oxyethylene) polymer having a molecular weight of at least 1500 and at least one further poly(oxyethylene) polymer that is at least 100, optionally at least 200, at least 300 or at least 400 below the molecular weight of the high molecular weight poly(oxyethylene) polymer, wherein said further poly(oxyethylene) polymer optionally is a low molecular weight poly(oxyethylene) polymer having a molecular weight of 1000 or less; and/or
   e) the composition comprises a poly(oxyethylene) polymer which is a high molecular weight poly(oxyethylene) polymer and a poly(oxyethylene) polymer which is a low molecular weight poly(oxyethylene) polymer, wherein said high molecular weight poly(oxyethylene) polymer has a molecular weight that lies in a range selected from 1500 to 50000, 1500 to 40000, 2000 to 30000, 2500 to 25000, 3000 to 20000, 3500 to 15000 and 4000 to 12500 and/or wherein said low molecular weight poly(oxyethylene) polymer has a molecular weight of 1000 or less and wherein optionally, the molecular weight lies in a range selected from 100 to 1000, 150 to 800, 150 to 700, 200 to 600 and 200 to 500.

13. The method according to claim 1, wherein the composition comprises:
   a) at least one primary, secondary or tertiary amide;
   b) at least one compound according to formula 1

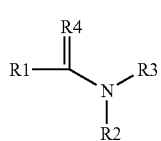

formula 1 wherein R1 is a hydrogen residue or an alkyl residue, optionally a C1-C5 alkyl residue, a C1-C4 alkyl residue, a C1-C3 alkyl residue or a C1-C2 alkyl residue, R2 and R3 are identical or different and are selected from a hydrogen residue and a hydrocarbon residue, optionally an alkyl residue, with a length of the carbon chain of 1 20 atoms arranged in a linear or branched manner, and R4 is an oxygen, sulphur or selenium residue;
   c) at least one primary, secondary or tertiary amide according to formula 1

formula 1 wherein R1 is a hydrogen residue or an alkyl residue, optionally a C1-C5 alkyl residue, a C1-C4 alkyl residue, a C1-C3 alkyl residue or a C1-C2 alkyl residue, R2 and R3 are identical or different and are selected from a hydrogen residue and a hydrocarbon residue, optionally an alkyl residue, with a length of the carbon chain of 1 20 atoms arranged in a linear or branched manner, and R4 is an oxygen, sulphur or selenium residue;
   d) at least one primary, secondary or tertiary carboxylic acid amide according to formula 1

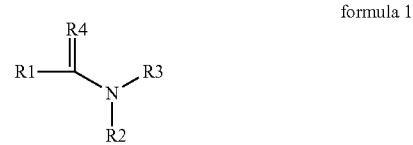

formula 1 wherein R1 is a hydrogen residue or an alkyl residue, optionally a C1-C5 alkyl residue, a C1-C4 alkyl residue, a C1-C3 alkyl residue or a C1-C2 alkyl residue, R2 and R3 are identical or different and are selected from a hydrogen residue and a hydrocarbon residue, optionally an alkyl residue, with a length of the carbon chain of 1-20 atoms arranged in a linear or branched manner, and R4 is an oxygen, sulphur or selenium residue; and/or
   e) a N,N-dialkylpropanamide, optionally N,N-dimethlypropanamide, and/or butanamide.

14. The method according to claim 1, wherein the sterilized composition further has one or more of the following characteristics:
   i) it is capable of stabilizing intracellular nucleic acids comprised in a cell-containing sample, optionally intracellular RNA and/or intracellular DNA;
   ii) it is capable of reducing the degradation of nucleic acids present in a cell-containing sample due to the stabilization;
   iii) it is capable of stabilizing the transcriptome and/or transcript levels in cells contained in the sample; and/or
   iv) it is capable of stabilizing the transcriptome and/or transcript levels in cells contained in the sample and is capable of stabilizing the transcript level of one or more marker genes selected from c-fos, IL-1beta, IL-8 and p53 for at least 12h, for at least 24h or for at least 48h upon stabilization.

15. The method according to claim 1, wherein the sterilized composition does not induce lysis of nucleated cells or cells in general; and/or
    wherein the sterilized composition does not comprise a cross-linking agent that induces nucleic acid-nucleic acid, protein-nucleic acid and/or protein-protein cross-links and does not involve the use of a formaldehyde releaser.

16. The method according to claim 1, wherein the sterilized composition has the following stabilization characteristics:
    a) the stabilization allows the isolation of cells from the stabilized cell-containing sample;
    b) the cell-containing sample is a blood sample and wherein cells contained in the blood sample are stabilized;
    c) the cell-containing sample is a blood sample and wherein white blood cells are stabilized;
    d) the morphology of cells is preserved;
    e) the morphology of nucleated cells is preserved;
    f) the sample is a blood sample and contained lymphocytes and/or monocytes are stabilized;
    g) cell surface epitopes are preserved; and/or
    h) cell surface proteins are preserved.

17. A sterilized composition capable of stabilizing an extracellular nucleic acid population of a biological sample, the sterilized composition comprising
    i. at least one caspase inhibitor, and
    ii. at least one compound selected from a thioalcohol that is N-acetyl-cysteine or glutathione, a water-soluble vitamin, and a water-soluble vitamin E derivate,
    wherein the sterilized composition does not comprise a biological sample to be stabilized from a human or animal subject.

18. A method for stabilizing an extracellular nucleic acid population comprised in a cell-containing biological sample comprising:
    a) obtaining a sterilized composition capable of stabilizing an extracellular nucleic acid population of a biological sample according to the method defined in claim 1, or providing a sterilized composition, wherein the composition is capable of stabilizing an extracellular nucleic acid population of a biological sample, wherein the sterilized composition comprises:
        i. at least one caspase inhibitor, and
        ii. at least one compound selected from a thioalcohol that is N-acetyl-cysteine or glutathione, a water-soluble vitamin, and a water-soluble vitamin E derivate, and
        wherein the sterilized composition does not comprise a biological sample to be stabilized from a human or animal subject; and
    b) contacting the cell-containing biological sample with the sterilized composition for stabilization.

19. The method of claim 18, further comprising:
    c) isolating extracellular nucleic acids.

20. A method for isolating nucleic acids and/or cells from a stabilized cell-containing biological sample comprising:
    a) stabilizing a cell-containing biological sample, wherein stabilization comprises
        i) obtaining a sterilized composition according to a method defined in claim 1; or
        ii) providing a sterilized composition, wherein the composition is capable of stabilizing an extracellular nucleic acid population of a biological sample, wherein the sterilized composition comprises:
            i. at least one caspase inhibitor, and
            ii. at least one compound selected from a thioalcohol that is N-acetyl-cysteine or glutathione, a water-soluble vitamin, and a water-soluble vitamin E derivate, and
            wherein the sterilized composition does not comprise a biological sample to be stabilized from a human or animal subject;
    and contacting the cell-containing biological sample with the sterilized composition; and
    b) isolating nucleic acids and/or cells from the stabilized sample.

21. The method according to claim 20, having one or more of the following characteristics:
    aa) step b) comprises isolating intracellular RNA and/or intracellular DNA, optionally genomic DNA;
    bb) step b) comprises isolating extracellular nucleic acids;
    cc) the method comprises removing cells from the stabilized sample and isolating nucleic acids from the removed cells; and/or
    dd) step b) comprises isolating cells from the stabilized sample.

22. A sample collection device comprising a composition according to claim 17, wherein optionally the sample collection device is sterilized and/or wherein optionally, the sample collection device is a container or a sample collection tube.

23. The composition of claim 17, wherein the composition has one or more of the following characteristics:
    a) the composition is liquid, optionally aqueous;
    b) the composition has an acidic pH and/or is buffered;
    c) the composition has a pH of 4.0 to 7.0, a pH of 4.1 to 6.9, a pH of 4.2 to 6.8, a pH of 4.3 to 6.6, a pH of 4.4 to 6.3, a pH of 4.5 to 6.0, or a pH of 4.5 to 5.5;
    d) the composition is irradiation sterilized, optionally gamma irradiation sterilized;
    e) the composition has a sterility assurance level (SAL) of 10' or less; and/or
    f) the composition is obtainable by:
        fa) providing a composition:
            i. at least one caspase inhibitor, and
            at least one compound selected from a thioalcohol that is N-Acetyl-cysteine or glutathione, a water-soluble vitamin and a water-soluble vitamin F derivate; and
        fb) irradiating the composition for sterilization.

24. The composition of claim 17, wherein
    i) the at least one caspase inhibitor has one or more of the following characteristics:
        a) the caspase inhibitor is a pancaspase inhibitor;
        b) the caspase inhibitor comprises a modified caspase-specific peptide;
        c) the caspase inhibitor comprises a modified caspase-specific peptide that is modified, optionally at the carboxyl terminus, with an O-Phenoxy (OPh) group;
        d) the caspase inhibitor comprises a modified caspase-specific peptide that is modified, optionally at the N-terminus, with a glutamine (Q) group;
        e) the caspase inhibitor is selected from the group consisting of Q-VD-OPh, Boc-D-(OMe)-FMK and Z-Val-Ala-Asp(OMe)-FMK;
        f) the caspase inhibitor is selected from the group consisting of Q-VD-OPh and Z-Val-Ala-Asp(OMe)-FMK; and/or g) the caspase inhibitor is Q-VD-OPh;
and/or
ii) the composition comprises at least one of
  a) N-acetyl-cysteine, optionally in a concentration of 0.05 mg/ml to 15 mg/ml, 0.1 mg/ml to 10 mg/ml, 0.1 mg/ml to 7.5 mg/ml, 0.1 mg/ml to 5 mg/ml, 0.1 mg/ml to 2 mg/ml, 0.2 mg/ml to 1 mg/ml, or 0.3 mg/ml to 0.8 mg/ml;
  b) glutathione, optionally in a concentration of 0.03 mg/ml to 10 mg/ml, 0.075 mg/ml to 5 mg/ml, 0.15 mg/ml to 4 mg/ml or 0.4 mg/ml to 1.3 mg/ml, wherein the glutathione is optionally in reduced form;
  c) ascorbic acid, optionally in a concentration of less than 20 mg/ml, optionally 0.1 mg/ml to 15 mg/ml, 1 mg/ml to 13 mg/ml, 1.5 mg/ml to 12 mg/ml, or 2 mg/ml to 11 mg/ml;
  d) a B vitamin, optionally in a concentration of 0.1 mg/ml to 15 mg/ml, 0.1 mg/ml to 14 mg/ml, 0.1 mg/ml to 11 mg/ml, 0.2 mg/ml to 7.5 mg/ml, or 0.2 mg/ml to 2 mg/ml, wherein the B vitamin optionally is vitamin B6;
  e) a water-soluble vitamin E derivative, optionally in a concentration of 0.5 mg/ml to 5 mg/ml, 0.75 mg/ml to 3 mg/ml, 0.9 mg/ml to 2 mg/ml, or 1 mg/ml to 1.4 mg/ml, wherein the water-soluble vitamin E derivative optionally is trolox.

25. The composition of claim 17, wherein the composition further comprises one or more of:
  a) an anticoagulant and/or a chelating agent, optionally EDTA;
  b) a poly(oxyethylene) polymer as stabilizing agent; and/or
  c) at least one primary, secondary or tertiary amide.

26. The composition of claim 17, wherein the composition further comprises at least one poly(oxyethylene) polymer, optionally wherein the composition has one or more of the following characteristics:
  a) the poly(oxyethylene) polymer is a polyethylene glycol, optionally unsubstituted polyethylene glycol;
  b) the composition comprises a poly(oxyethylene) polymer which is a high molecular weight poly(oxyethylene) polymer having a molecular weight of at least 1500;
  c) the composition comprises at least one poly(oxyethylene) polymer having a molecular weight below 1500, optionally wherein the at least one poly(oxyethylene) polymer is a low molecular weight poly(oxyethylene) polymer having a molecular weight of 1000 or less or has a molecular weight that lies in a range selected from 100 to 800, 150 to 700, 200 to 600 and 200 to 500;
  d) the composition comprises a poly(oxyethylene) polymer which is a high molecular weight poly(oxyethylene) polymer having a molecular weight of at least 1500 and at least one further poly(oxyethylene) polymer that is at least 100, optionally at least 200, at least 300 or at least 400 below the molecular weight of the high molecular weight poly(oxyethylene) polymer, wherein said further poly(oxyethylene) polymer optionally is a low molecular weight poly(oxyethylene) polymer having a molecular weight of 1000 or less; and/or
  e) the composition comprises a poly(oxyethylene) polymer which is a high molecular weight poly(oxyethylene) polymer and a poly(oxyethylene) polymer which is a low molecular weight poly(oxyethylene) polymer, wherein said high molecular weight poly(oxyethylene) polymer has a molecular weight that lies in a range selected from 1500 to 50000, 1500 to 40000, 2000 to 30000, 2500 to 25000, 3000 to 20000, 3500 to 15000 and 4000 to 12500 and/or wherein said low molecular weight poly(oxyethylene) polymer has a molecular weight of 1000 or less and wherein optionally, the molecular weight lies in a range selected from 100 to 1000, 150 to 800, 150 to 700, 200 to 600 and 200 to 500.

27. The composition of claim 17, wherein the composition comprises:
  a) at least one primary, secondary or tertiary amide;
  b) at least one compound according to formula 1

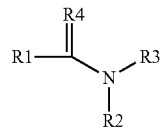

formula 1 wherein R1 is a hydrogen residue or an alkyl residue, optionally a C1-05 alkyl residue, a C1-C4 alkyl residue, a C1-C3 alkyl residue or a C1-C2 alkyl residue, R2 and R3 are identical or different and are selected from a hydrogen residue and a hydrocarbon residue, optionally an alkyl residue, with a length of the carbon chain of 1-20 atoms arranged in a linear or branched manner, and R4 is an oxygen, sulphur or selenium residue;
  c) at least one primary, secondary or tertiary amide according to formula 1

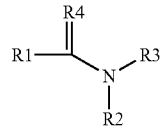

formula 1 wherein R1 is a hydrogen residue or an alkyl residue, optionally a C1-05 alkyl residue, a C1-C4 alkyl residue, a C1-C3 alkyl residue or a C1-C2 alkyl residue, R2 and R3 are identical or different and are selected from a hydrogen residue and a hydrocarbon residue, optionally an alkyl residue, with a length of the carbon chain of 1-20 atoms arranged in a linear or branched manner, and R4 is an oxygen, sulphur or selenium residue;
  d) at least one primary, secondary or tertiary carboxylic acid amide according to formula 1

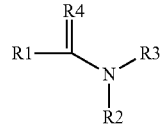

formula 1 wherein R1 is a hydrogen residue or an alkyl residue, optionally a C1-C5 alkyl residue, a C1-C4 alkyl residue, a C1-C3 alkyl residue or a C1-C2 alkyl residue, R2 and R3 are identical or different and are selected from a hydrogen residue and a hydrocarbon residue, optionally an alkyl residue, with a length of the carbon chain of 1-20 atoms arranged in a linear or branched manner, and R4 is an oxygen, sulphur or selenium residue; and/or
  e) a N,N-dialkylpropanamide, optionally N,N-dimethlypropanamide, and/or butanamide.

28. The collection device of claim 22, wherein the composition has one or more of the following characteristics:
  a) the composition is liquid, optionally aqueous;
  b) the composition has an acidic pH and/or is buffered;
  c) the composition has a pH of 4.0 to 7.0, a pH of 4.1 to 6.9, a pH of 4.2 to 6.8, a pH of 4.3 to 6.6, a pH of 4.4 to 6.3, a pH of 4.5 to 6.0, or a pH of 4.5 to 5.5;
  d) the composition is irradiation sterilized, optionally gamma irradiation sterilized;
  e) the composition has a sterility assurance level (SAL) of $10^{-6}$ or less; and/or
  f) the composition is obtainable by:
    fa) providing a composition comprising:
      i. at least one caspase inhibitor, and
      ii. at least one compound selected from a thioalcohol that is N-acetyl-cysteine or glutathione, a water-soluble vitamin, and a water-soluble vitamin E derivate; and
    fb) irradiating the composition for sterilization.

29. The collection device of claim 22, wherein
i) the at least one caspase inhibitor comprised in the composition has one or more of the following characteristics:
  a) the caspase inhibitor is a pancaspase inhibitor;
  b) the caspase inhibitor comprises a modified caspase-specific peptide;
  c) the caspase inhibitor comprises a modified caspase-specific peptide that is modified, optionally at the carboxyl terminus, with an O-Phenoxy (OPh) group;
  d) the caspase inhibitor comprises a modified caspase-specific peptide that is modified, optionally at the N-terminus, with a glutamine (Q) group;
  e) the caspase inhibitor is selected from the group consisting of Q-VD-OPh, Boc-D-(OMe)-FMK and Z-Val-Ala-Asp(OMe)-FMK;
  if) the caspase inhibitor is selected from the group consisting of Q-VD-OPh and Z-Val-Ala-Asp(OMe)-FMK; and/or
  g) the caspase inhibitor is Q-VD-OPh;
and/or
ii) the composition comprises at least one of
  a) N-acetyl-cysteine, optionally in a concentration of 0.05 mg/ml to 15 mg/ml, 0.1 mg/ml to 10 mg/ml, 0.1 mg/ml to 7.5 mg/ml, 0.1 mg/ml to 5 mg/ml, 0.1 mg/ml to 2 mg/ml, 0.2 mg/ml to 1 mg/ml, or 0.3 mg/ml to 0.8 mg/ml;
  b) glutathione, optionally in a concentration of 0.03 mg/ml to 10 mg/ml, 0.075 mg/ml to 5 mg/ml, 0.15 mg/ml to 4 mg/ml or 0.4 mg/ml to 1.3 mg/ml, wherein the glutathione is optionally in reduced form;
  c) ascorbic acid, optionally in a concentration of less than 20 mg/ml, optionally 0.1 mg/ml to 15 mg/ml, 1 mg/ml to 13 mg/ml, 1.5 mg/ml to 12 mg/ml, or 2 mg/ml to 11 mg/ml;
  d) a B vitamin, optionally in a concentration of 0.1 mg/ml to 15 mg/ml, 0.1 mg/ml to 14 mg/ml, 0.1 mg/ml to 11 mg/ml, 0.2 mg/ml to 7.5 mg/ml, or 0.2 mg/ml to 2 mg/ml, wherein the B vitamin optionally is vitamin B6;
  e) a water-soluble vitamin E derivative, optionally in a concentration of 0.5 mg/ml to 5 mg/ml, 0.75 mg/ml to 3 mg/ml, 0.9 mg/ml to 2 mg/ml, or 1 mg/ml to 1.4 mg/ml, wherein the water-soluble vitamin E derivative optionally is trolox.

30. The collection device of claim 22, wherein the composition further comprises one or more of:
  a) an anticoagulant and/or a chelating agent, optionally EDTA;
  b) a poly(oxyethylene) polymer as stabilizing agent; and/or
  c) at least one primary, secondary or tertiary amide.

31. The collection device of claim 22, wherein the composition further comprises at least one poly(oxyethylene) polymer, optionally wherein the composition has one or more of the following characteristics:
  a) the poly(oxyethylene) polymer is a polyethylene glycol, optionally unsubstituted polyethylene glycol;
  b) the composition comprises a poly(oxyethylene) polymer which is a high molecular weight poly(oxyethylene) polymer having a molecular weight of at least 1500;
  c) the composition comprises at least one poly(oxyethylene) polymer having a molecular weight below 1500, optionally wherein the at least one poly(oxyethylene) polymer is a low molecular weight poly(oxyethylene) polymer having a molecular weight of 1000 or less or has a molecular weight that lies in a range selected from 100 to 800, 150 to 700, 200 to 600 and 200 to 500;
  d) the composition comprises a poly(oxyethylene) polymer which is a high molecular weight poly(oxyethylene) polymer having a molecular weight of at least 1500 and at least one further poly(oxyethylene) polymer that is at least 100, optionally at least 200, at least 300 or at least 400 below the molecular weight of the high molecular weight poly(oxyethylene) polymer, wherein said further poly(oxyethylene) polymer optionally is a low molecular weight poly(oxyethylene) polymer having a molecular weight of 1000 or less; and/or
  e) the composition comprises a poly(oxyethylene) polymer which is a high molecular weight poly(oxyethylene) polymer and a poly(oxyethylene) polymer which is a low molecular weight poly(oxyethylene) polymer, wherein said high molecular weight poly(oxyethylene) polymer has a molecular weight that lies in a range selected from 1500 to 50000, 1500 to 40000, 2000 to 30000, 2500 to 25000, 3000 to 20000, 3500 to 15000 and 4000 to 12500 and/or wherein said low molecular weight poly(oxyethylene) polymer has a molecular weight of 1000 or less and wherein optionally, the molecular weight lies in a range selected from 100 to 1000, 150 to 800, 150 to 700, 200 to 600 and 200 to 500.

32. The collection device of claim 22, wherein the composition comprises:
  a) at least one primary, secondary or tertiary amide;
  b) at least one compound according to formula 1

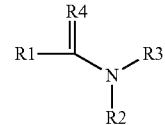

formula 1 wherein R1 is a hydrogen residue or an alkyl residue, optionally a C1-C5 alkyl residue, a C1-C4 alkyl residue, a C1-C3 alkyl residue or a C1-C2 alkyl residue, R2 and R3 are identical or different and are selected from a hydrogen residue and a hydrocarbon residue, optionally an alkyl residue, with a length of the carbon chain of 1-20 atoms arranged in a linear or branched manner, and R4 is an oxygen, sulphur or selenium residue;

c) at least one primary, secondary or tertiary amide according to formula 1

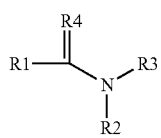

formula 1 wherein R1 is a hydrogen residue or an alkyl residue, optionally a C1-C5 alkyl residue, a C1-C4 alkyl residue, a C1-C3 alkyl residue or a C1-C2 alkyl residue, R2 and R3 are identical or different and are selected from a hydrogen residue and a hydrocarbon residue, optionally an alkyl residue, with a length of the carbon chain of 1-20 atoms arranged in a linear or branched manner, and R4 is an oxygen, sulphur or selenium residue;

d) at least one primary, secondary or tertiary carboxylic acid amide according to formula 1

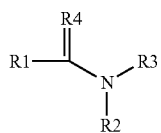

formula 1 wherein R1 is a hydrogen residue or an alkyl residue, optionally a C1-05 alkyl residue, a C1-C4 alkyl residue, a C1-C3 alkyl residue or a C1-C2 alkyl residue, R2 and R3 are identical or different and are selected from a hydrogen residue and a hydrocarbon residue, optionally an alkyl residue, with a length of the carbon chain of 1-20 atoms arranged in a linear or branched manner, and R4 is an oxygen, sulphur or selenium residue; and/or e) a N,N-dialkylpropanamide, optionally N,N-dimethlypropanamide, and/or butanamide.

33. The collection device of claim 22, wherein the collection device is a collection device for collecting blood, plasma and/or serum.

34. The collection device of claim 22, wherein the composition is comprised in the collection device in an amount effective to provide the stabilization of the amount of sample to be collected in said collection device, optionally wherein the stabilizing composition is liquid and is configured to be contacted with the biological sample in a volumetric ratio of the stabilizing composition to the biological sample selected from 10:1 to 1:20, 5:1 to 1:15, 1:1 to 1:10, 1:4 to 1:10, 1:5 to 1:9, and about 1:6 to 1:8.

35. The collection device of claim 22, wherein the collection device is evacuated.

36. The collection device of claim 22, wherein the collection device has an open top, a bottom, and a sidewall extending therebetween defining a chamber, wherein the composition is comprised in the chamber, optionally wherein the composition is liquid.

37. The collection device of claim 22, wherein the collection device is a tube, the bottom is a closed bottom, the collection device further comprises a closure in the open top, and the chamber is at a reduced pressure, optionally wherein the closure is capable of being pierced with a needle or cannula, and the reduced pressure is selected to draw a specified volume of a liquid sample into the chamber.

38. The collection device of claim 37, wherein the composition is liquid and is disposed in the chamber such that the volumetric ratio of the stabilizing composition to the specified volume of the cell-containing sample is selected from 10:1 to 1:20, 5:1 to 1:15, 1:1 to 1:10, 1:5 to 1:10, and 1:6 to 1:8.

39. A method comprising the step of collecting, a biological sample, optionally blood, from a patient directly into a chamber of the collection device according to claim 22.

40. A sterilized composition capable of stabilizing an extracellular nucleic acid population of a biological sample produced by the method of claim 1.

* * * * *

UNITED STATES PATENT AND TRADEMARK OFFICE
CERTIFICATE OF CORRECTION

| | |
|---|---|
| PATENT NO. | : 11,203,777 B2 |
| APPLICATION NO. | : 15/771820 |
| DATED | : December 21, 2021 |
| INVENTOR(S) | : Daniel Grölz et al. |

It is certified that error appears in the above-identified patent and that said Letters Patent is hereby corrected as shown below:

In the Claims

Column 89, Claim 2, Line 50:
"of 10' or less;" should read: -- of $10^{-6}$ or less; --.

Column 90, Claim 4, Line 30:
"Q-VD-OPh, Boc-D-(0Me )-FMK" should read: -- Q-VD-OPh, Boc-D-(OMe )-FMK --.

Column 94, Claim 13, Line 6:
"of 1 20 atoms" should read: -- of 1 - 20 atoms --.

Column 94, Claim 13, Line 26:
"of 1 20 atoms" should read: -- of 1 - 20 atoms --.

Column 96, Claim 23, Line 40:
"10' or less;" should read: -- $10^{-6}$ or less; --.

Column 97, Claim 24, Line 4:
"a)N-acetyl-cysteine," should read: -- a) N-acetyl-cysteine, --.

Column 98, Claim 27, Line 25:
"C1-05" should read: -- C1-C5 --.

Column 98, Claim 27, Line 44:
"C1-05" should read: -- C1-C5 --.

Column 99, Claim 29, Line 41:
"if)" should read: -- f) --.

Signed and Sealed this
Thirtieth Day of May, 2023

Katherine Kelly Vidal
*Director of the United States Patent and Trademark Office*

CERTIFICATE OF CORRECTION (continued)
U.S. Pat. No. 11,203,777 B2

Column 99, Claim 29, Line 47:
"a)N-acetyl-cysteine," should read: -- a) N-acetyl-cysteine, --.

Column 101, Claim 32, Line 39:
"C1-05" should read: -- C1-C5 --.